(12) United States Patent
Slater et al.

(10) Patent No.: US 12,077,741 B2
(45) Date of Patent: Sep. 3, 2024

(54) CROSSLINKED HYDROGEL COMPOSITIONS FOR REGULATING STATES OF ENCAPSULATED CANCER CELLS

(71) Applicants: John H. Slater, Landenberg, PA (US);
Shantanu Pradhan, Chennai (IN);
Cindy Jazmin Farino Reyes, Claymont, DE (US)

(72) Inventors: John H. Slater, Landenberg, PA (US);
Shantanu Pradhan, Chennai (IN);
Cindy Jazmin Farino Reyes, Claymont, DE (US)

(73) Assignee: University Of Delaware, Newark, DE (US)

( * ) Notice: Subject to any disclaimer, the term of this patent is extended or adjusted under 35 U.S.C. 154(b) by 596 days.

(21) Appl. No.: 16/893,330

(22) Filed: Jun. 4, 2020

(65) Prior Publication Data
US 2020/0299627 A1   Sep. 24, 2020

Related U.S. Application Data

(63) Continuation-in-part of application No. PCT/US2018/063787, filed on Dec. 4, 2018.

(60) Provisional application No. 62/594,077, filed on Dec. 4, 2017.

(51) Int. Cl.
| | |
|---|---|
| C12Q 1/37 | (2006.01) |
| C07K 5/11 | (2006.01) |
| C07K 5/113 | (2006.01) |
| C07K 7/06 | (2006.01) |
| C07K 7/08 | (2006.01) |
| C12M 1/12 | (2006.01) |
| C12N 5/09 | (2010.01) |
| G01N 1/30 | (2006.01) |
| G01N 21/64 | (2006.01) |
| G01N 33/50 | (2006.01) |

(52) U.S. Cl.
CPC .......... *C12M 25/00* (2013.01); *C07K 5/1019* (2013.01); *C07K 5/1021* (2013.01); *C07K 7/06* (2013.01); *C07K 7/08* (2013.01); *C12N 5/0693* (2013.01); *G01N 1/30* (2013.01); *G01N 21/6428* (2013.01); *G01N 33/5011* (2013.01); *G01N 33/5091* (2013.01); *C12N 2503/00* (2013.01); *C12N 2533/40* (2013.01); *C12N 2533/50* (2013.01); *G01N 2021/6439* (2013.01)

(58) Field of Classification Search
CPC .... C12M 25/00; C07K 5/1019; C07K 5/1021; C07K 7/06; C07K 7/08; C12N 5/0693; C12N 2503/00; C12N 2533/40; C12N 2533/50; C12N 2537/10; C12N 5/0012; G01N 1/30; G01N 21/6428; G01N 33/5011; G01N 33/5091; G01N 2021/6439
See application file for complete search history.

(56) References Cited

U.S. PATENT DOCUMENTS

| | | | |
|---|---|---|---|
| 5,314,805 A | 5/1994 | Haugland et al. | |
| 2013/0234372 A1 | 9/2013 | Almutairi et al. | |
| 2013/0236879 A1 | 9/2013 | Berry et al. | |
| 2015/0082468 A1* | 3/2015 | Bhatia ................ | C12N 5/0062 435/177 |
| 2015/0175972 A1* | 6/2015 | Jabbari ............... | C12N 5/0695 435/382 |
| 2015/0253237 A1 | 9/2015 | Castellamau et al. | |
| 2017/0131273 A1 | 5/2017 | Arinzeh et al. | |
| 2017/0131275 A1 | 5/2017 | Anderson et al. | |
| 2017/0267970 A1 | 9/2017 | Gupta et al. | |
| 2017/0313827 A1 | 11/2017 | Zhu et al. | |

OTHER PUBLICATIONS

Lee et al. (Biotechnol. Prog. 2005, 21, 1736-1741).*
Jiang et al. (J. Mater. Chem. B 2017, 5, 173).*
Shih et al. (Biomacromol. 2016, 17, 3872-3882).*
Aguirre-Ghiso. J., "Models, Mechanisms and Clinical Evidence for Cancer Dormancy", Nature Reviews, vol. 7. Nov. 2007, pp. 834-846.
Aguirre-Ghiso et al., "Targeting Dormant Cancer" Nature Medicine, vol. 19, No. 3, Mar. 2013, pp. 276-277.
Banys et al., "Dormancy in Breast Cancer", Breast Cancer: Targets and Therapy, 2012:4, pp. 183-191.
Barkin et al., "Metastatic Growth from Dormant Cells Induced by a Col-I-Enriched Fibrotic Environment", Cancer Res., 70(14), Jul. 15, 2010, pp. 5706-5716.
Cavnar et al., "Modeling Selective Elimination of Quiescent Cancer Cells from Bone Marrow", Neoplasia, vol. 17, No. 8, Aug. 2015, pp. 625-633.
Cheng et al., "Micro-Environmental Mechanical Stress Controls Tumor Spheroid Size and Morphology by Suppressing Proliferation and Inducing Apoptosis in Cancer Cells", PLoS One, vol. 4, Issue 2, Feb. 2009, 11 pages.

(Continued)

*Primary Examiner* — Michael G. Hartley
*Assistant Examiner* — Melissa J Perreira
(74) *Attorney, Agent, or Firm* — BUCHANAN INGERSOLL & ROONEY PC

(57) ABSTRACT

The present invention discloses crosslinked poly(alkylene glycol) (PAG)-based hydrogel compositions, systems containing a plurality of cancer cells in contact with a cell culture media and encapsulated in the crosslinked PAG-based hydrogel composition and methods of making such crosslinked hydrogel compositions and systems. Also disclosed herein are methods of using such compositions and systems, such as, for example for screening an agent for effectiveness of the agent against cancer cells. Also disclosed herein are kits containing one or more components including one or more systems of the present disclosure and one or more instructions.

25 Claims, 20 Drawing Sheets
(10 of 20 Drawing Sheet(s) Filed in Color)
Specification includes a Sequence Listing.

(56) References Cited

OTHER PUBLICATIONS

Clark et al., "A Liver Microphysiological System of Tumor Cell Dormancy and Inflammatory Responsiveness is Affected by Scaffold Properties", Royal Society of Chemistry, Lab Chip, 2017, 17, pp. 156-168.

Fang et al., "From Competency to Dormancy: A 3D Model to Study Cancer Cells and Drug Responsiveness", J. Transl Med., 2016, 14:38,13 pages.

Fang et al., "Tumor Bioengineering Using Transglutaminase Cross-linked Hydrogel", PLoS One, Aug. 2014, vol. 9, Issue 8, 10 pages.

Ghajar, C., Metastasis Prevention by Targeting the Dormant Niche, Nature Reviews, vol. 15, Apr. 2015, pp. 238-247.

Ghajar et al., "The Perivascular Niche Regulates Breast Tumour Dormancy", Nature Cell Biology, vol. 15, No. 7, Jul. 2013, 20 pages.

Giancotti, F., "Mechanisms Governing Metastatic Dormancy and Reactivation", Cell., Nov. 7, 2013, 155(4), pp. 750-764.

Gomis et al., "Tumor Cell Dormancy", Molecular Oncology, 11, 2017, pp. 62-78.

Grandhi et al., "Chemomechanically Engineered 3D Organotypic Platforms of Bladder Cancer Dormancy and Reactivation", Biomaterials, 142, 2017, pp. 171-185.

Hao et al., "Biomimetic Hydrogels Incorporating Polymeric Cell-Adhesive Peptide to Promote the 3D Assembly of Tumoroids", Biomacromolecules, Nov. 14, 2016, 17(11), pp. 3750-3760.

Hao et al., "Visible Light Cured Thiol-vinyl Hydrogels with Tunable Degradation for 3D Cell Culture", Acta Biomater., Jan. 2014, 10(1), 27 pages.

Hassel et al., "Human Organ Chip Models Recapitulate Orthotopic Lung Cancer Growth, Therapeutic Responses, and Tumor Dormancy In Vitro", Cell Reports, 2017, 21, pp. 508-516.

Huang et al., "Peptide Hydrogelation and Cancer Encapsulation for 3D Culture of MCF-7 Breast Cancer Cells", PLos One, Mar. 2013, vol. 8, Issue 3, 15 pages.

Hurst et al., "Identification of Novel Drugs to Target Dormant Micrometastases", BMC Cancer, 2015, 15:404, 12 pages.

Hurst et al., "Targeting Dormant Micrometastases: Rationale, Evidence to Date and Clinical Implications", Ther. Adv. Med. Oncol., 2016, vol. 8(2), pp. 126-137.

Imamura et al., "Comparison of 2D- and 3D-Culture Models as Drug-testing Platforms in Breast Cancer", Oncology Reports, 33, 2015, pp. 1837-1843.

Jongpaiboonkit et al., "An Adaptable Hydrogel Array Format for 3-dimensional Cell Culture and Analysis", Biomaterials, Aug. 2008, 29(23), pp. 3346-3356.

Keeratichamroen et al., "Mechanism of ECM-induced Dormancy and Chemoresistance in A549 Human Lung Carcinoma Cells", Oncology Reports, 2018, 39, pp. 1765-1774.

Luskin et al., "Targeting Minimal Residual Disease: A Path to Cure?", Nature Reviews, Cancer, 2018, 9 pages.

Marlow et al., "A Novel Model of Dormancy for Bone Metastatic Breast Cancer Cells", Cancer Res., Dec. 1, 2013, 73(23), 15 pages.

Narkhede et al., "An In Vitro Hyaluronic Acid Hydrogel Based Platform to Model Dormancy in Brain Metastatic Breast Cancer Cells", Acta Biomaterialia, 2020, 107, pp. 65-77.

Pantel et al., "Dissecting the Metastatic Cascade", Nature Reviews, Jun. 2004, vol. 4, pp. 448-456.

Phan et al., "The Dormant Cancer Cell Life Cycle", Nature Reviews, 2020, 14 pages.

Pogany et al., "Role of the Basement Membrane in Tumor Cell Dormancy and Cytotoxic Resistance", Oncology, 2001, 60, 274-281.

Pradhan et al., "Datasets Describing Hydrogel Properties and Cellular Metrics for Modeling of Tumor Dormancy", Data in Brief, 2019, 25, 9 pages.

Pradhan et al., "Engineered In Vitro Models of Tumor Dormancy and Reactivation", Journal of Biological Engineering, 2018, 12:37, 19 pages.

Pradhan et al., "Fabrication, Characterization, and Implementation of Engineered Hydrogels for Controlling Breast Cancer Cell Phenotype and Dormancy", MethodsX, 2019, 6, pp. 2744-2766.

Pradhan et al., "Fundamentals of Laser-Based Hydrogel Degradation and Applications in Cell and Tissue Engineering", Advanced Healthcare Materials, Oct. 24, 2017, vol. 6, Issue 24, https://doi.org/10.1002/adhm.201700681, 53 pages.

Pradhan et al., "PEG-fibrinogen Hydrogels for Three-dimensional Breast Cancer Cell Culture", J. Biomed Mater. Res., Part A. 2015:00A:000-000, 17 pages.

Pradhan et al., "Three-dimensional Modeling of Metastatic Breast Cancer Dormancy Using Tunable PEG-based Hydrogels", ASCB/EMBO 2017 Meeting, Dec. 5, 2017, 28 pages.

Pradhan et al., "Tunable Hydrogels for Controlling Phenotypic Cancer Cell States to Model Breast Cancer Dormancy and Reactivation", Biomaterials, 215, 2019, 18 pages.

Preciado et al., "Immobilization Platform to Induce Quiescence in Dormancy-capable Cancer Cells", Technology, Sep. 2017, vol. 5, No. 3, 10 pages.

Rao et al., "Bioengineered Models to Study Tumor Dormancy", Journal of Biological Engineering, 2019, 13:3, 12 pages.

Reynolds et al., "Mechanical Confinement via a PEG/Collagen Interpenetrating Network Inhibits Behavior Characteristic of Malignant Cells in the Triple Negative Breast Cancer Cell Line MDA. MB.231", Acta Biomaterialia 77, 2018, pp. 85-95.

Rodenhizer et al., "The Current Landscape of 3D In Vitro Tumor Models: What Cancer Hallmarks are Accessible for Drug Discovery?", Adv. Healthcare Mater., 2018, 1701174, 36 pages.

Sosnoski et al., "Dormancy and Growth of Metastatic Breast Cancer Cells in a Bone-like Microenvironment", Clin. Exp. Metastasis, Mar. 8, 2015, 10 pages.

Weiss et al., "The Impact of Adhesion Peptides within Hydrogels on the Phenotype and Signaling of Normal and Cancerous Mammary Epithelial Cells", Biomaterials, May 2012, 33(13), pp. 3548-3559.

Wenzel et al., "3D High-content Screening for the Identification of Compounds that Target Cells in Dormant Tumor Spheroid Regions" Experimental Cell Research, 2014, 323, pp. 131-143.

International Preliminary Report on Patentability for International Application No. PCT/US2018/063787, dated Jun. 9, 2020, 23 pages.

International Search Report and Written Opinion for International Application No. PCT/US2018/063787, dated Mar. 5, 2019, 26 pages.

Farino et al., "The Influence of Matrix Induced Dormancy on Metastatic Breast Cancer Chemoresistance" Jul. 29, 2020, Drug Resistance Manuscript, 42 pages.

\* cited by examiner

CROSSLINKED HYDROGEL COMPOSITIONS FOR REGULATING STATES OF ENCAPSULATED CANCER CELLS

CROSS-REFERENCE TO RELATED APPLICATIONS

This application is a continuation-in-part of International Application No. PCT/US2018/063787, filed Dec. 4, 2018, which claims priority to U.S. Provisional Patent Application No. 62/594,077, filed Dec. 4, 2017, the disclosures of each of these applications being incorporated herein by reference in their entireties for all purposes.

The Sequence Listing for this application is labeled as "UOD-514US-SequenceListing.txt" which was created on Jun. 3, 2020 and is 603 bytes. The contents of the paper and computer readable copies of this SEQUENCE LISTING are the same as the SEQUENCE LISTING filed in International Application No. PCT/US2018/063787, filed Dec. 4, 2018, the entire content of which is incorporated herein by reference in its entirety.

STATEMENT REGARDING FEDERALLY SPONSORED RESEARCH

This invention was made with government support under Grant No. R21CA214299 awarded by the National Institutes of Health/National Cancer Institute under IMAT program; Grant No. P20 GM103446) awarded by the National Institutes of Health/National Institute of General Medical Sciences; and Grant No. IIA 1301765 awarded by the National Science Foundation. The government has certain rights in the invention.

BACKGROUND OF THE INVENTION

Metastasis is responsible for the vast majority of cancer-related deaths worldwide. A major challenge in the prevention and treatment of metastasis occurs due to a lack of understanding of mechanisms driving metastatic recurrence and more importantly, the ability of cancer cells to lie dormant in different organs of the body for long time periods. Disseminated tumor cells (DTCs) from the primary tumor can undergo latency periods ranging from months to decades depending on cancer subtype, molecular characteristics and receptor status, patient lifestyle, systemic inflammation and other factors. Upon being stimulated by specific cellular or biochemical factors, dormant DTCs can undergo a proliferative switch to form micrometastases, and further on, overt macrometastases. This metastatic relapse is often characterized by increased chemoresistance, leading to poor patient outcome and reduced survival. Hence, preemptively targeting dormant tumor cells offers a potential window of opportunity for prevention of metastatic relapse in patients.

In the primary tumor microenvironment, cancer cells disseminate from the tumor mass and enter the blood circulation as circulating tumor cells. Some of these cell populations survive in the circulation and extravasate in secondary organs (including bone marrow, liver, brain, lung). Depending on the microenvironmental conditions of the secondary organ, these cancer cells can undergo various fates as observed in in vivo models and in clinical scenarios. These fates are classified as: 1) cell death, 2) cellular dormancy, 3) tumor mass dormancy, and 4) metastatic outgrowth and are described below.

A majority of DTCs in secondary organs undergo cell death due to apoptosis from microenvironmental stress and immunomodulatory suppression in the complex secondary milieu, which is generally very different from the primary tumor niche. However, autophagy-induced death has also been observed in some cases. Surviving DTCs usually undergo a state of cellular dormancy characterized by $G_0$ cell cycle arrest, altered metabolic profiles and induction of anti-apoptotic cell survival mechanisms. These persistent single tumor cells have been experimentally observed in in vivo models and in human subjects with no clinically detectable disease. In addition to single cell dormancy, small cell clusters of DTCs may also be present in secondary niches in a state of balanced proliferation and death, thereby maintaining overall tumoral homeostasis. These are characterized by low proliferation and may be maintained through a mix of pro- and anti-angiogenic stromal and cellular cues that balance each other. This state may also be mediated via immune regulation. Finally, dormant single DTCs or dormant cell clusters can be triggered toward aggressive and invasive growth via various factors (angiogenic signaling, inflammatory cytokines and others). This dormancy-proliferation switch eventually leads to formation of overt macrometastases and metastatic relapse, with poor outcomes for patients.

Most of the knowledge of molecular mechanisms underlying tumor dormancy has been obtained from in vivo models, which are beset with several limitations and challenges including, but not limited to, complexity of organism, fate-tracking and imaging of single DTCs, stochastic nature of dormancy and metastasis, poor classification of dormancy-specific cell lines.

Hence, there is a need for in vitro models that can recapitulate specific fates of DTCs, facilitate further investigation of underlying biological mechanisms necessary for understanding tumor dormancy, and for use in pre-clinical information for future drug development applications.

SUMMARY OF THE INVENTION

So far, only a few models have been developed that recapitulate tumor dormancy and metastatic relapse conditions in vitro. Disclosed herein is a system that uses an engineered synthetic material-based platform, which provides an opportunity to carefully control microenvironmental properties and associated cell-matrix interactions, that eventually direct encapsulated cancer cells toward specific fates. Also disclosed herein, are detailed characterization of material properties of such a system and associated phenotypic behavior in cancer cells. Furthermore, also disclosed herein is a method of phenotypic classification of cancer cell states based on several cellular metrics, that mimic the potential fates of DTCs described earlier. The system of the present invention can be used to investigate mechanisms underlying extracellular matrix (ECM)-mediated tumor dormancy, influence of matrix properties in directing cancer cell fate, and spatiotemporal modulation of matrix properties to mimic metastatic relapse. Without wishing to be bound by any particular theory, it is believed that these investigations will help identify potential targets specific to tumor dormancy and metastatic relapse and aid in the discovery and development of therapeutic strategies for prevention of metastasis, prolonging of dormancy, and preemptive elimination of dormant cells.

In an aspect of the present invention, there is provided a system comprising a crosslinked poly(alkylene glycol) (PAG)-based hydrogel composition, a cell culture media in contact with the crosslinked PAG-based hydrogel composition, and a plurality of cancer cells in contact with the cell culture media and encapsulated in the crosslinked PAG-based hydrogel composition.

In an embodiment, the system further comprises a crosslinked PAG-based hydrogel composition formed by photopolymerizing a polymer-peptide macromer and a cell-adhesive macromer in the presence of a Type 1 ultraviolet (UV) photoinitiator, wherein the cell-adhesive macromer comprises a second poly(alkylene glycol) covalently conjugated with a cell-adhesive peptide comprising a peptide motif selected from the group consisting of RGDS (SEQ ID NO: 4), RDGS (SEQ ID NO: 5), RGES (SEQ ID NO: 6), REGS (SEQ ID NO: 7), IKVAV (SEQ ID NO: 8), VVIAK (SEQ ID NO: 9), YIGSR (SEQ ID NO: 10), YSRIG (SEQ ID NO: 11), DGEA (SEQ ID NO: 12), DAEG (SEQ ID NO: 13), and combinations thereof.

The cell-adhesive macromer of the present disclosure may comprise a second poly(alkylene glycol) covalently conjugated with a cell-adhesive peptide.

In yet another embodiment, the system further comprises the crosslinked PAG-based hydrogel composition formed by photopolymerizing the polymer-peptide macromer and optionally a co-monomer in the presence of the Type 1 ultraviolet (UV) photoinitiator. Suitable co-monomer includes but is not limited to n-vinyl pyrrolidone (NVP).

In yet another embodiment, the system comprises the crosslinked PAG-based hydrogel composition formed by photopolymerizing the polymer-peptide macromer, the cell-adhesive macromer and the co-monomer in the presence of the Type 1 ultraviolet (UV) photoinitiator.

In another aspect, there is provided a method of regulating a state of cancer cells comprising providing a system as disclosed hereinabove, adding a reactant to the system, wherein the reactant is selected from the group consisting of a co-monomer, a cell-adhesive macromer, a hydrogel digesting agent and combinations thereof, and adjusting a concentration of the reactant, whereby the state of the cancer cells is either maintained in a first cancer state or switched from the first cancer state to a second cancer state. The reactant may be selected from the group consisting of a co-monomer, a cell-adhesive macromer, a hydrogel digesting agent and combinations thereof. Each of the first and the second cancer state can be selected from the group consisting of invasive growth, single cell restricted survival dormancy, single cell balanced survival dormancy and tumor mass balanced survival dormancy, and the first state is different from the second state.

In one embodiment of the method of regulating a state of the cancer cells, the step of providing a system further comprises providing:
(i) a first system comprising the cancer cells in contact with the cell culture media and encapsulated in a first crosslinked PAG-based hydrogel composition formed by photopolymerizing a polymer-peptide macromer in the presence of a Type 1 ultraviolet (UV) photoinitiator, wherein the first state of the cancer cells in the first system is single cell restricted survival dormancy;
(ii) a second system comprising the cancer cells in contact with the cell culture media and encapsulated in a second crosslinked PAG-based hydrogel composition formed by photopolymerizing the polymer-peptide macromer and a cell-adhesive macromer in the presence of the Type 1 ultraviolet (UV) photoinitiator;
(iii) a third system comprising the cancer cells in contact with the cell culture media and encapsulated in a third crosslinked PAG-based hydrogel composition by photopolymerizing the polymer-peptide macromer and a co-monomer in the presence of the Type 1 ultraviolet (UV) photoinitiator, wherein the co-monomer comprises n-vinyl pyrrolidone (NVP); and/or
(iv) a fourth system comprising the cancer cells in contact with the cell culture media and encapsulated in a fourth crosslinked PAG-based hydrogel composition by photopolymerizing the polymer-peptide macromer, the cell-adhesive macromer and the co-monomer in the presence of the Type 1 ultraviolet (UV) photoinitiator,
wherein each of the four systems regulates cancer cells in one of the cancer states selected from the group consisting of invasive growth, single cell restricted survival dormancy, single cell balanced survival dormancy and tumor mass balanced survival dormancy state.

In an embodiment, the step of adjusting a concentration of the reactant in the system comprises photopolymerizing the reactant with the PAG-based crosslinked hydrogel in the presence of the Type 1 ultraviolet (UV) photoinitiator.

In an aspect, there is provided a method of screening an agent for effectiveness of the agent against cancer cells. The method comprises providing a system as disclosed hereinabove and determining the state of the cancer cells encapsulated in the crosslinked hydrogels, as disclosed hereinabove and shown in FIG. 3. The method further comprises adjusting the concentration of the one or more reactants, whereby the state of the cancer cells is maintained in the first cancer state selected from the group consisting of invasive growth, single cell balanced survival dormancy and tumor mass balanced survival dormancy. The method also comprises contacting the cancer cells with an effective amount of the agent selected from the group consisting of a drug, an antibody, and a biologic, and monitoring the state of the cancer cells periodically from before (day 0) to after (day n with n being from 1-90 or 1-60 or 1-50 or 1-20 or 1-15) the step of contacting the cancer cells, by measuring cell viability and viable cell density. The method further comprises assessing the efficacy of the agent on the cells by comparing measured cell viability and viable cell density on day 0 with that on day n.

In an embodiment of the method of screening an agent for effectiveness of the agent against cancer cells, the step of screening an agent further comprises providing four systems, such that each system comprises cancer cells in one of the four cancer states and adjusting the concentration of the one or more reactants in at least one of the four systems, whereby the state of the cancer cells is maintained in the first cancer state. The method also includes contacting the cancer cells in at least one of the four systems, with an effective amount of the agent selected from the group consisting of a drug, an antibody, and a biologic; monitoring the state of the cancer cells in at least one of the four systems, periodically from before (day 0) to after (day n with n being from 1-90 or 1-60 or 1-50 or 1-20 or 1-15) the step of contacting the cancer cells, by measuring cell viability and viable cell density; and assessing an efficacy of the agent on the cancer cells by comparing cell viability and viable cell density on day 0 with that on day n from one system with at least another of the four systems.

In an aspect of the invention, there is provided a kit comprising a first component comprising a system comprising a plurality of cancer cells in contact with the cell culture media and encapsulated in a crosslinked poly(alkylene glycol) (PAG)-based hydrogel composition, as disclosed hereinabove and a second component comprising an instruction for regulating the state of the cancer cells as disclosed hereinabove.

In an embodiment, the kit further comprises a third component comprising a co-monomer, e.g. NVP. In another embodiment, the kit also comprises a fourth component comprising a cell-adhesive macromer, e.g., PEG-RGDS. In yet another embodiment, the kit comprises a fifth component comprising a hydrogel digesting agent. In another embodiment, the second component may further comprise an instruction for screening an agent for effectiveness of the agent against cancer cells, as disclosed hereinabove.

In another aspect, there is a kit comprising a first component comprising a precursor hydrogel composition comprising a polymer-peptide macromer, e.g., PEG-PQ and a Type I photoinitiator, and a second component comprising an instruction for making the crosslinked PAG-based hydrogel as disclosed hereinabove. The kit may further comprise a third component comprising a co-monomer, a fourth component comprising a cell-adhesive macromer, and instructions for making the crosslinked PAG-based hydrogel, as disclosed hereinabove. The kit may further comprise a fifth component comprising a hydrogel digesting agent, a sixth component comprising a plurality of cancer cells in contact with a cell culture media, and instruction for screening an agent for effectiveness of the agent against cancer cells, as disclosed hereinabove.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Formulations with single cells greater than 80% of total cell population and clustered cells less than 20% of total population are grouped into 'single cell balanced survival dormancy' category and remaining formulations are grouped into 'tumor mass balanced survival dormancy' category. Difference is considered statistically significant when p-value<0.01 (for viable cell density) and p-value<0.05 (cell viability), one-way ANOVA test; n=6 z-stacks from 3 hydrogels per condition.

Figure 4:
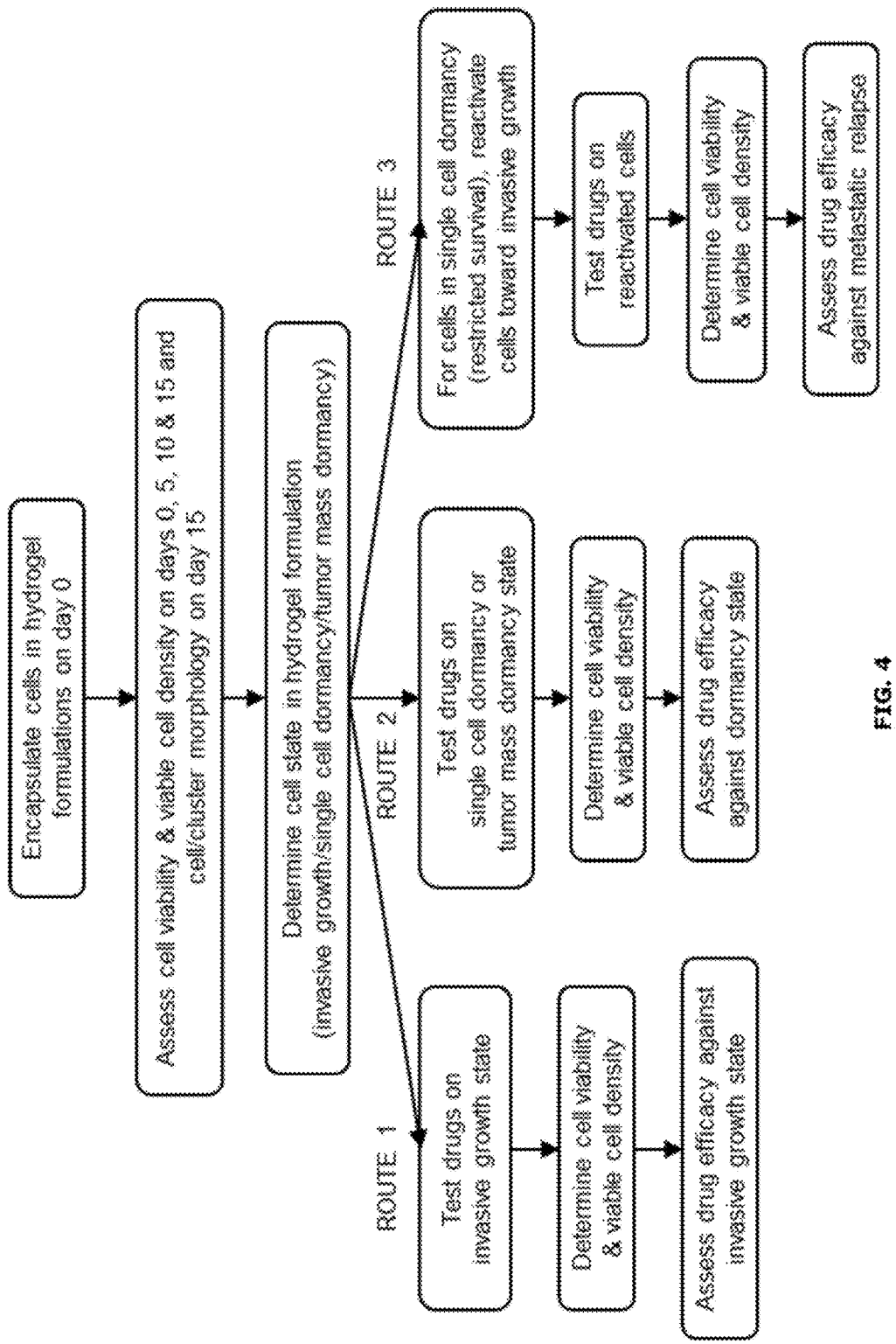

FIG. 4 shows an exemplary flowchart for drug screening in accordance with various embodiments of the present invention. Cancer cells are encapsulated in various crosslinked hydrogel compositions and maintained in 3D culture for 15 days. Cellular phenotypic metrics are evaluated on days 0, 5, 10 and 15, and relevant cell states are determined and verified. Subsequently, three possible routes for screening can be followed. In route 1, hydrogels supporting invasive growth state are contacted with therapeutic agent(s) and treatment efficacy against invasive cancers is assessed via quantification of viability and viable cell density to determine efficacy. In route 2, hydrogels inducing single cell restricted survival dormancy, single cell balanced survival dormancy and tumor mass balanced survival dormancy are contacted with therapeutic agent(s) and treatment efficacy against tumor dormancy is assessed via quantification of viability and viable cell density. In route 3, hydrogels inducing single cell restricted survival dormancy are crosslinked further with acrylate-PEG-peptide(s) (cell-adhesive peptide sequence) to induce dormancy-proliferation switch. The relapsed cells are contacted with therapeutic agent(s) and treatment efficacy against relapsed cancers is assessed via quantification of viability and viable cell density.

Figure 5:
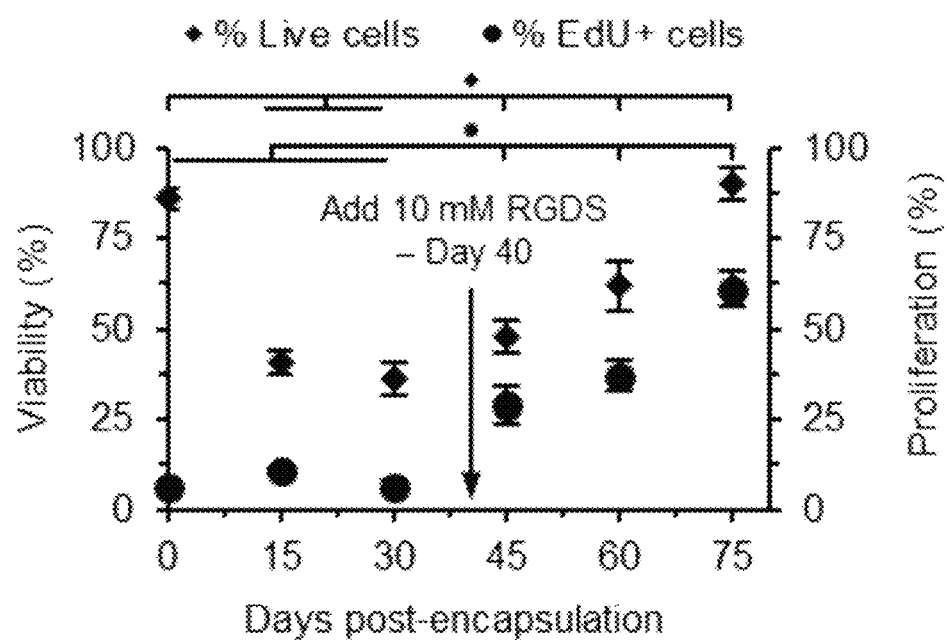

FIG. 5 shows the dormancy-proliferation switch recapitulating metastatic relapse. MDA-MB-231 cells were encapsulated in hydrogels with 0 mM PEG-RGDS and 0 mM NVP on day 0, crosslinked with 10 mM PEG-RGDS on day 40 and cultured further till day 75. Quantification of cell viability (diamond) and proliferation (circle) over 75 days is shown. Values represent mean± standard deviation. Difference is considered statistically significant when p<0.05. n=6 z-stacks from 3 hydrogels per condition.

Figure 6:
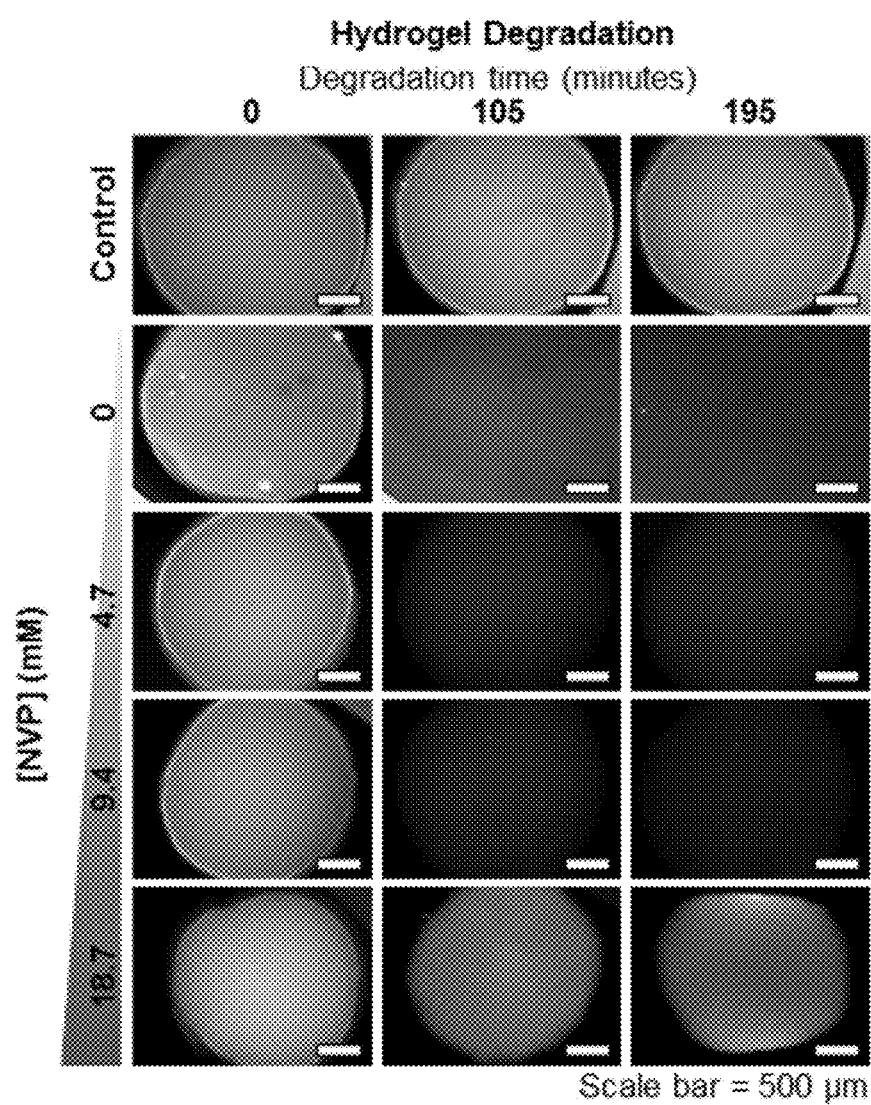

FIG. 6 shows representative images of hydrogels undergoing different rates of degradation. PEG-PQ hydrogels containing 0-18.7 mM NVP and fluorescently labeled with methacryloxyethyl thiocarbamoyl rhodamine B are incubated with 100 μg/mL collagenase IV and imaged at specific time points. Control represents hydrogels in PBS buffer with no collagenase. Changes in fluorescence intensity over time is used to quantify relative degradation. Scale bar=500 μm.

Figure 7:
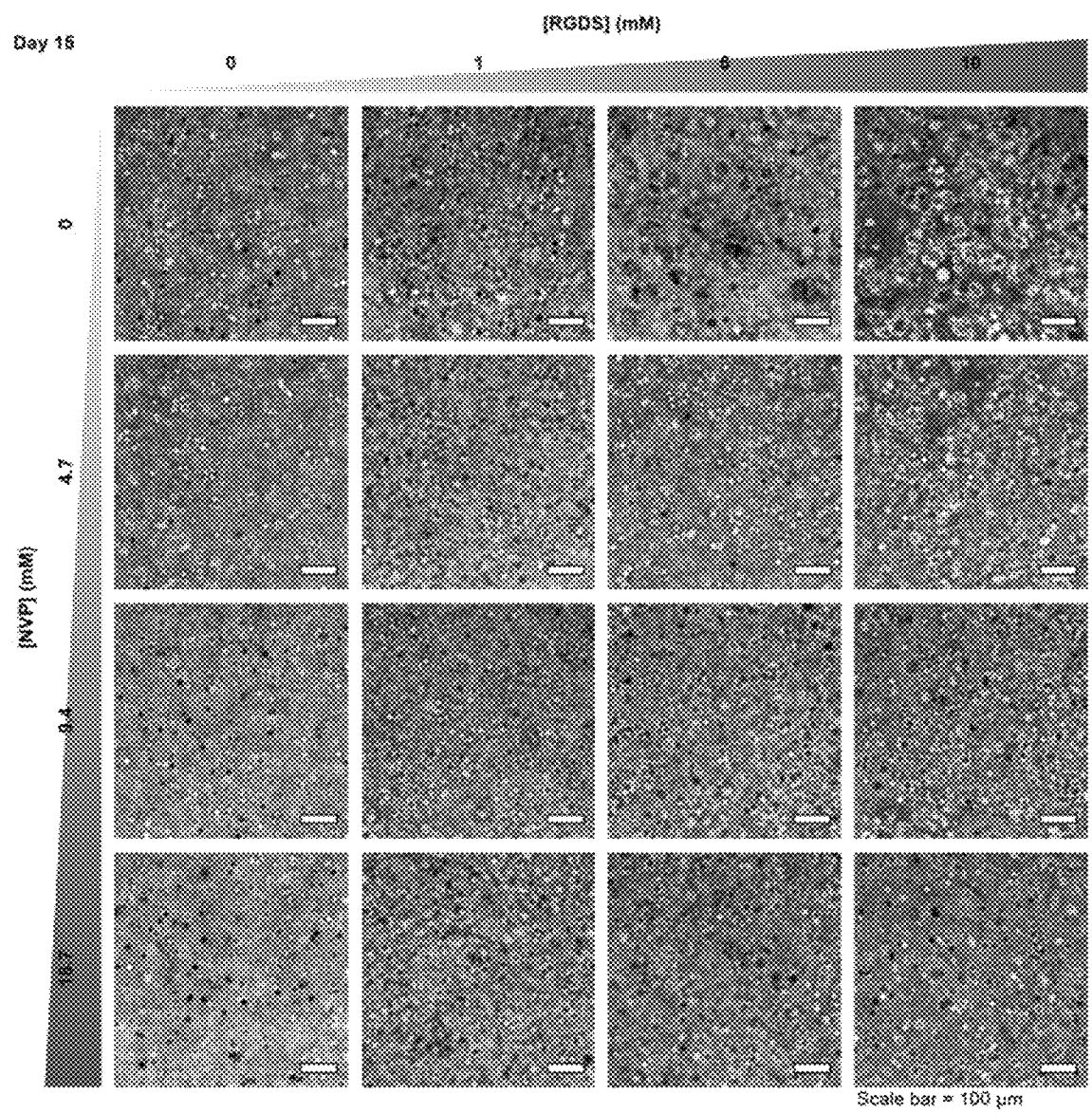

FIG. 7 displays representative phase contrast maximum intensity z-projections of MDA-MB-231 cells encapsulated in hydrogels with varying RGDS and NVP concentrations on day 15. Black objects represent dead cells. Scale bar=100 μm.

Figure 8A:
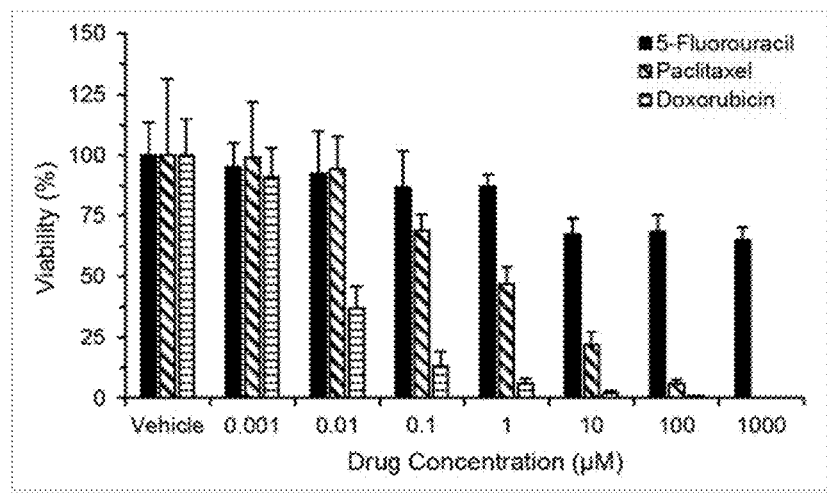
Figure 8B:
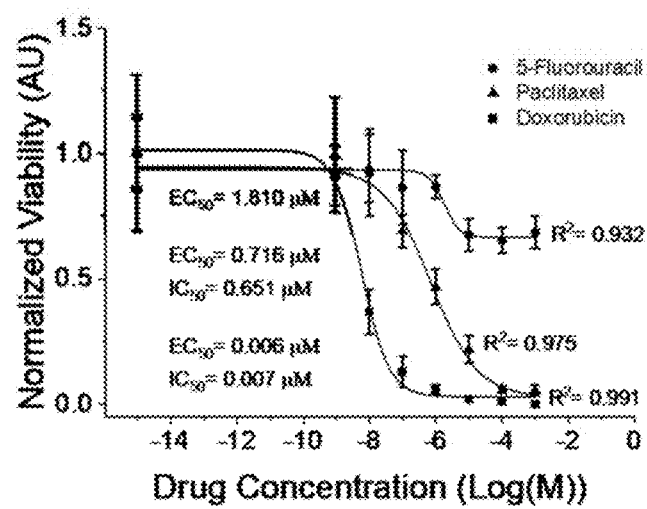

FIGS. 8A and 8B display response of MDA-MB-231 cells cultured on tissue culture plastic (2D) to 5-Fluoruracil, Paclitaxel, and Doxorubicin. FIG. 8A displays quantification of MDA-MB-231 cell viability cultured on tissue culture plastic (2D) after 48 hr drug exposure. n=6 images from 6 individual wells. Values represent mean±standard deviation. FIG. 88 displays dose-response curves for doxorubicin (black), paclitaxel (blue), and 5-fluorouracil (red) with $EC_{50}$ and $IC_{50}$ values. Data points represent mean±standard deviation.

Figure 9:
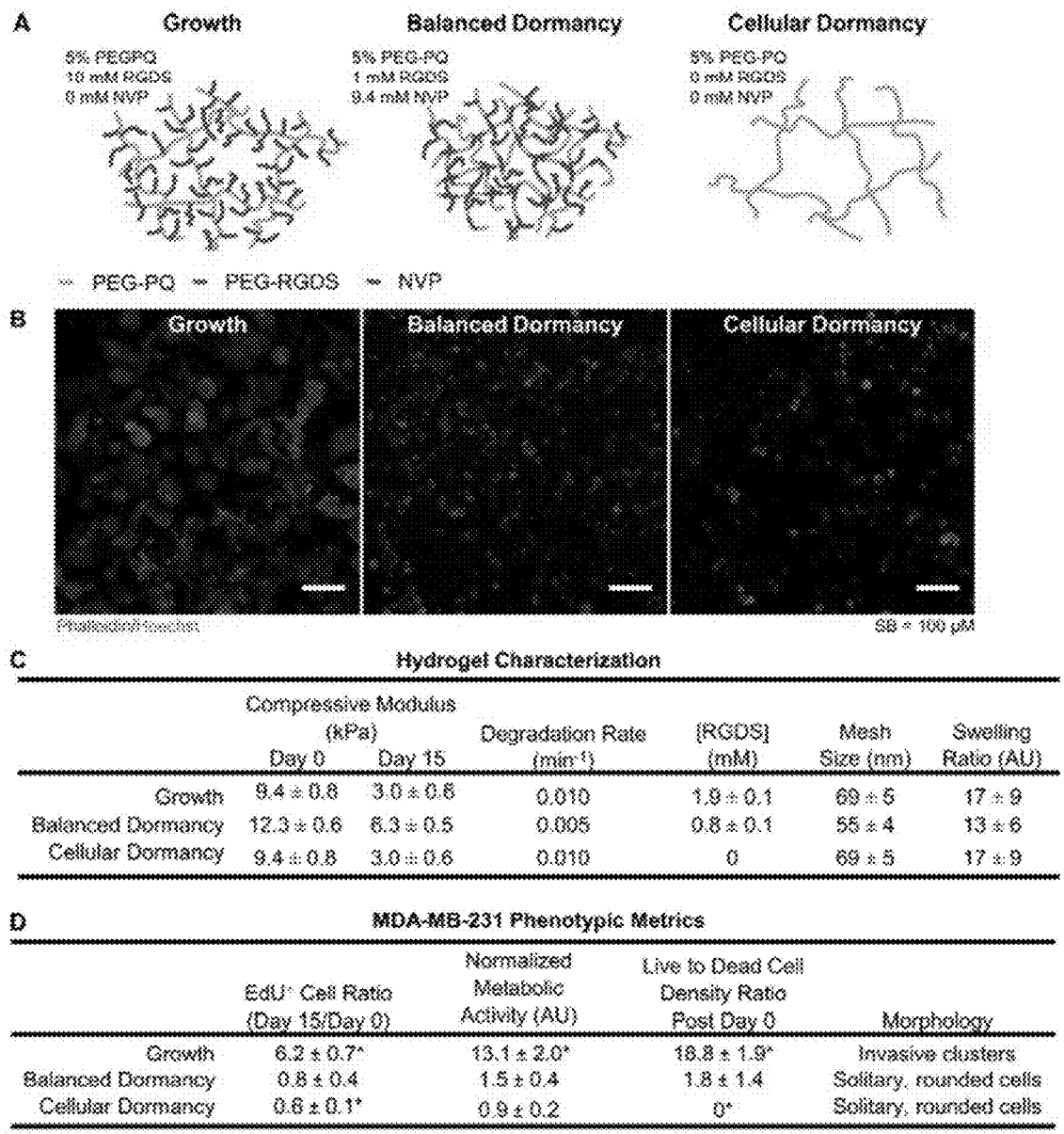

FIG. 9 displays hydrogel characterization & MDA-MB-231 phenotypic metrics, as follows: (A) Schematics of three hydrogel formulations used to induce growth, balanced dormancy, or cellular dormancy in MDA-MB-231s. (B) Representative maximum intensity z-projections from 3D image stacks of MDA-MB-231s fluorescently labeled with phalloldin (red:F-actin) and Hoechst (cyan:nuclei) after 15 days in culture. SB=100 µm. (C) Table displaying hydrogel properties (compressive moduli at days 0 and 15, degradation rate, PEG-RGDS concentration, pore size, and swelling ratio) for the three formulations. (D) Table displaying the influence of hydrogel composition on MDA-MD-231 proliferation (EdU+), metabolic activity, live to dead cell density ratio post day 0, and morphology. The theoretical mesh size of hydrogel networks calculated from release studies of 150 kDa FITC-labeled dextran using the Stokes-Einstein equation in the absence of cells. Degradation tests were performed by exposure to collagenase in the absence of cells* indicates statistical significance (p<0.05). Hydrogel schematics in (A) reproduced with permission from 31.

Figure 10:
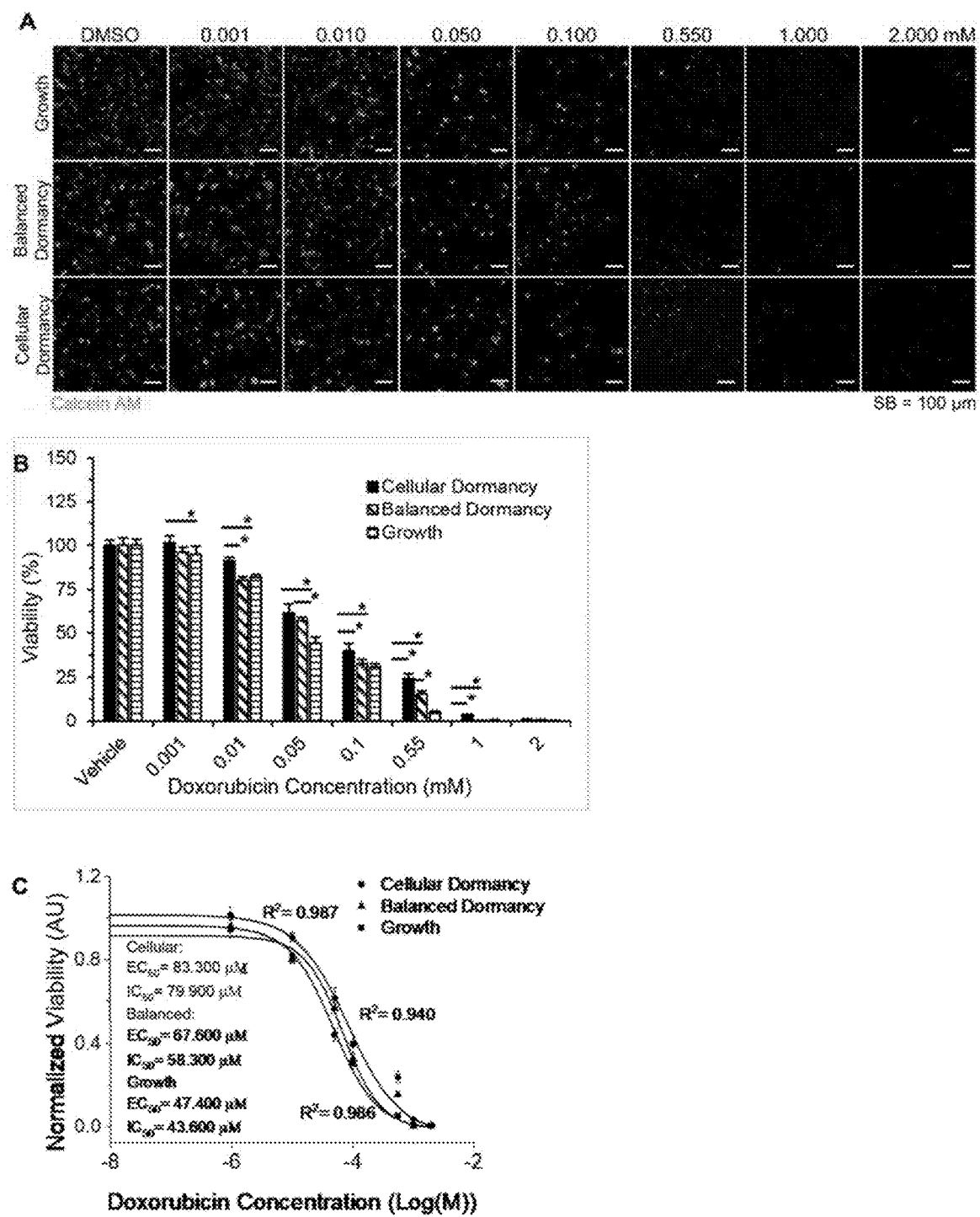

FIG. 10 displays response of MDA-MB-231 cells to Doxorubicin as follows: (A) Representative maximum intensity z-projections of 3D image stacks of MDA-MB-231s fluorescently labeled with Calcein AM (live cells: green) after 48 hr exposure to a media+1% v/v DMSO vehicle control (DMSO) or varying concentrations of doxorubicin. Top row:growth; middle row:balanced dormancy; bottom row:cellular dormancy. SB=100 µm. (B) Quantification of cell viability. * indicates p<0.05. n=5 z-stacks from 5 individual hydrogels for each formulation. Values represent mean t standard deviation. (C) Dose-response curves with $EC_{50}$ and $IC_{50}$ values for growth (black), balanced dormancy (blue), cellular dormancy (red). Data points represent mean± standard deviation.

Figure 11:
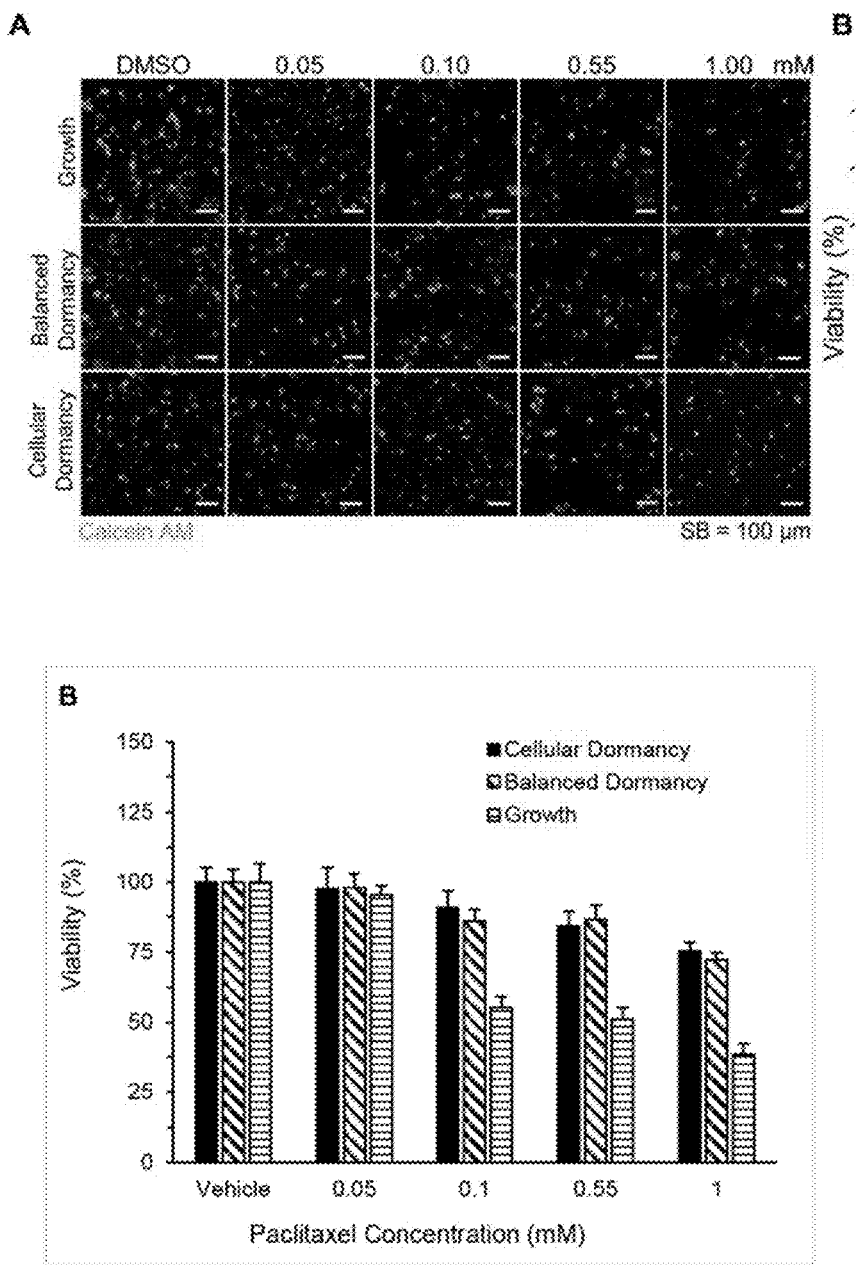

FIG. 11 displays response of MDA-MB-231s to Paclitaxel as follows: (A) Representative maximum intensity z-projections of 3D image stacks of MDA-MB-231s fluorescently labeled with Calcein AM (live cells:green) after 48 hr exposure to a media+1% v/v DMSO vehicle control (DMSO) or varying concentrations of paclitaxel. Top row: growth; middle row:balanced dormancy; bottom row:cellular dormancy. SB=100 µm. (B) Quantification of cell viability. * indicates p<0.05. n=5 z-stacks from 5 Individual hydrogels for each formulation. Values represent mean±standard deviation.

Figure 12:
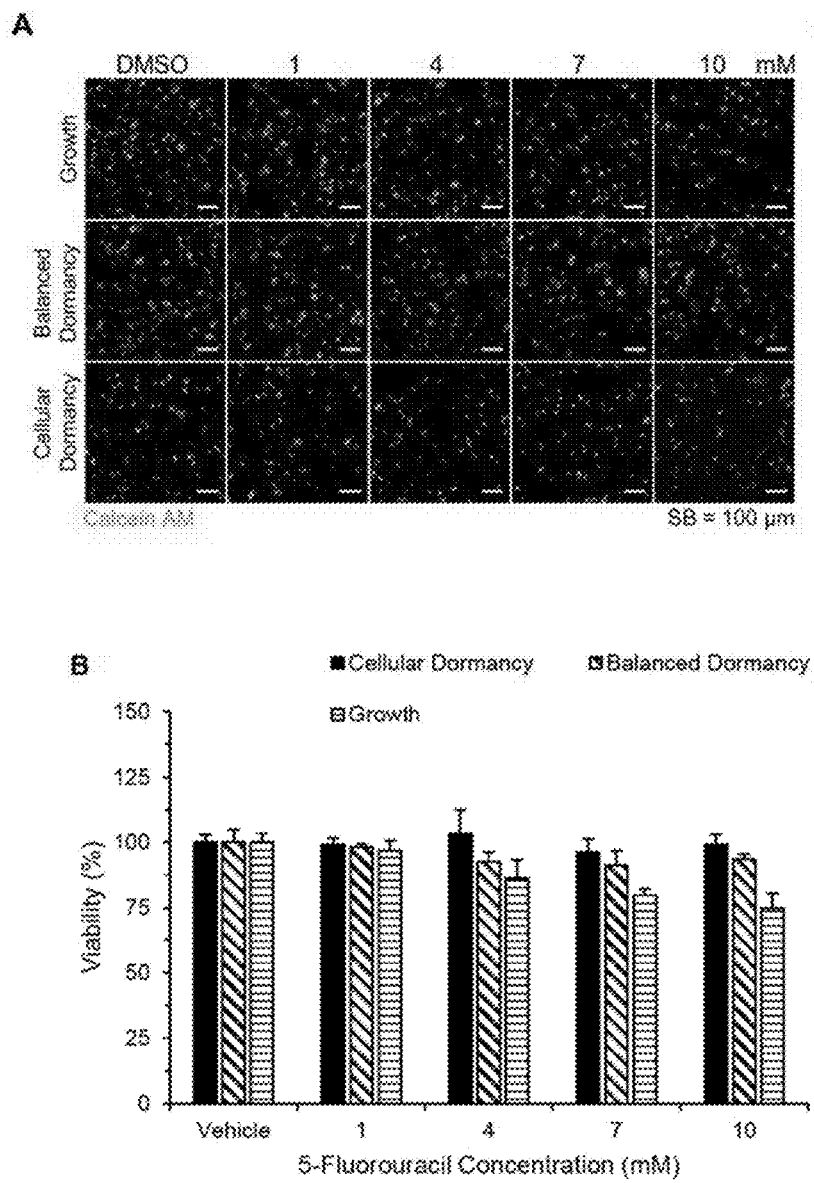

FIG. 12 displays response of MDA-MB-231s to 5-Fluorouracil as follows: (A) Representative maximum intensity z-projections of 3D image stacks of MDA-MB-231s fluorescently labeled with Calcein AM (live cells:green) after 48 hr exposure to a media+1% v/v DMSO vehicle control (DMSO) or varying concentrations of 5-Fluorouracil. Top row:growth; middle row:balanced dormancy; bottom row: cellular dormancy. SB=100 µm. (B) Quantification of cell viability. * indicates p<0.05. n=5 z-stacks from 5 individual hydrogels for each formulation. Values represent mean±standard deviation.

Figure 13:
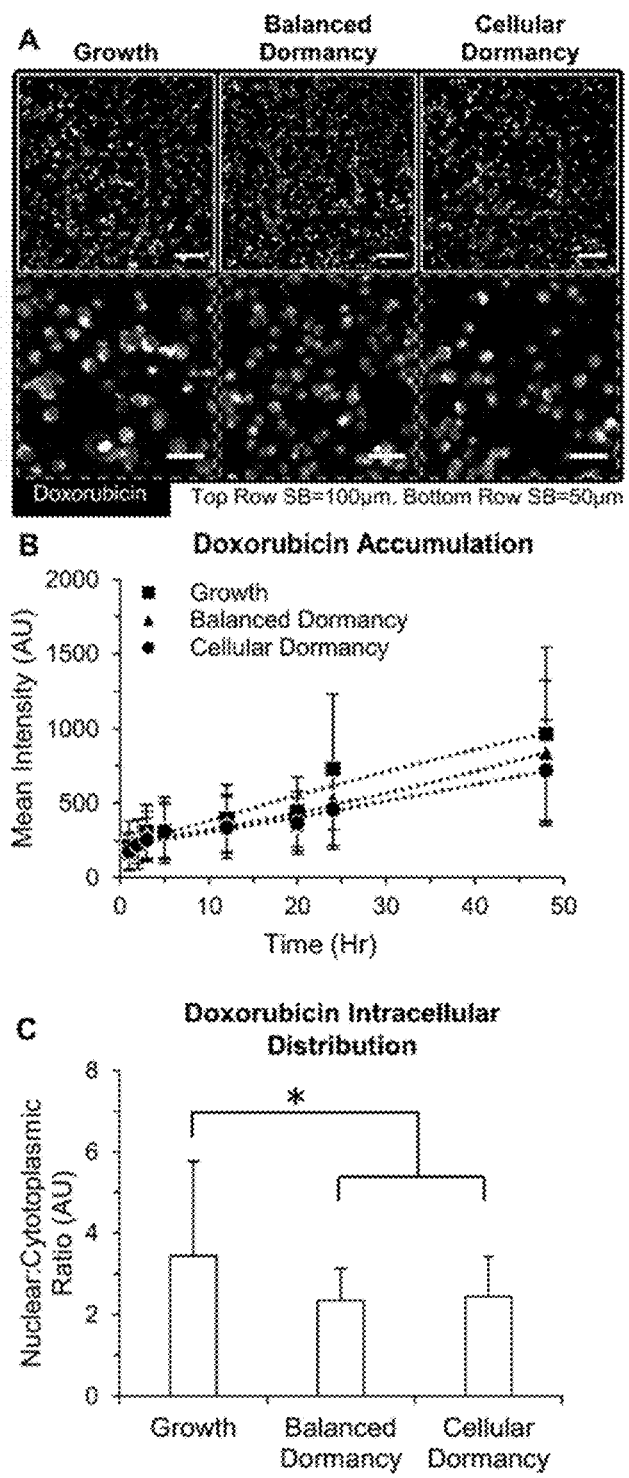

FIG. 13 displays doxorubicin accumulation & localization in MDA-MB-231 cells as follows: (A) Representative maximum intensity z-projections of 3D image stacks of doxorubicin (white) in MDA-MB-231s cultured in growth, balanced dormancy, or cellular dormancy states after 48 hr exposure to 0.05 mM doxorubicin. Green boxes in top row indicate zoomed in regions shown in bottom row. SB=100 µm (top row). SB-50 µm (bottom row). (B) Quantification of doxorubicin accumulation in MDA-MB-231s over 48 hr measured by mean fluoresce intensity for growth (black), balanced dormancy (red), and cellular dormancy (blue). (C) Ratio of nuclear to cytoplasmic localization of doxorubicin at 48 hr from fluorescence intensity measurements of the cell cytoplasm and nucleus. * indicates p<0.05. n=4 z-stacks from 4 Individual hydrogels for each formulation. Values represent mean±standard deviation.

Figure 14:
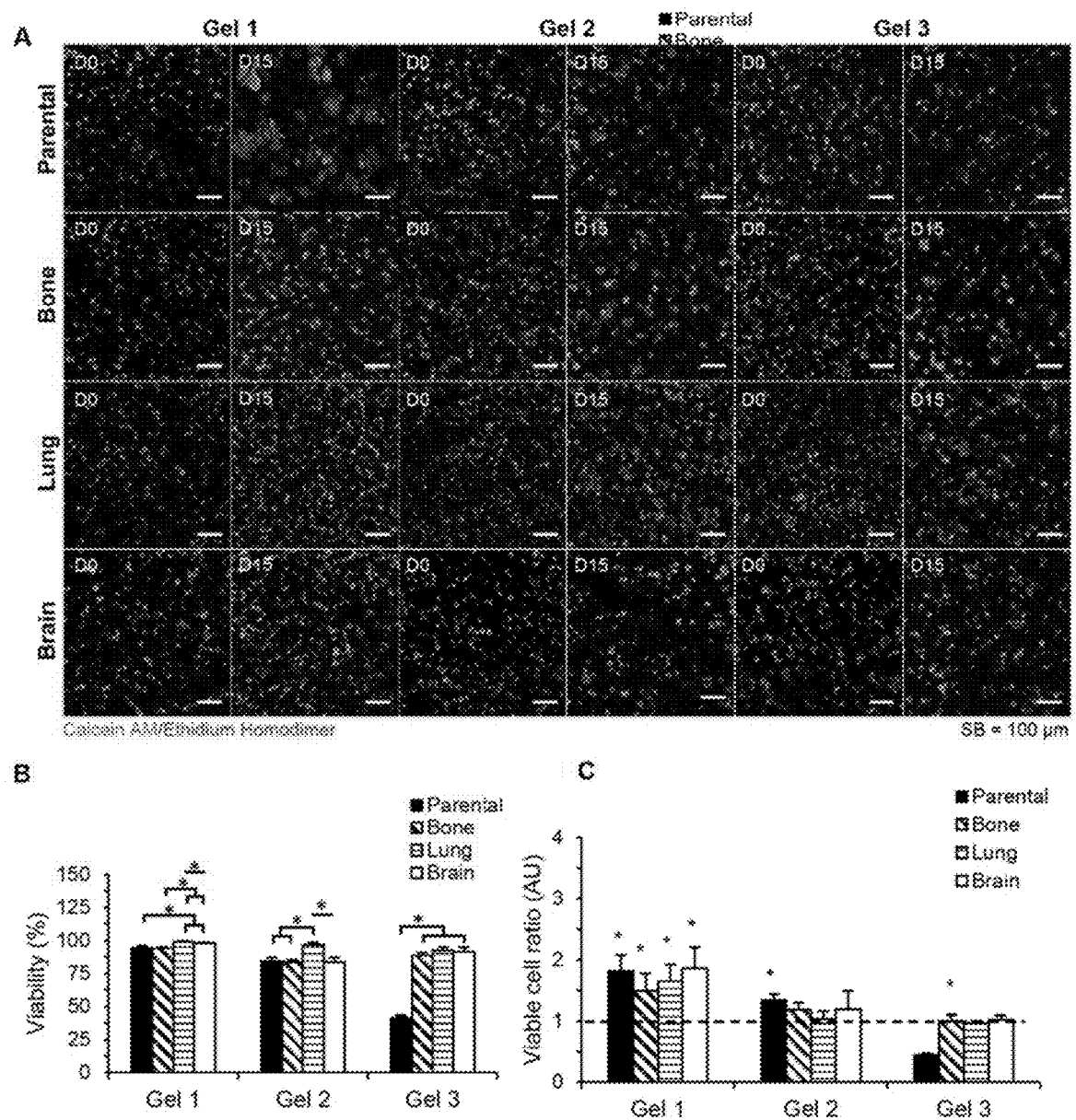

FIG. 14 shows displays cell viability. (A) Representative maximum intensity z-projections from 3D image stacks of MDA-MB-231s (parental), MDA 231-BoM-1833s (bone-metastatic), MDA 231-LM2-4175s (lung-metastatic), and MDA 231-BrM2-831s (brain-metastatic) after day 0 (6 hr post encapsulation) or day 15 in culture. Cells were labeled with calcein AM (green:live cells) and ethidium homodimer (red:dead cells). SB=100 µm. (B) Quantification of cell viability at day 15. (C) Quantification of viable cell ratio by normalizing day 15 to day 0 to determine the change in the number of viable cells. Red line indicates a ratio of 1 (no change in number of viable cells). * indicates statistically significant difference (p<0.05). n=5 z-stacks from 5 individual hydrogels. Values represent mean+standard deviation.

Figure 15:
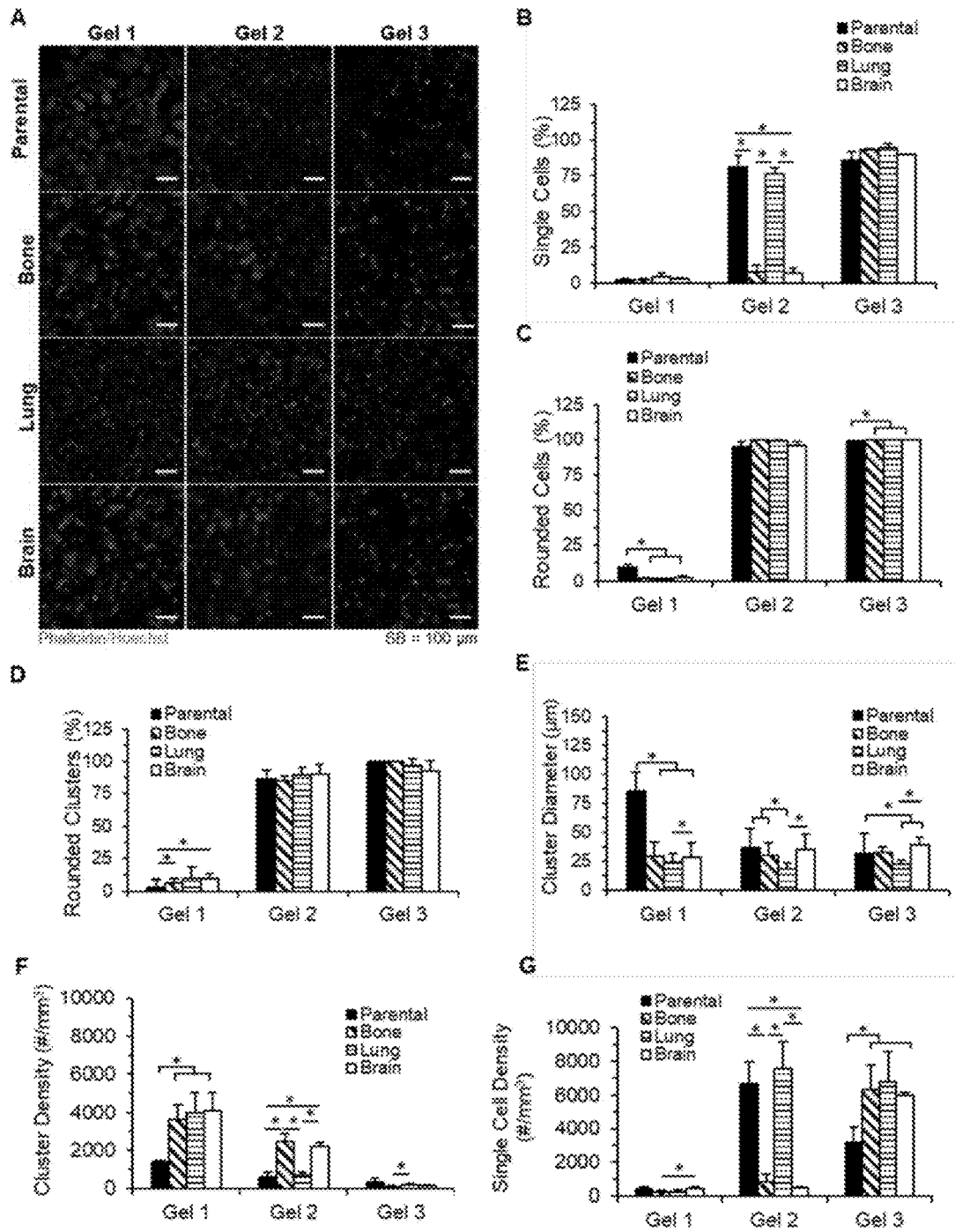

FIG. 15 displays analysis of the cell & cell cluster morphology. (A) Representative maximum intensity z-projections from 3D image stacks of MDA-MB-231s (parental), MDA 231-BoM-1833s (bone-metastatic), MDA 231-LM2-4175s (lung-metastatic), and MDA 231-BrM2-831s (brain-metastatic) after 15 days in culture. Cells were fluorescently labeled with phalloidin (red:F-actin) and Hoechst (blue: nuclei). SB=100 µm. Quantification of (B) percent of the population residing as individual, non-clustered cells, (C) single cell invasiveness, (D) duster cell invasiveness, (E) cluster diameter, (F) cluster density, and (G) single cell density at day 15. * indicates p<0.05. n=5 z-stacks from 5 individual hydrogels. Values represent mean+standard deviation.

Figure 16:
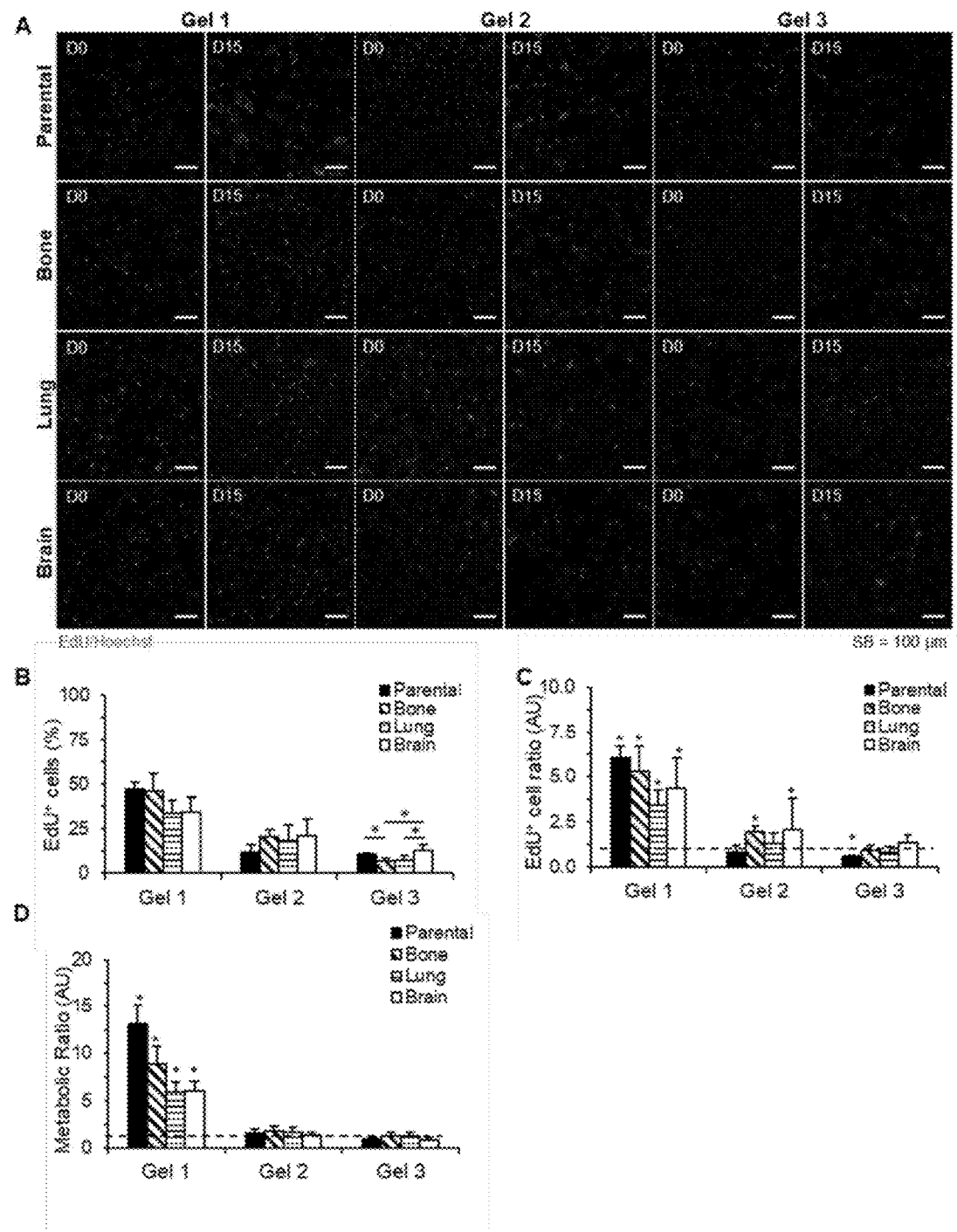

FIG. 16 displays cell proliferation and metabolism. (A) Representative maximum intensity z-projections from 3D image stacks of MDA-MB-231s (parental), MDA 231-BoM-1833s (bone-metastatic), MDA 231-LM2-4175s (lung-metastatic), and MDA 231-BrM2-831s (brain-metastatic) after day 0 (6 hr post encapsulation) or day 15 in culture. Cells were labeled with EdU (red) and counterstained with Hoechst (blue:nuclei). SB=100 µm. (B) Quantification of EdU+ cells at day 15. (C) Quantification of EdU+ cell ratio by normalizing the number of EdU+ cells at day 15 to day 0. Dashed red line indicates a ratio of 1. (D) Quantification of metabolic activity from an Alamar blue assay at day 15, normalized to day 0. Dashed red line Indicates a ratio of 1. * indicates p<0.05. n=5 z-stacks from 5 individual hydrogels. Values represent mean+standard deviation.

Figure 17:
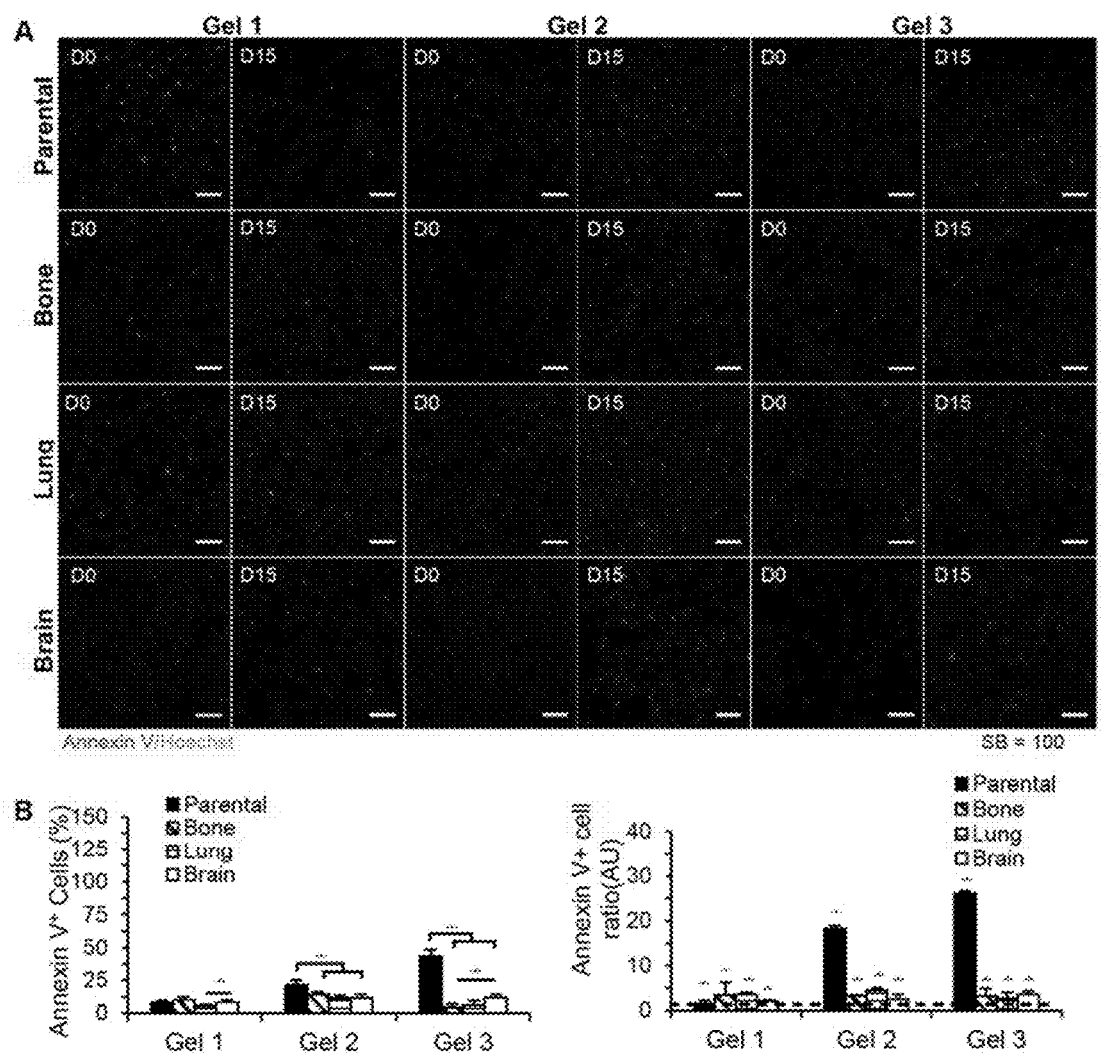

FIG. 17 displays early apoptosis. (A) Representative maximum intensity z-projections from 3D Image stacks of MDA-MB-231s (parental), MDA 231-BoM-1833s (bone-metastatic), MDA 231-LM2-4175s (lung-metastatic), and MDA 231-BrM2-831s (brain-metastatic) after day 0 (6 hr post encapsulation) or day 15 in culture. Cells were fluorescently labeled for the early apoptosis marker (Annexin V:red) and counterstained with Hoechst (blue:nuclei). SB=100 μm. (B) Quantification of Annexin V+ cells at day 15. (C) Quantification of Annexin V+ cell ratio by normalizing the number of Annexin V+ cells at day 15 to day 0. Dashed red line indicates a ratio of 1. * indicates p<0.05. n=5 z-stacks from 5 individual hydrogels. Values represent mean+standard deviation.

Figure 18:
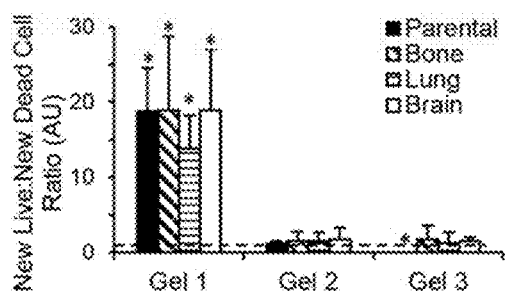
Figure 18:
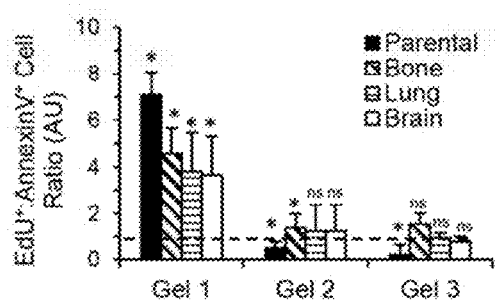

FIG. 18 displays quantification of cell survival and death. (A) Ratio of new live to new dead cells from days 0 and 15. Dashed red line indicates a ratio of 1. (B) Ratio of EdU+ cells to Annexin V+ cells at day 15. Dashed red line indicates a ratio of 1. * indicates statistical difference (p<0.05) between number of viable cells or EdU+:Annexin V+ cells at days 0 and 15. ns indicates no significant difference between new live and new dead cells. n=5 z-stacks from 5 individual hydrogels. Values represent mean+standard deviation.

Figure 19:
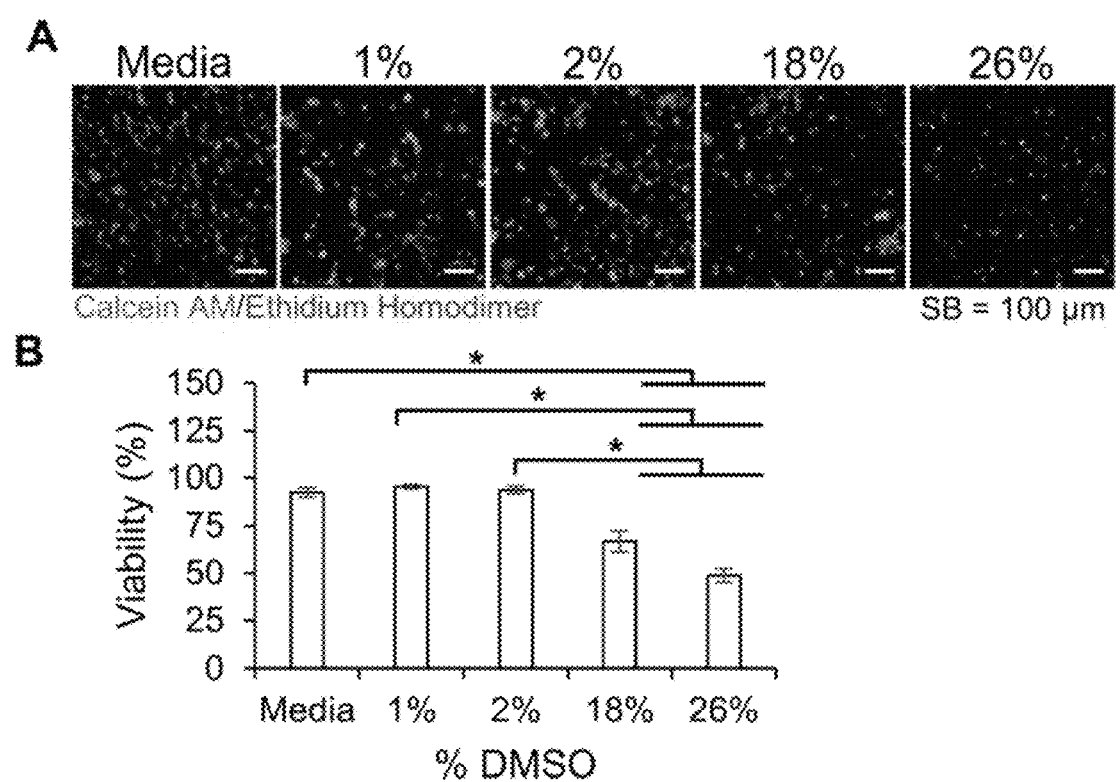

FIG. 19 displays influence of DMSO on cell viability for cells cultured in a growth hydrogel formulation. (A) Representative maximum intensity z-projections of 3D image stacks of encapsulated MDA-MB-231s after 48 hr exposure to varying concentrations (% v/v) of DMSO in serum-containing medium. Live cells are labeled with Calcein AM (green) and dead cells are labeled with Ethidium homodimer (red). SB=100 μm. (B) Quantification of cell viability. * indicates p<0.05. n=5 z-stacks from 5 individual hydrogels. Values represent mean±standard deviation.

DETAILED DESCRIPTION OF THE INVENTION

As used herein the term "cancer" is used interchangeably with the term "cell" and refers to any malignant and/or invasive growth or tumor caused by abnormal cell growth. As used herein "cancer" refers to solid tumors named for the type of cells that form them, cancer of blood, bone marrow, or the lymphatic system. Examples of solid tumors include but are not limited to sarcomas and carcinomas. Examples of cancers of the blood include but are not limited to leukemias, lymphomas and myeloma. The term "cancer" includes, but is not limited to, a primary cancer that originates at a specific site in the body, a metastatic cancer that has spread from the place in which it started to other parts of the body, a recurrence from the original primary cancer after remission, and a second primary cancer that is a new primary cancer in a person with a history of previous cancer of different type from latter one.

As used herein, the term "cell culture media" refers to a liquid mixture of two or more reagents as dissolved solid or liquid state that is contacted by cells of Interest and is necessary to maintain them for experimental purposes for the duration of the study. Any suitable cell culture medium can be used, including, but not limited to DMEM alone or DMEM supplemented with FBS and/or penicillin-streptomycin.

As used herein, the phrase "the state of the cancer cells is maintained in a first cancer state" refers to the morphological or phenotypic characteristics of cells that is initially desired within the hydrogels at the initiation of experimental studies.

As used herein, the phrase "the state of the cancer cells is switched from the first cancer state to a second state" means changes in the morphological or phenotypic characteristics of cells from the initial desired conditions at the initiation of experimental studies to a different set of characteristics as directed by changes caused in the hydrogel matrix.

As used herein, the terms "cancer state", "first cancer state", and "second cancer state" refers to a state of the cancer cells selected from the group consisting of invasive growth, single cell restricted survival dormancy, single cell balanced survival dormancy and tumor mass balanced survival dormancy.

As used herein the term "invasive growth" refers to a cancer state wherein the viable cell density on day 15 or later, for example, day 20, 50, 60 or 90, is statistically greater than day 0 value by, for example, at least 5%, 10%, 20%, 50%, 100%, 200%, 500% or 1000%, in the crosslinked PAG-based hydrogel composition of the present invention, statistical significance being measured using one-way ANOVA and a probability value <0.01 being considered statistically significant.

As used herein the term "single cell restricted survival dormancy" refers to a cancer state wherein the viable cell density on day 15 or later, for example, day 20, 50, 60 or 90, is equal to or less than day 0 value by, for example, at least 5%, 10%, 20%, 50%, 90%, 95% or 99%, and cell viability value on day 15 or later, for example, day 20, 50, 60 or 90, is less than, for example, 50%, 20%, 10%, 5% or 1%, of day 0 value in the crosslinked PAG-based hydrogel composition of the present invention, as measured using one-way ANOVA.

As used herein the term "single cell balanced survival dormancy" refers to a cancer state wherein the viable cell density on day 15 or later, for example, day 20, 50, 60 or 90, is equal to or less than day 0 value by, for example, at least 5%, 10%, 20%, 50%, 90%, 95% or 99%, and cell viability value on day 15 or later, for example, day 20, 50, 60 or 90, is within, for example, 20%, 10%, 5% or 1%, of day 0 value, and the percentage of single cells is greater than, for example, 70%, 80%, 90%, 95% or 99%, of the total cell population, and the percentage of clustered cells is less than, for example, 30%, 20%, 10%, 5% or 1%, of the total population of the cancer cells in the crosslinked PAG-based hydrogel of the present invention.

As used herein the term "tumor mass balanced survival dormancy" refers to a cancer state wherein the viable cell density on day 15 or later, for example, day 20, 50, 60 or 90, is equal to or less than day 0 value by, for example, at least 5%, 10%, 20%, 50%, 90%, 95% or 99%, and cell viability value on day 15 or later, for example, day 20, 50, 60 or 90, is within, for example, 20%, 10%, 5% or 1%, of day 0 value, and the percentage of clustered cells is greater than, for example, 50%, 60%, 70%, 80%, 90%, 95% or 99%, of the total cell population, and the percentage of single cells is less than, for example, 30%, 20%, 10%, 5% or 1%, of the total population of the cancer cells in the crosslinked PAG-based hydrogel of the present invention.

As used herein the term "hydrogel digesting agent" refers to any chemical or biological agent that when contacted with a PAG-based hydrogel results in dissociation or breakup of physical or chemical crosslinks in the polymer network of the PAG-based hydrogel, thereby leading to degradation of the hydrogel structure. Suitable chemical hydrogel digesting agents include, but are not limited to, sodium hydroxide, hydrogen peroxide. Suitable hydrogel digesting agents include, but are not limited to, collagenase(s), trypsin, chymotrypsin, elastase, proteinase-K, hyaluronidase, plasmin, papain, dispase, and combinations thereof.

As used herein the term "cell viability" refers to the number of live cancer cells as a percentage of the total number of cancer cells present in the crosslinked PAG-based hydrogel of the present invention.

As used herein the term "apoptosis/early apoptosis" refers to the number of cancer cells stained positively for Annexin V stain as a percentage of the total number of cancer cells present in the crosslinked PAG-based hydrogel of the present invention.

As used herein the term "proliferation" refers to the number of cancer cells incorporating 5-ethynyl-2'-deoxyuridine (EdU) In their DNA as a percentage of the total number of cancer cells present in the crosslinked PAG-based hydrogel of the present Invention.

As used herein the term "viable cell density" refers to the number of live cancer cells per unit volume of the crosslinked PAG-based hydrogel.

As used herein the term "metabolic activity" refers to the change in fluorescence of Alamar Blue reagent in contact with the system of the present invention comprising cancer cells in contact with a culture media and encapsulated in the crosslinked PAG-based hydrogel over time.

As used herein the term "single cells" refers to the cancer cells appearing as isolated cells, which are not in contact with the neighboring cells within a given hydrogel volume.

As used herein the term "clustered cells" refers to the cells appearing as a group of 2 or more cancer cells in dose contact with each other within a given hydrogel volume.

As used herein the term "rounded cells" refers to the single cells having a roundness value of 0.8 or higher.

As used herein the term "invasive cells" refers to the single cells having a roundness value of less than 0.8.

The present inventions discloses crosslinked hydrogel compositions, systems comprising a plurality of cancer cells in contact with a cell culture media and encapsulated in the crosslinked PAG-based hydrogel composition and methods of making such crosslinked hydrogel compositions and systems; and methods of using such compositions and systems for screening an agent for effectiveness of the agent against cancer cells. Also disclosed are kits comprising one or more components comprising one or more systems of the present SS disclosure and one or more instructions.

System

In an aspect of the present invention, there is provided a system comprising a crosslinked poly(alkylene glycol) (PAG)-based hydrogel composition, a cell culture media in contact with the crosslinked PAG-based hydrogel composition, and a plurality of cancer cells in contact with the cell culture media and encapsulated in the crosslinked PAG-based hydrogel composition.

In an embodiment, the system can comprise cancer cells selected from an established cell lines representing one of: breast cancer, ovarian cancer, prostate cancer, colorectal cancer, bone cancer, lung cancer, or brain cancer. The cancer cells can be derived from a tumor patient or through established lines. In an embodiment, the cancer cells can be selected from either patient-derived tumor cells or patient-derived xenografts.

In an embodiment, the crosslinked PAG-based hydrogel composition can be formed by photopolymerizing a polymer-peptide macromer in the presence of a Type 1 ultraviolet (UV) photoinitiator. In one embodiment, the polymer-peptide macromer comprises a first poly(alkylene glycol) covalently conjugated with a peptide comprising a sequence of X1-X2-X3-X4-X5-X6-X7-X8-X9-X10-X11, where each of the X1 to X11 is G, P, Q, W, I or K.

Suitable examples of the peptide include, but are not limited to GGGPQGIWGQGK (SEQ ID NO: 1), GGGIQQWGPGGK (SEQ ID NO: 2), GGGGGIPQQWGK (SEQ ID NO: 3) and combinations thereof.

Suitable Type I UV photoinitiators include, but are not limited to lithium phenyl-2,4,6-trimethyl benzoyl phosphinate (LAP), 1-[4-(2-Hydroxyethoxy)-phenyl]-2-hydroxy-2-methyl-1-propane-1-one (Irgacure® 2959), 2,2-Dimethoxy-2-phenylacetophenone (Irgacure® 651, DMPA), Bis(2,4,6-trimethylbenzoyl)-phenyl phosphine oxide (Irgacure® 819), Diphenyl(2,4,6-trimethylbenzoyl) phosphine oxide (Darocur).

In an embodiment, the system comprises a crosslinked PAG-based hydrogel composition formed by photopolymerizing the polymer-peptide macromer and a cell-adhesive macromer in the presence of the Type 1 ultraviolet (UV) photoinitiator, The cell-adhesive macromer of the present disclosure comprises a second poly(alkylene glycol) covalently conjugated with a cell-adhesive peptide.

Any suitable poly(alkylene glycol) (PAG), such as a poly(ethylene glycol) (PEG), can be used for the first and the second poly(alkylene glycol). In one embodiment, the PAG Is an acrylated poly(alkylene glycol), such as an acrylated poly (ethylene glycol). As used herein, the term "acrylated" includes both acrylated and methacrylated and the term "acrylate" includes both acrylate and methacrylate.

One terminal end of the poly(alkylene glycol) used to prepare the polymer-peptide macromer and/or the cell-adhesive macromer may be functionalized with an acrylate group while another terminal end may be functionalized with a group such as valerate, N-hydroxylsuccinimide, succinimidyl carboxymethyl ester, succinimidyl amido succinate, succinimidyl carbonate, succinimidyl succinate, succinimidyl carbonate, succinimidyl glutarate, or maleimide which is capable of reacting with a functional group (for example, an amino group —$NH_2$) on a peptide (to form a polymer-peptide macromer or a cell-adhesive macromer).

Suitable examples of PAGs include but are not limited to acrylate-poly(ethylene glycol)-succinimidyl valerate (PEG-SVA), acrylate-PEG-N-hydroxylsuccinimide (PEG-NHS), acrylate-PEG-succinimidyl carboxymethyl ester (PEG-SCM), acrylate-PEG-succinimidyl amido succinate (PEG-SAS), acrylate-PEG-succinimidyl carbonate (PEG-SC), acrylate-PEG-succinimidyl glutarate (PEG-SG), acrylate-PEG-succinimidyl succinate (PEG-SS) and acrylate-PEG-maleimide (PEG-MAL). In one embodiment the first and the second poly(alkylene glycol) are the same. In another embodiment, the first and the second poly(alkylene glycol) are different.

The PAG for use in the synthesis of the crosslinked hydrogels can have a number average molecular weight in the range of 2 to 20 kDa and can be dissolved in an aqueous buffered saline at a concentration range of 2-20% weight/volume for use in the formation of peptide macromer and/or cell-adhesive macromer.

Any suitable cell-adhesive peptide may be used including a peptide motif selected from the group consisting of RGDS (SEQ ID NO: 4), RDGS (SEQ ID NO: 5), RGES (SEQ ID NO: 6), REGS (SEQ ID NO: 7), IKVAV (SEQ ID NO: 8), VVIAK (SEQ ID NO: 9), YIGSR (SEQ ID NO: 10), YSRIG (SEQ ID NO: 11), DGEA (SEQ ID NO: 12), DAEG (SEQ ID NO: 13), and combinations thereof.

In one embodiment, the PAG is poly(ethylene glycol) and the cell-adhesive peptide is RGDS.

In yet another embodiment, the system further comprises the crosslinked PAG-based hydrogel composition formed by photopolymerizing the polymer-peptide macromer and optionally a co-monomer in the presence of the Type 1 ultraviolet (UV) photoinitiator. Suitable co-monomer includes but is not limited to n-vinyl pyrrolidone (NVP).

Other suitable co-monomers include other types of ethylenically unsaturated compounds containing at least one carbon-carbon double bond capable of participating in a photopolymerization involving ethylenically unsaturated functional groups, such as acrylate groups, on the polymer-peptide macromer and cell-adhesive macromer. Such carbon-carbon double bonds may be present in the co-monomer in the form of vinyl or acrylate groups, for example. According to certain embodiments of the Invention, a co-monomer or combination of co-monomers is used which, when homopolymerized, yields a water-soluble or water-swellable polymer.

Figure 1A:
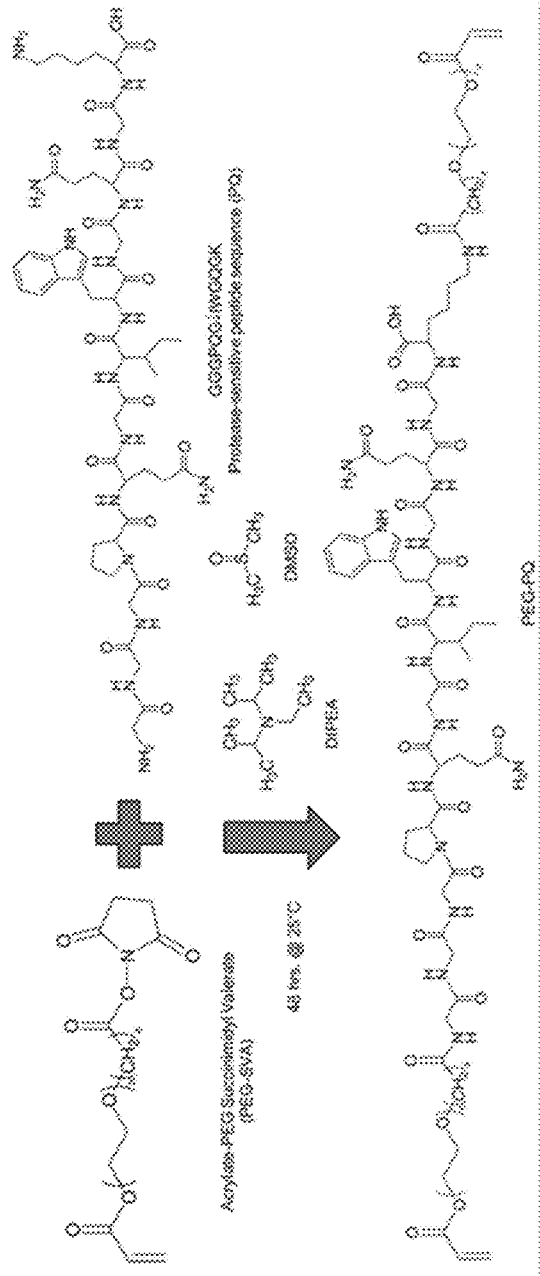
FIG. 1A displays an exemplary scheme of acrylate-PEG-SVA reacting with the matrix metalloproteinase cleavable peptide sequence, GGGPQGIWGQGK (PQ), to yield the PEG-PQ macromer consisting of the PQ sequence flanked by two PEG chains, each containing a terminal acrylate group.
Figure 1B:
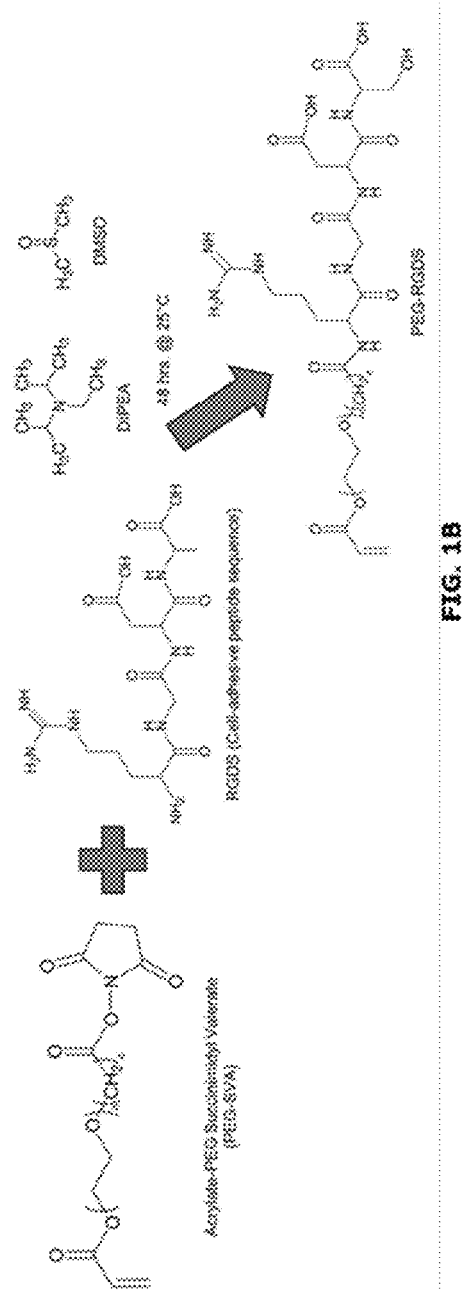
FIG. 1B displays another exemplary scheme of acrylate-PEG-SVA reacting with the integrin ligating peptide sequence, RGDS, to yield the PEG-RGDS macromer with one PEG chain and a terminal acrylate group.

In an embodiment of the system, the first and the second PAG are the same and comprises acrylate-PEG-SVA, the peptide is a proteolytically-degradable peptide comprising a motif: GGGPQGIWGQGK (SEQ ID NO: 1) and the polymer-peptide macromer is PEG-PQ, as shown in FIG. 1A. In particular, FIG. 1A displays an exemplary scheme of acrylate-PEG-SVA reacting with the matrix metalloproteinase cleavable peptide sequence, GGGPQGIWGQGK (PQ), to yield the PEG-PQ macromer consisting of the PQ sequence flanked by two PEG chains, each containing a terminal acrylate group. The system comprises RGDS as the cell-adhesive peptide. FIG. 1B displays an exemplary scheme of acrylate-PEG-SVA reacting with the integrin ligating peptide sequence, RGDS, to yield the PEG-RGDS macromer with one PEG chain with a terminal acrylate group.

Figure 1C:
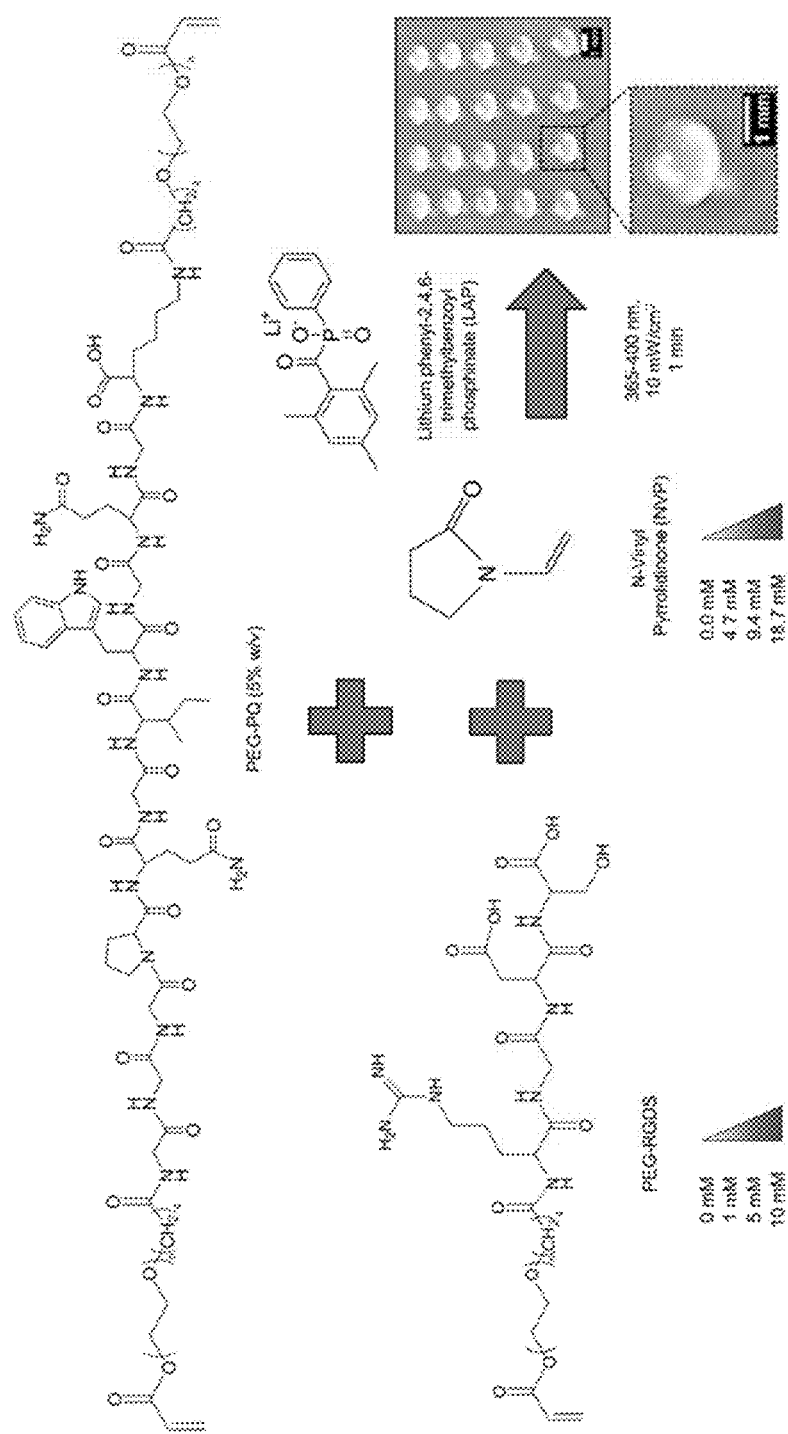
FIG. 1C displays an exemplary scheme of PEG-PQ (5% w/v) and PEG-RGDS (0-10 mM) photocrosslinked with the co-monomer n-vinyl pyrrolidinone (NVP) (0.0-18.7 mM) via photoinitiation of lithium phenyl-2,4,6-trimethylbenzoyl phosphinate (LAP) to generate hydrogels (Scale bar=1 mm). MDA-MB-231 cells were encapsulated at a density of 10 million cells/mL and the hydrogels transferred to wells containing cell culture media for 3D culture and subsequent analysis.

In yet another embodiment, the system comprises the crosslinked PAG-based hydrogel composition formed by photopolymerizing the polymer-peptide macromer, the cell-adhesive macromer and the co-monomer in the presence of the Type 1 ultraviolet (UV) photoinitiator. FIG. 1C displays an exemplary scheme of PEG-PQ and PEG-RGDS photo-crosslinking with the co-monomer n-vinyl pyrrolidinone (NVP) via photoinitiation of lithium phenyl-2,4,6-trimethylbenzoyl phosphinate (LAP) to generate 3 μL hydrogel droplets with a diameter of ~1.5 mm and height of ~1 mm (Scale bar=1 mm). MDA-MB-231 cells were encapsulated at a density of 10 million cells/mL and the hydrogels transferred to wells containing cell culture media for 3D culture and subsequent analysis.

The cross-linked hydrogels of the present invention may have a compressive modulus in the range of 5-30 kPa, as measured by application of a vertical minimum compressive force of 0.02 newtons (N) to a cylindrical hydrogel sample of 1 millimeters (mm) height and 3 mm diameter for a duration of 100 seconds (s) at a constant displacement rate of 2 micrometers/second (μm/s) between two parallel plates immersed in water or saline.

The cross-linked hydrogels of the present invention may have a theoretical mesh size in the range of 50-70 nm, as measured by the release of fluorescently-labeled dextran of molecular weight 150 kilodaltons (kDa) via diffusion from a hydrogel sample and estimated using the hindered solute diffusion in solvent-filled-pores model.

The cancer cells for use in the various embodiments of the present invention can be in any cancer state selected from the group consisting of Invasive growth, single cell restricted survival dormancy, single cell balanced survival dormancy and tumor mass balanced survival dormancy.

In another aspect of the invention, there is provided a method of regulating a state of cancer cells. As used here, the term "regulating" includes maintaining the cancer cells in their state or changing from a first cancer state to a second cancer state different from the first cancer state.

Method of Regulating a State of Cancer Cells

The method of regulating a state of cancer cells comprises providing a system as disclosed hereinabove adding a reactant to the system, and adjusting the concentration of a reactant, whereby the state of the cancer cells is either maintained in a first cancer state or switched from the first cancer state to a second cancer state. The reactant is selected from the group consisting of a co-monomer, a cell-adhesive macromer, a hydrogel digesting agent and combinations thereof. Each of the first and the second cancer state can be selected from the group consisting of invasive growth, single cell restricted survival dormancy, single cell balanced survival dormancy and tumor mass balanced survival dormancy, such that the first state is different from the second state.

In one embodiment of the method of regulating a state of the cancer cells, the step of providing a system further comprises providing:
  (i) a first system comprising the cancer cells in contact with the cell culture media and encapsulated in a first crosslinked PAG-based hydrogel composition, wherein the first crosslinked PAG-based hydrogel composition is formed by photopolymerizing a polymer-peptide macromer in the presence of a Type 1 ultraviolet (UV) photoinitiator, wherein the first state of the cancer cells in the first system is single cell restricted survival dormancy;
  (ii) a second system comprising the cancer cells in contact with the cell culture media and encapsulated in a second crosslinked PAG-based hydrogel composition, wherein the second crosslinked PAG-based hydrogel composition is formed by photopolymerizing the polymer-peptide macromer and a cell-adhesive macromer in the presence of the Type 1 ultraviolet (UV) photoinitiator;
  (iii) a third system comprising the cancer cells in contact with the cell culture media and encapsulated in a third crosslinked PAG-based hydrogel composition, wherein the third crosslinked PAG-based hydrogel composition is formed by photopolymerizing the polymer-peptide macromer and a co-monomer in the presence of the Type 1 ultraviolet (UV) photoinitiator, wherein the co-monomer comprises n-vinyl pyrrolidone (NVP); and/or
  (iv) a fourth system comprising the cancer cells in contact with the cell culture media and encapsulated in a fourth crosslinked PAG-based hydrogel composition, wherein the fourth crosslinked PAG-based hydrogel composition is formed by photopolymerizing the polymer-peptide macromer, the cell-adhesive macromer and the co-monomer in the presence of the Type 1 ultraviolet (UV) photoinitiator,
  wherein each of the four system regulates cancer cells in one of the cancer states selected from the group consisting of invasive growth, single cell restricted survival dormancy, single cell balanced survival dormancy and tumor mass balanced survival dormancy state.

In various embodiment, the step of adjusting the concentration of a reactant comprises photopolymerizing the reactant with the PAG-based crosslinked hydrogel in the presence of the Type 1 ultraviolet (UV) photoinitiator, thereby resulting in reactant covalently conjugating with the PAG-based crosslinked hydrogel. In one embodiment, the reactant used for adjusting the concentration is the same as used in the building blocks of the PAG-based crosslinked hydrogel—the polymer-peptide macromer, the cell-adhesive macromer and/or the co-monomer. In the other embodiment, the reactant used for adjusting the concentration is different from that used in the building blocks of the PAG-based crosslinked hydrogel—the polymer-peptide macromer, the cell-adhesive macromer and/or the co-monomer. For example, if the cell-adhesive macromer comprises PEG-RGDS, then the reactant could be RGDS, PEG-RGDS, a peptide other than RGDS as disclosed hereinabove, or a cell-adhesive macromer other than PEG-RGDS. Similarly, the reactant could be the NVP, the co-monomer used in the making of a crosslinked hydrogel of the present disclosure or a different co-monomer.

In one embodiment, the method further comprises a step of determining the state of the cancer cells through quantification of cell viability, proliferation and viable cell density. The step of determining the state of the cancer cells further comprises measuring the viable cell density of the cancer cells on day 0 and day 15 or later and determining the state of the cancer cell. The state is invasive growth, if the viable cell density on day 15 is statistically greater than that on day 0, and the state is single cell restricted survival dormancy, if the cell viability on day 15 is statistically equal to or less than as compared to day 0. The method also comprises evaluating a 3D cell/cluster morphology. The state is single cell balanced survival dormancy, if the percentage of single viable cells is greater than 80% of the total cell population and the percentage of clustered cells is less than 20% of the total population and the state is tumor mass balanced survival dormancy, if the percentage of 0.30 clustered cells is greater than 80% of the total cell population and the percentage of single viable cells is less than 20% of the total population.

Figure 3:
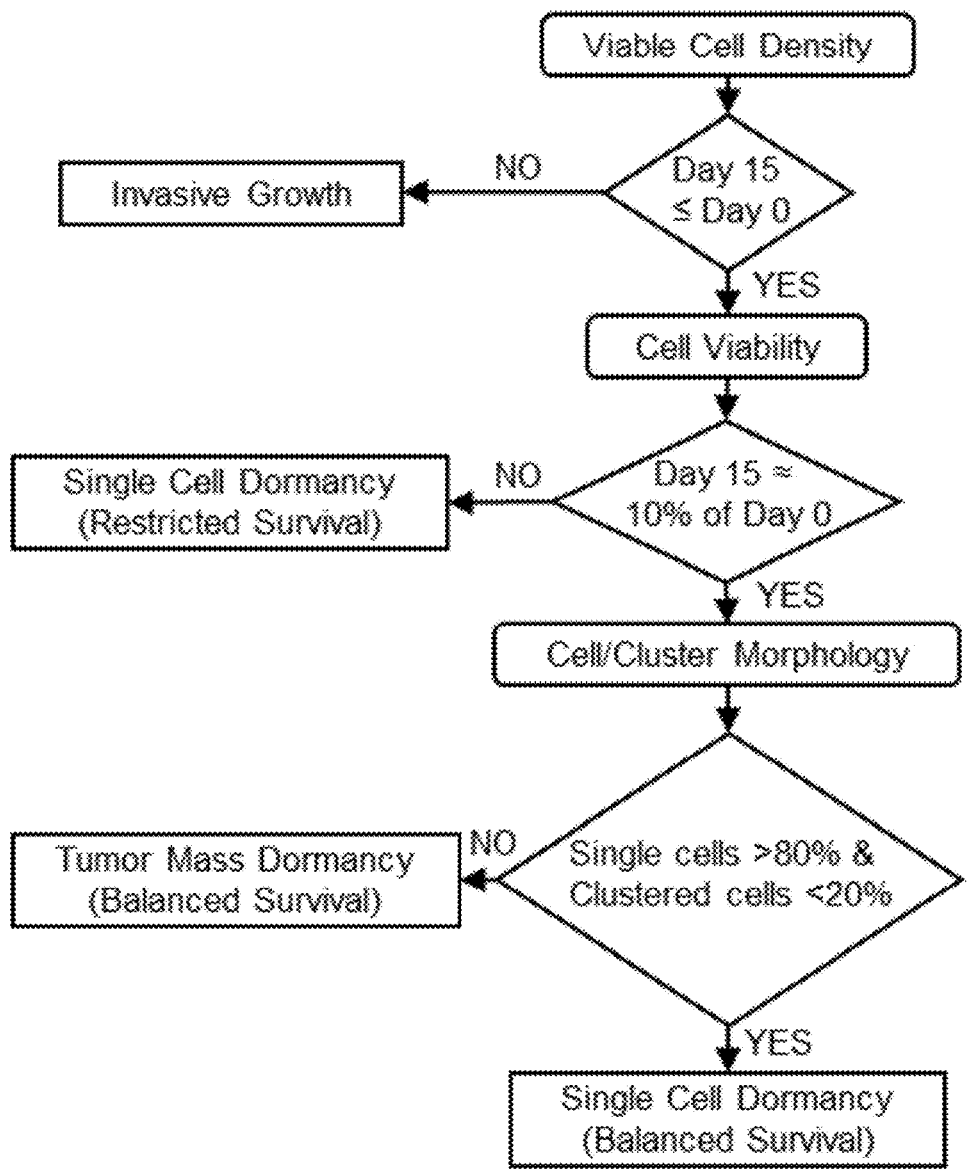
FIG. 3 shows an exemplary flowchart for determining/classifying cancer cell states induced by various crosslinked hydrogel compositions in accordance with various embodiments of the present invention. When viable cell density on day 15 is significantly greater than day 0, corresponding crosslinked hydrogel compositions are grouped into 'invasive growth' category. Remaining crosslinked hydrogel compositions are evaluated for cell viability. When cell viability on day 15 is less than 10% of corresponding day 0 values, crosslinked hydrogel compositions are grouped into 'single cell restricted survival dormancy' category. Remaining formulations are evaluated for 3D cell/cluster morphology.

FIG. 3 shows an exemplary flowchart for determining/classifying the state of the cancer cells induced by various crosslinked hydrogel compositions through quantification of cell viability, proliferation and viable cell density. As shown, when the viable cell density on day 15 is significantly greater than day 0, corresponding hydrogel compositions are grouped into 'Invasive growth' category. However, when the viable cell density on day 15 is significantly less than day 0, then the hydrogel compositions are evaluated for cell viability. If the cell viability on day 15 is found to be less than 10% of corresponding day 0 value, the hydrogel compositions are grouped into 'single cell restricted survival dormancy' category. However, if the cell viability on day 15 is found to be greater than 10% of corresponding day 0 value, then the hydrogel compositions are evaluated for 3D cell/cluster morphology and hydrogel compositions with single cells greater than 80% of total cell population and clustered cells less than 20% of total population are grouped into 'single cell balanced survival dormancy' category and the remaining hydrogel compositions are grouped into 'tumor mass balanced survival dormancy' category. Difference is considered statistically significant when p-value<0.01 (for viable cell density) and p-value<0.05 (cell viability), one-way ANOVA test; n=6 z-stacks from 3 hydrogels per condition.

In an embodiment, the step of providing a system further comprises forming the crosslinked PAG-based hydrogel composition by photopolymerizing the polymer-peptide macromer and the co-monomer, in the presence of the Type 1 ultraviolet (UV) photoinitiator. In an embodiment, the co-monomer comprises n-vinyl pyrrolidone (NVP) present in a concentration of 0-19 mM during photopolymerization (0-3 moles of comonomer per mole of polymer-peptide macromer). In such a system, free of cell-adhesive macromer, the first state of the cancer cells is single cell restricted survival dormancy.

In one embodiment, when the concentration of the co-monomer (e.g., NVP) during photopolymerization, is in the range of 0-5 mM and the reactant is the cell-adhesive macromer, then in such systems, the step of adjusting the concentration of a reactant comprises adjusting the concentration of cell-adhesive macromer disclosed hereinabove (e.g., PEG-RGDS) in the range of 0.01-20 mM to switch the state of the cancer cells to the invasive growth.

In another embodiment, when the concentration of the co-monomer (e.g., NVP) during photopolymerization, is in the range of 5-10 mM and the reactant is the cell-adhesive macromer, then in such systems, the step of adjusting the concentration of a reactant comprises adjusting the concentration of cell-adhesive macromer (e.g., PEG-RGDS) in the range of 5-20 mM to switch the state of the cancer cells from single cell restricted survival dormancy to the invasive growth.

In yet another embodiment, when the concentration of the co-monomer (e.g., NVP) during photopolymerization, is in the range of 0-10 mM and the reactant is the cell-adhesive macromer, then in such systems, the step of adjusting the concentration of a reactant comprises adjusting the concentration of cell-adhesive macromer (e.g., PEG-RGDS) in the range of 0.01-1 mM to switch the state of the cancer cells from single cell restricted survival dormancy to the single cell balanced survival dormancy. However, when the concentration of the cell-adhesive macromer is adjusted to be in the range of 5-20 mM, the state of the cancer cells is switched from the single cell balanced survival dormancy to the invasive growth.

In another embodiment, when the concentration of the co-monomer during photopolymerization, is in the range of 0-19 mM, the first state of the cancer cells encapsulated in the crosslinked hydrogel is single cell restricted survival dormancy. In such a system, when the concentration of cell-adhesive macromer is adjusted in the range of 1-20 mM and the reactant is the cell-adhesive macromer, then the state of the cancer cells is switched from the single cell restricted survival dormancy to the tumor mass balanced survival dormancy. However, the state of the cancer cells can be switched from the tumor mass balanced survival dormancy to the invasive growth upon addition of an effective amount of the hydrogel digesting agent as the reactant to the system.

Any suitable hydrogel digesting agent can be used, including but not limited to, collagenase I, collagenase IV, trypsin, proteinase-K, hyaluronidase, or combinations thereof.

Drug Screening

In an aspect, there is a method of screening an agent for effectiveness of the agent against cancer cells. The method comprises providing a system as disclosed hereinabove and determining the state of the cancer cells encapsulated in the crosslinked hydrogels, as disclosed hereinabove and shown in FIG. 3. The method further comprises adjusting the concentration of the one or more reactants, whereby the state of the cancer cells is maintained in the first cancer state selected from the group consisting of invasive growth, single cell balanced survival dormancy and tumor mass balanced survival dormancy. The method also comprises contacting the cancer cells with an effective amount of the agent selected from the group consisting of a drug, an antibody, and a biologic and monitoring the state of the cancer cells periodically from before (day 0) to after (for n days) the step of contacting the cancer cells, by measuring cell viability and viable cell density. The monitoring can be done for any number (n) of days, such as years, months, days. In some embodiments, the monitoring can be done for "n" number of days with n can be in the range of 1-90 or 1-60 or 1-50 or 1-20 or 1-15, or 1-10, or 1-5 or 1-3. In another embodiment, the monitoring can be done for "n" number of days with n can be 3, 5, 10, 15, 20, 25, 30, 35, 40, 45, 50, 55, 60, 65, 70, 75, 80, 85 or 90. The method further comprises assessing the efficacy of the agent on the cancer cells by comparing cell viability and viable cell density on day 0 with that on day n. In an embodiment, the step of assessing the efficacy of the agent on the plurality of cells comprises fluorescence staining the cancer cells with calcein AM and ethidium homodimer and fluorescence imaging to quantify % live and % dead cancer cells.

FIG. 4 shows a flow chart for drug screening using systems of the present disclosure. As shown, cancer cells can be encapsulated in various crosslinked hydrogel compositions and maintained in the system for n days with n=15 days. Cellular phenotypic metrics are evaluated on days 0, 5, 10 and 15, and relevant cell states are determined and verified. Subsequently, three possible routes for screening can be followed. In route 1, hydrogels supporting invasive growth state are contacted with therapeutic agent(s) and treatment efficacy against invasive cancers is assessed via quantification of viability and viable cell density to determine efficacy. In route 2, hydrogels inducing single cell restricted survival dormancy, single cell balanced survival dormancy and tumor mass balanced survival dormancy are contacted with therapeutic agent(s) and treatment efficacy against tumor dormancy is assessed via quantification of viability and viable cell density. In route 3, hydrogels inducing single cell restricted survival dormancy are crosslinked further with acrylate-PEG-peptide(s) (cell-adhesive peptide sequence) to induce dormancy-proliferation switch. The relapsed cells are contacted with therapeutic agent(s) and treatment efficacy against relapsed cancers is assessed via quantification of viability and viable cell density.

In another aspect, the method of screening an agent comprises adjusting the concentration of the one or more reactants, whereby the state of the cancer cells is switched from the first cancer state to a second state and contacting the cancer cells with an effective amount of the drug selected from the group consisting of a drug, an antibody, and a biologic. The method further comprises monitoring the state of the cancer cells 0.30 periodically from before (day 0) to after (for n days with n being from 1-90 or 1-60 or 1-50 or 1-20 or 1-15) the step of contacting the cancer cells, by measuring cell viability and viable cell density; and assessing the efficacy of the agent on the cells by comparing measured cell viability and viable cell density on day 0 with that on day n.

In yet another aspect, the method of screening an agent further comprises providing four systems as disclosed hereinabove, such that each system comprises cancer cells in one of the four cancer states. The method also comprises adjusting the concentration of the one or more reactants in at least one of the four systems, whereby the state of the cancer cells is maintained in the first cancer state selected from the group consisting of invasive growth, single cell balanced survival dormancy and tumor mass balanced survival dormancy and contacting the cancer cells in at least one of the four systems, with an effective amount of the agent selected from the group consisting of a drug, an antibody, and a biologic. The method further comprises monitoring the state of the cancer cells in at least one of the four systems, periodically from before (day 0) to after (for n days with n being from 1-90 or 1-60 or 1-50 or 1-20 or 1-15) the step of contacting the cancer cells, by measuring cell viability and viable cell density; and assessing an efficacy of the agent on the cancer cells by comparing cell viability and viable cell density on day 0 with that on day n from one system with at least another of the four systems.

In an embodiment, the agent comprises one or more conventional chemotherapeutic drugs; one or more new agents; or a combination thereof. Any suitable one or more conventional chemotherapeutic drugs can be used, including but not limited to Navelbine (vinorelbine), Platinol (cisplatin), Yervoy (ipilimumab), Gilotrif (afatinib), Sprycel (dasatinib), cediranib, Avastin (bevacizumab), PX-866, selumetinib, dalantercept, trebananib, doxorubicin (DOX), paclitaxel (PAC), and 5-fluorouracil (5-FU).

An important step toward preventing and treating cancer metastasis and recurrence includes forming a better understanding of various factors inducing and mediating cancer latency and dormancy and mechanisms of chemoresistance imparted on dormant cells. A significant roadblock in preventing cancer metastasis is that many current chemotherapeutics fail to effectively treat dormant cells.

In an embodiment of the present invention, three engineered hydrogels (one for each phenotypic state) were used to quantify the drug response of dormant cells. While other methods can be used to induce dormant states in cancer cells, exemplary embodiments of the present invention focuses on matrix-induced dormancy, as disclosed 0.30 hereinbelow in Example 13.

It is well-established that metastases originating from many types of primary cancer (breast, lung, prostate, etc.) undergo periods or latency or dormancy and whose length depends on a multitude of factors including origin, receptor status, and microenvironmental properties of the secondary organ infiltrated. It is also well-established that dormant DTCs in secondary organs often display enhanced chemoresistance. Since metastasis is one of the leading causes of cancer-associated morbidity and mortality there is an urgent need for simple platforms that allow for thorough investigations of how dormancy is induced and maintained. Such platforms could be beneficial in developing and testing new therapeutic strategies targeted at eliminating dormant cancer cells or preventing dormant cells from escaping dormancy. Although cancer dormancy can be induced in animal models and dormant cells isolated, implementation of these models for drug discovery can be cumbersome due to the difficulty in monitoring their response over time due to resolution limitations of current in vivo imaging modalities. Accordingly, in vitro platforms could potentially accelerate therapeutic development assuming that the cellular responses induced by these platforms are biomimetic enough to recapitulate important aspects of what occurs in vivo. Toward this goal, various embodiments of the present invention demonstrates the ability to induce growth, cellular dormancy, or balanced dormancy states in the triple negative MDA-MB-231 cell line via measurement of gross cell behavior and phenotypic classification. Since it is well-established that dormant cancer cells often display chemoresistance, various exemplary embodiments of the present invention disclosed hereinbelow further validates that the simple hydrogel platform of the present invention can be used to induce dormant states in metastatic breast cancer with increased chemoresistance. Such a platform potentially provides the ability to better understand how dormancy is initiated, the mechanisms of chemoresistance used by dormant cells, and the ability to screen new therapeutics. While a multitude of factors can induce dormancy, this platform focuses solely on the influence of matrix properties with respect to ligand density and degradability. While the influence of other dormancy inducing factors including immune responses, hypoxia, nutrient deprivation, soluble factors, and secondary cell signaling were excluded in the exemplary embodiments of the present invention, they could potentially be included in future studies although additional complexity needs to be carried out in a well-controlled, well-characterized, and thorough manner to understand their synergistic roles in influencing the observed cancer cell response. Similarly, although embodiments of the present are exemplified exclusively on triple negative breast cancer which has a relatively short latency period, it is believed that other breast cancers with different receptor statuses (e.g. ER+/PR+, HER2+) or cancers originating from different primary tumor sites (lung, prostate, etc.) could be induced to undergo dormancy.

Kits for Screening an Agent Against Cancer Cells

In an aspect of the invention, there is a kit comprising a first component comprising a system comprising a plurality of cancer cells in contact with the cell culture media and encapsulated in a crosslinked poly(alkylene glycol) (PAG)-based hydrogel composition, as disclosed hereinabove and a second component comprising an instruction for regulating the state of the cancer cells as disclosed hereinabove.

In an embodiment, the kit further comprises a third component comprising a co-monomer, e.g. NVP. In another embodiment, the kit also comprises a fourth component comprising a cell-adhesive macromer, as disclosed hereinabove, e.g., PEG-RGDS. In yet another embodiment, the kit further comprises a fifth component comprising a hydrogel digesting agent, as disclosed hereinabove. In another embodiment, the second component may further comprise an instruction for screening an agent for effectiveness of the agent against cancer cells, as disclosed hereinabove.

In another aspect, there is a kit comprising a first component comprising a precursor hydrogel composition comprising a polymer-peptide macromer (e.g., PEG-PQ) and a Type I photoinitiator and a second component comprising an instruction for making the crosslinked PAG-based hydrogel as disclosed hereinabove. The kit may further comprise a third component comprising a co-monomer, a fourth component comprising a cell-adhesive macromer, and instructions for making the crosslinked PAG-based hydrogel, as disclosed hereinabove. The kit may further comprise a fifth component comprising a hydrogel digesting agent, a sixth component comprising a plurality of cancer cells in contact with a cell culture media, and instruction for screening an agent for effectiveness of the agent against cancer cells, as disclosed hereinabove.

Aspects of the Invention

Certain illustrative, non-limiting aspects of the invention may be summarized as follows:

Aspect 1: A method of regulating a state of cancer cells, the method comprising:
  i) providing a system comprising:
    a) a crosslinked poly(alkylene glycol) (PAG)-based hydrogel composition,
    b) a cell culture media in contact with the crosslinked PAG-based hydrogel composition, and
    c) a plurality of cancer cells in contact with the cell culture media and encapsulated in the crosslinked PAG-based hydrogel composition;
  ii) adding a reactant to the system, wherein the reactant is selected from the group consisting of a co-monomer, a cell-adhesive macromer, a hydrogel digesting agent and combinations thereof; and
  iii) adjusting a concentration of the reactant in the system, whereby the state of the cancer cells is either maintained in a first cancer state or switched from the first cancer state to a second state,
  wherein the reactant is selected from the group consisting of a co-monomer, a cell-adhesive macromer, a hydrogel digesting agent and combinations thereof, and
  wherein each of the first and the second cancer state is selected from the group consisting of invasive growth, single cell restricted survival dormancy, single cell balanced survival dormancy and tumor mass balanced survival dormancy, such that the first state is different from the second state.

Aspect 2: The method according to aspect 1, wherein the step of providing a system further comprises forming the crosslinked PAG-based hydrogel composition by photopolymerizing a polymer-peptide macromer in the presence of a Type 1 ultraviolet (UV) photoinitiator,
  wherein the polymer-peptide macromer comprises a first poly(alkylene glycol) covalently conjugated with a peptide comprising a sequence of X1-X2-X3-X4-X5-X6-X7-X8-X9-X10-X11, wherein each of the X1 to X11 is G, P, Q, W, I or K.

Aspect 3: The method according to aspect 2, wherein the peptide is selected from the group consisting of GGGPQGIWGQGK (SEQ ID NO: 1), GGGIQQWGPGGK (SEQ ID NO: 2), GGGG-GIPQQWGK (SEQ ID NO: 3) and combinations thereof.

Aspect 4: The method according to aspect 2, wherein the first state is single cell restricted survival dormancy.

Aspect 5: The method according to according to any of aspects 1-4, wherein the cancer cells are selected from an established cell line representing one of: breast cancer, ovarian cancer, prostate cancer, colorectal cancer, bone cancer, lung cancer, or brain cancer.

Aspect 6: The method according to any of aspects 1-5, wherein the cancer cells are derived from a tumor patient and are either patient-derived tumor cells or patient-derived xenografts.

Aspect 7: The method according to aspect 1, wherein the step of providing a system further comprises forming the crosslinked PAG-based hydrogel composition by photopolymerizing the polymer-peptide macromer and the cell-adhesive macromer in the presence of the Type 1 ultraviolet (UV) photoinitiator,
  wherein the cell-adhesive macromer comprises a second poly(alkylene glycol) covalently conjugated with a cell-adhesive peptide comprising a peptide motif selected from the group consisting of RGDS (SEQ ID NO: 4), RDGS (SEQ ID NO: 5), RGES (SEQ ID NO: 6), REGS (SEQ ID NO: 7), IKVAV (SEQ ID NO: 8), VVIAK (SEQ ID NO: 9), YIGSR (SEQ ID NO: 10), YSRIG (SEQ ID NO: 11), DGEA (SEQ ID NO: 12), DAEG (SEQ ID NO: 13), and combinations thereof.

Aspect 8: The method according to aspect 7, wherein each of the first and the second poly(alkylene glycol) is independently selected from the group consisting of acrylate-PEG-succinimidyl valerate (PEG-SVA), acrylate-PEG-N-hydroxylsuccinimide (PEG-NHS), acrylate-PEG-succinimidyl carboxymethyl ester (PEG-SCM), acrylate-PEG-succinimidyl amido succinate (PEG-SAS), acrylate-PEG-succinimidyl carbonate (PEG-SC), acrylate-PEG-succinimidyl glutarate (PEG- SG), acrylate-PEG-succinimidyl succinate (PEG-SS) and acrylate-PEG-maleimide (PEG-MAL).

Aspect 9: The method according to aspect 1, wherein the step of providing a system further comprises forming the crosslinked PAG-based hydrogel composition by photopolymerizing the polymer-peptide macromer and optionally the co-monomer in the presence of the Type 1 ultraviolet (UV) photoinitiator, wherein the co-monomer comprises n-vinyl pyrrolidone (NVP).

Aspect 10: The method according to aspect 1, wherein the step of providing a system further comprises forming the crosslinked PAG-based hydrogel composition by photopolymerizing the polymer-peptide macromer, the cell-adhesive macromer and the co-monomer in the presence of the Type 1 ultraviolet (UV) photoinitiator.

Aspect 11: The method according to aspect 1, wherein the step of providing a system further comprises providing:
(i) a first system comprising the cancer cells in contact with the cell culture media and encapsulated in a first crosslinked PAG-based hydrogel composition formed by photopolymerizing a polymer-peptide macromer in the presence of a Type 1 ultraviolet (UV) photoinitiator, wherein the first state of the cancer cells in the first system is single cell restricted survival dormancy;
(ii) a second system comprising the cancer cells in contact with the cell culture media and encapsulated in a second crosslinked PAG-based hydrogel composition formed by photopolymerizing the polymer-peptide macromer and a cell-adhesive macromer in the presence of the Type 1 ultraviolet (UV) photoinitiator;
(iii) a third system comprising the cancer cells in contact with the cell culture media and encapsulated in a third crosslinked PAG-based hydrogel composition by photopolymerizing the polymer-peptide macromer and a co-monomer in the presence of the Type 1 ultraviolet (UV) photoinitiator, wherein the co-monomer comprises n-vinyl pyrrolidone (NVP); and/or
(iv) a fourth system comprising the cancer cells in contact with the cell culture media and encapsulated in a fourth crosslinked PAG-based hydrogel composition by photopolymerizing the polymer-peptide macromer, the cell-adhesive macromer and the co-monomer in the presence of the Type 1 ultraviolet (UV) photoinitiator,
wherein each of the four systems regulates cancer cells in one of the cancer states selected from the group consisting of invasive growth, single cell restricted survival dormancy, single cell balanced survival dormancy and tumor mass balanced survival dormancy state.

Aspect 12: The method according to aspect 1, wherein the step of adjusting the concentration of a reactant comprises photopolymerizing the reactant with the PAG-based crosslinked hydrogel in the presence of the Type 1 ultraviolet (UV) photoinitiator.

Aspect 13: The method according to any of aspects 1-12, further comprising a step of determining the state of the cancer cells through quantification of cell viability, proliferation and viable cell density.

Aspect 14: The method according to aspect 13, wherein the step of determining the state of the cancer cell further comprises:
(i) measuring the viable cell density of the cancer cells on day 0 and day 15 or later;
(ii) determining the state of the cancer cell,
a. wherein the state is invasive growth, if the viable cell density on day 15 or later is statistically greater than that on day 0, and
b. wherein the state is single cell restricted survival dormancy, if the cell viability on day 15 or later is statistically equal to or less than as compared to day 0; and
(iii) evaluating a 3D cell/cluster morphology,
wherein the state is single cell balanced survival dormancy, if the percentage of single viable cells is greater than 80% of the total cell population and the percentage of clustered cells is less than 20% of the total population; and
wherein the state is tumor mass balanced survival dormancy, if the percentage of clustered cells is greater than 80% of the total cell population and the percentage of single viable cells is less than 20% of the total population.

Aspect 15: The method according to aspect 9, wherein the concentration of the co-monomer in the system is in the range of 0-19 mM, and wherein the first state of the cancer cells is single cell restricted survival dormancy.

Aspect 16: The method according to aspect 15, wherein the concentration of the co-monomer is in the range of 0-5 mM, wherein the reactant is the cell-adhesive macromer, and
wherein the step of adjusting a concentration of the reactant in the system comprises adjusting the concentration of the cell-adhesive macromer in the range of 0.01-20 mM to switch the state of the cancer cells to the invasive growth.

Aspect 17: The method according to aspect 15 wherein the concentration of the co-monomer is in the range of 5-10 mM, wherein the reactant is the cell-adhesive macromer, and
wherein the step of adjusting the concentration of a reactant comprises adjusting the concentration of the cell-adhesive macromer in the range of 5-20 mM to switch the state of the cancer cells to the invasive growth.

Aspect 18: The method according to aspect 15 wherein the concentration of the co-monomer in the system is in the range of 0-10 mM, wherein the reactant is the cell-adhesive macromer, and
wherein the step of adjusting a concentration of the reactant in the system comprises adjusting the concentration of the cell-adhesive macromer in the range of 0.01-1 mM to switch the state of the cancer cells to the single cell balanced survival dormancy.

Aspect 19: The method according to aspect 18 wherein the step of adjusting a concentration of the reactant comprises adjusting the concentration of the cell-adhesive macromer in the range of 5-20 mM to switch the state of the cancer cells to the invasive growth.

Aspect 20: The method according to aspect 15 wherein the concentration of the co-monomer in the system is in the range of 0-19 mM, and wherein the first state of the cancer cells is single cell restricted survival dormancy.

Aspect 21: The method according to aspect 20, wherein the reactant is the cell-adhesive macromer, and wherein the step of adjusting a concentration of the reactant comprises adjusting the concentration of the cell-adhesive macromer in the range of 1-20 mM to switch the state of the cancer cells to the tumor mass balanced survival dormancy.

Aspect 22: The method according to aspect 21, further comprising adding the hydrogel digesting agent as the reactant, and wherein the step of adjusting a concentration of the reactant comprises adding to the system an effective amount of the hydrogel digesting agent to switch the state of the cancer cells to the invasive growth.

Aspect 23: The method according to aspect 22 wherein the hydrogel digesting agent comprises collagenase 1, collagenase IV, trypsin, proteinase-K, hyaluronidase, or combinations thereof.

Aspect 24: The method according to any of aspects 1-23 further comprising of screening an agent for effectiveness of the agent against cancer cells.

Aspect 25: The method according to aspect 24 wherein the step of screening an agent further comprises:
  i) adjusting the concentration of the one or more reactants, whereby the state of the cancer cells is maintained in the first cancer state selected from the group consisting of invasive growth, single cell balanced survival dormancy and tumor mass balanced survival dormancy;
  ii) contacting the cancer cells with an effective amount of the agent selected from the group consisting of a drug, an antibody, and a biologic;
  iii) monitoring the state of the cancer cells periodically from before (day 0) to after (for n days with n being from 1-90 or 1-60 or 1-50 or 1-20 or 1-15) the step of contacting the cancer cells, by measuring cell viability and viable cell density; and
  iv) assessing an efficacy of the agent on the cancer cells by comparing cell viability and viable cell density on day 0 with that on day n.

Aspect 26: The method according to aspect 25 wherein the step of assessing the efficacy of the agent on the plurality of cells comprises fluorescence staining the cancer cells with calcein AM and ethidium homodimer and fluorescence imaging to quantify % live and % dead cancer cells.

Aspect 27: The method according to claim 24 wherein the step of screening an agent further comprises:
  i) adjusting the concentration of the one or more reactants, whereby the state of the cancer cells is switched from the first cancer state to the second state;
  ii) contacting the cancer cells with an effective amount of the drug selected from the group consisting of a drug, an antibody, and a biologic;
  iii) monitoring the state of the cancer cells periodically from before (day 0) to after (for n days with n being from 1-90 or 1-60 or 1-50 or 1-20 or 1-15) the step of contacting the cancer cells, by measuring cell viability and viable cell density; and
  iv) assessing the efficacy of the agent on the cells by comparing measured cell viability and viable cell density on day 0 with that on day n.

Aspect 28: The method according to aspect 27 wherein the step of assessing the efficacy of the agent on the plurality of cells comprises fluorescence staining the encapsulated cancer cells with calcein AM and ethidium homodimer and fluorescence imaging to quantify % live and % dead cancer cells.

Aspect 29: The method according to aspect 24 wherein the step of screening an agent further comprises:
  i) providing four systems, such that each system comprises cancer cells in one of the four cancer states;
  ii) adjusting the concentration of the one or more reactants in at least one of the four systems, whereby the state of the cancer cells is maintained in the first cancer state selected from the group consisting of invasive growth, single cell balanced survival dormancy and tumor mass balanced survival dormancy;
  iii) contacting the cancer cells in at least one of the four systems, with an effective amount of the agent selected from the group consisting of a drug, an antibody, and a biologic;
  iv) monitoring the state of the cancer cells in at least one of the four systems, periodically from before (day 0) to after (for n days with n being from 1-90 or 1-60 or 1-50 or 1-20 or 1-15) the step of contacting the cancer cells, by measuring cell viability and viable cell density; and
  v) assessing the efficacy of the agent on the cancer cells by comparing cell viability and viable cell density on day 0 with that on day n from one system with at least another of the four systems.

Aspect 30: The method according to aspect 29 wherein the step of assessing the efficacy of the agent on the plurality of cells comprises fluorescence staining the cancer cells with calcein AM and ethidium homodimer and fluorescence imaging to quantify % live and % dead cancer cells.

Aspect 31: The method according to any of aspects 24-30, wherein the agent comprises one or more conventional chemotherapeutic drugs; one or more new agents; or a combination thereof.

Aspect 32: The method according to aspect 31, wherein the one or more conventional chemotherapeutic drugs are selected from the group consisting of vinorelbine, cisplatin, ipilimumab, afatinib, dasatinib, cediranib, bevacizumab, PX-866, selumetinib, dalantercept, trebananib, doxorubicin, paclitaxel, and 5-fluorouracil.

Aspect 33: A kit comprising:
  a) a first component comprising a system comprising:
    i. a crosslinked poly(alkylene glycol) (PAG)-based hydrogel composition,
    ii. a cell culture media in contact with the crosslinked PAG-based hydrogel composition, and
    iii, a plurality of cancer cells in contact with the cell culture media and encapsulated in the crosslinked PAG-based hydrogel composition; and
  b) a second component comprising an instruction for regulating the state of the cancer cells according to claim 1.

Aspect 34: The kit of aspect 33 further comprising a third component comprising a co-monomer.

Aspect 35: The kit of aspect 33 or 34 further comprising a fourth component comprising a cell-adhesive macromer.

Aspect 36: The kit according to any of aspects 33-35, further comprising a fifth component comprising a hydrogel digesting agent.

Aspect 37: The kit according to aspect 33, wherein the second component further comprises an instruction for screening an agent for effectiveness of the agent against cancer cells according to aspect 2.

Aspect 38: A kit comprising:
  a) a first component comprising a precursor hydrogel composition comprising a polymer-peptide macromer and a Type I photoinitiator; and
  b) a second component comprising an instruction for making the crosslinked PAG-based hydrogel according to any of aspects 2-4.

Aspect 39: The kit according to aspect 38 further comprising a third component comprising a co-monomer, and wherein the second component further comprises an instruction for making the crosslinked PAG-based hydrogel according to claim 9.

Aspect 40: The kit according to aspect 38 or 39 further comprising a fourth component comprising a cell-adhesive macromer and wherein the second component further comprises an instruction for making the crosslinked PAG-based hydrogel according to claim 7.

Aspect 41: The kit according to any of aspects 39-40 further comprising a fifth component comprising a hydrogel digesting agent.

Aspect 42: The kit according to any of aspects 38-42 further comprising a sixth component comprising a plurality of cancer cells in contact with a cell culture media.

Aspect 43: The kit of according to any of aspects 38-42, wherein the second component further comprises an instruction for screening an agent for effectiveness of the agent against cancer cells according to any of aspects 23-31.

As used herein, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Within this specification, embodiments have been described in a way which enables a clear and concise specification to be written, but it is intended and will be appreciated that embodiments may be variously combined or separated without departing from the invention. For example, it will be appreciated that all preferred features described herein are applicable to all aspects of the invention described herein.

In some embodiments, the invention herein can be construed as excluding any element or process step that does not materially affect the basic and novel characteristics of the crosslinked hydrogels compositions, systems, and methods for making or using such systems. Additionally, in some embodiments, the invention can be construed as excluding any element or process step not specified herein.

EXAMPLES

Examples of the present invention will now be described. The technical scope of the present invention is not limited to the examples described below.

ABBREVIATIONS

DI—Distilled
DIPEA—N'N-Di-isopropylethylamine
DMEM—Dulbecco's Modified Eagle Media
DMSO—Dimethyl Sulfoxide
EdU—5-ethynyl-2'-deoxyuridine
FBS—Fetal Bovine Serum
FITC—Fluorescein isothiocyanate
HEPES—4-(2-hydroxyethyl)-1-piperazineethanesulfonic acid
MW—Molecular Weight
MWCO—Molecular Weight Cutoff
NVP—N-Vinyl Pyrrolidinone
PDMS—Poly(dimethyl siloxane)
PEG—Poly(ethylene glycol)
PBS—Phosphate Buffered Saline
SVA—Succinimidyl Valerate
UV—Ultraviolet Materials
Materials and their source are listed below:
MDA-MB-231 cells—ATCC
DMEM—GIBCO, Thermo Fisher
FBS—GIBCO, Thermo Fisher
Penicillin-streptomycin—Lonza
Human fibronectin—Sigma-Aldrich
Acrylate-PEG-SVA (Molecular weight: 3.4 kDa)—Laysan Bio.
Peptide sequences GGGPQGIWGQGK and RGDS—Biopeptek/Genscript/American Peptide
DMSO—Sigma-Aldrich
DIPEA—Sigma-Aldrich
Dialysis membrane (MWCO 3500, Regenerated Cellulose)—Spectrum Laboratories
N-vinyl pyrrolidinone—Sigma-Aldrich
LAP—Sigma-Aldrich
PDMS (SYLGARD 184 Silicone Elastomer)—Dow Chemical
PBS—Sigma-Aldrich
Parafilm—Sigma-Aldrich
Alexa Fluor 488—Thermo Fisher
Methacryloxyethyl thiocarbamoyl rhodamine B—Polysciences
FITC-dextran—Sigma-Aldrich
Live/Dead® Cell Viability kit—Thermo Fisher
HEPES—Thermo Fisher
CF568 Annexin V—Biotium
Hoechst 33342—Thermo Fisher
Click-It® EdU Imaging Kit—Thermo Fisher
BSA—Sigma-Aldrich
Triton-X—Sigma-Aldrich
Paraformaldehyde—Electron Microscopy
DOX, PAC, and 5-FU—Cayman Chemical Methods
Cell Culture and Maintenance Metastatic breast cancer cells, MDA-MB-231, were cultured in DMEM supplemented with 10% (v/v) FBS and 1% (v/v) penicillin-streptomycin. All cells were cultured in fibronectin coated (10 μg/mL) T25 or T75 flasks at 37° C. and 5% $CO_2$ and grown to 80% confluency before passage and seeding. Prior to encapsulation in hydrogels, cells were serum-starved by incubation in basal media without FBS for 48 hours.

Peg-Peptide Synthesis and Characterization

Acrylate-PEG-SVA (MW: 3400 Da), proteolytically degradable peptide sequence GGGPQG↓IWGQGK (PQ, MW: 1141.24 Da Layson Bio., ↓ denotes cleavage site by matrix metalloproteinase-2 and -9) and cell-adhesive peptide sequence RGDS (MW: 433.42 Da) (American Peptide) were obtained commercially. Acrylate-PEG-SVA was reacted with PQ peptide at 2.1:1 (PEG-SVA:peptide) molar ratio in DMSO in the presence of DIPEA (molar ratio of DIPEA:PQ=4:1) at room temperature for 48 hours to form biofunctionalized peptide product, PEG-PQ-PEG. Parallelly, acrylate-PEG-SVA was reacted with RGDS peptide at 1.1:1 (PEG-SVA:peptide) molar ratio in DMSO with DIPEA (molar ratio of DIPEA:RGDS=2:1) under similar conditions to form monofunctionalized peptide product, PEG-RGDS. Reacted products were dialyzed against DI water for 24 hours with 4 water changes (MWCO 3500, Regenerated Cellulose, Spectrum Laboratories). Dialyzed products were frozen, lyophilized and stored at −80° C. under argon. Reaction conjugation was verified by gel permeation chromatography (GPC, Waters, aqueous phase).

Hydrogel Fabrication and Cell Encapsulation

PEG-PQ-PEG (PEG-PQ) (MW: 7900 Da) was reconstituted in PBS to a final concentration of 5% w/v. (6.3 mM) PEG-RGDS (MW: 3800 Da) was reconstituted in PBS to final concentrations of 0, 1, 5 and 10 mM. N-vinyl pyrrolidinone (NVP) was mixed with the PEG-PQ and PEG-RGDS precursor to final concentrations of 0.0, 4.7, 9.4, 18.7 mM along with UV-initiated photocrosslinker, lithium phenyl-2,4,6-trimethylbenzoylphosphinate (LAP, final concentration: 10 mM (3.0 mg/mL)). PDMS spacers (thickness: 500 µm) were fabricated according to established protocols and 3 mm diameter holes were punched to form molds. Polymer precursor (~4 µL) was pipetted into molds attached to a glass slide and exposed to UV light (Blak-Ray flood UV lamp, wavelength: 365 nM, intensity: 10 mW/cm$^2$) for 1 minute to form photocrosslinked hydrogels. Hydrogels were transferred to well plates and allowed to incubate in PBS at room temperature overnight to ensure removal of uncrosslinked moieties.

For cell culture studies, MDA-MB-231 cells were trypsinized, counted and resuspended in polymer precursor at $10 \times 10^6$ cells/mL. A Strip of Parafilm was stretched on a glass slide or a Petri dish to create a hydrophobic surface and cell-laden precursor (volume: 3 µL) was pipetted in droplets on the Paraflim surface. After UV exposure for 1 minute, photocrosslinked cell-laden hydrogels were transferred to well plates and cultured in media for at least 15 days or longer, depending on cellular assays. Cells in hydrogels were imaged under phase contrast every 5 days using an inverted Zeiss AxioObserver Z1 microscope.

For chemoresistance study, the polymerized, cell-laden hydrogels were transferred to a well plate and cultured in medium for 15 days, with medium changes every 4 days.

Characterization of RGDS Incorporation

The final concentration of conjugated RGDS in acellular PEG-PQ hydrogels as a function of NVP (0.0, 4.7, 9.4, 18.7 mM) was estimated via fluorescence imaging and image analysis. A fluorophore analog PEG-RGDS-Alexa Fluor 488 (RGDS-488) was synthesized in a similar fashion as PEG-RGDS and added to the precursor at a concentration of 0.5 mM. The concentrations of PEG-RGDS was adjusted to 0.5, 4.5, and 9.5 mM to ensure the total concentration of RGDS moieties equal to 1, 5, and 10 mM respectively. Polymer precursors were pipetted in the PDMS molds and imaged immediately under green fluorescence. After 1 minute UV exposure, the hydrogels were imaged again under the same settings and the pre-crosslinked and post-crosslinked fluorescence intensities were analyzed via FIJI software (NIH, Version 1.52h) to obtain the percentage reduction in fluorescence due to bleaching. The bleached RGDS-488 hydrogels were rinsed in PBS overnight to remove unconjugated PEG-RGDS and the fluorophore analog. Fluorescent images of the rinsed hydrogels were acquired using the same settings and the relative intensities were used to measure the final conjugation efficiencies. Imaging was performed using an inverted Zeiss AxioObserver Z1 fluorescent microscope fitted with a Zeiss AxioCam MRm camera. Images were acquired 200 µm from the bottom of the hydrogel to ensure imaging at the same z-height to account for hydrogel swelling. A replicate of 4 hydrogels was used for each condition.

The following assumptions were made for calculation of the conjugated PEG-RGDS concentrations:
1. PEG-RGDS and the fluorophore analog RGDS-488 have the same incorporation efficiency.
2. The molecular weights of PEG-RGDS and its fluorophore analog are similar (based on molar ratios used during synthesis).
3. Overnight rinsing ensures complete removal of unconjugated monoacrylated moieties.

The following equations were used to calculate the concentration of conjugated PEG-RGDS in the gradient hydrogels:

$$\text{Relative bleaching } (B) = \frac{I_1}{I_0} \quad (1)$$

Where $I_0$ is the normalized fluorescence intensity prior to crosslinking and $I_1$ is the normalized fluorescence intensity immediately after crosslinking and bleaching.

$$\text{Relative conjugation } (C) = \frac{I_2}{I_1} \quad (2)$$

Where $I_2$ is the normalized fluorescence intensity after rinsing and removal of unconjugated moieties.

$$\text{Conjugated RGDS concentration ([RGDS])} = C \times R \quad (3)$$

Where R is the initial PEG-RGDS concentration in the polymer precursor (R=1, 5 or 10 mM RGDS).

For chemoresistance study, PEG-RGDS concentrations were adjusted to 9.5 and 0.5 mM, with rest of the procedure as explained above.

Mechanical Characterization

PEG-PQ hydrogels were made by pipetting 15 µL of precursor in a 1 mm tall cylindrical PDMS mold (diameter=3 mm). Hydrogels were either acellular or laden with MDA-MB-231 cells ($10 \times 10'$ cells/mL) for 1 day (with 1 mM RGDS in the precursor) or maintained in culture for 15 days prior to testing. The presence of 1 mM RGDS in the cellular hydrogels was assumed to have minimal effect on the compressive modulus of the hydrogel compared to the acellular hydrogels with 0 mM RGDS. Samples were loaded on to a Universal Testing System 3340 Series (Instron) using platens for unconfined compression testing in the presence of warm PBS. Samples were compressed using a 10 N load cell at 2 µm/s for 100 seconds with an initial load of 0.02 N to ensure uniform contact. The slope of a linear fit of the stress vs. strain curve (within the first 20% of the strain compression) was calculated as the compressive modulus of the sample. A replicate of 3 hydrogels was used for each condition.

For chemoresistance study, MDA-MB-231 cell-laden PEG-PQ hydrogels with either 0 or 9.4 mM NVP were polymerized in 3 mm diameter, 1 mm tall cylindrical PDMS molds using 15 µL of prepolymer solution.

Swelling Ratio Estimation

PEG-PQ hydrogels with varying NVP concentrations (0.0, 4.7, 9.4, 18.7 mM) were fabricated and allowed to swell to equilibrium state in PBS overnight at 4° C. Swollen hydrogels were weighed in a carefully tared weighing balance and allowed to dry in ambient air for 6 hours. Dried hydrogels were reweighed, and the swelling ratio was calculated as follows:

$$\text{Swelling ratio} = \frac{\text{Swollen Weight} - \text{Dry Weight}}{\text{Dry Weight}} \quad (4)$$

A replicate of 4 hydrogels was used for each condition.

For chemoresistance study, to calculate swelling ratio, PEG-PQ hydrogels with either 0 or 9.4 mM NVP (n=4) were polymerized and placed in PBS overnight, allowing gels to swell to equilibrium before being weighed.

Degradation Analysis

PEG-PQ hydrogels with varying NVP concentrations (0.0, 4.7, 9.4, 18.7 mM) and containing 1 mM methacryloxyethyl thiocarbamoyl rhodamine B (Polysciences) were fabricated and allowed to swell in PBS overnight. Collagenase IV (Worthington, 260 U/mg) was prepared in PBS at 100 µg/mL, warmed to 37° C. and added to the swollen hydrogels. Hydrogels were incubated at 37° C. and imaged under red fluorescence using an Inverted Zeiss AxioObserver Z1 fluorescent microscope at 15 minute intervals over 3 hours. Fluorescence intensity was measured over time and changes in fluorescence intensities of degraded samples were measured using FIJI software (NIH, 1.51r) to determine relative degradation. The degradation rate was determined by fitting the intensity versus time data and determining the slope of the linear portion. Hydrogels incubated in PBS without collagenase were used as the control to account for potential photobleaching. A replicate of 3 hydrogels was used for each condition.

For chemoresistance study, to calculate the degradation rate, PEG-PQ hydrogels containing 1 mM methacryloxyethyl thiocarbamoyl rhodamine B (Polysciences) and 0 or 9.4 mM NVP were prepared and allowed to swell overnight in PBS (n=3).

Measurement of Diffusion Kinetics and Mesh Size

PEG-PQ hydrogels with varying NVP concentrations (0.0, 4.7, 9.4, 18.7 mM) were fabricated and allowed to swell in DI water to equilibrium state. 3 kDa FITC-dextran and 150 kDa FITC-dextran (Thermo Fisher) was dissolved in DI water at 1 mg/mL. Swollen hydrogels were transferred to dextran solutions and allowed to incubate for 48 hours at 4° C. Dextran-laden hydrogels were transferred to fresh well plates, excess dextran blotted off and DI water was added to each sample for diffusion of entrapped dextran. Samples of the DI water were collected every 15 minutes over 4 hours and measured in a plate reader (Biotek Synergy, Excitation: 490 nm, Emission: 525 nm) until no change in fluorescence intensity was observed. Equal volume of DI water was added to compensate for the collected sample. Fluorescence intensity values were normalized to the total intensity of released FITC-dextran over the experimental time course. The cumulative mass of FITC-dextran released was analyzed from the fluorescence intensities and used to calculate the diffusion coefficient of FITC-dextran according to the equation given below:

$$\frac{M_t}{M_\infty} = 1 - \frac{8}{n^2}\exp\left[\frac{-Dn^2 t}{4\delta^2}\right] \quad (5)$$

where $M_t$ is the mass of released FITC-dextran at time t, $M_\infty$ is the cumulative mass of FITC-dextran, $M_t/M_\infty$ is the fractional mass of FITC-dextran released, D is the diffusion coefficient and 2δ is the hydrogel thickness (500 µm).

The theoretical mesh size of the hydrogels was estimated using the hindered solute diffusion in solvent-filled-pores model based on the following equation:

$$\frac{D}{D_0} = (1 - \lambda^2)(1 - 2.1044\lambda + 2.089\lambda^3 - 0.948\lambda^5) \quad (6)$$

Where D is the diffusion coefficient of 150 kDa FITC-dextran in hydrogels, Do is the diffusion coefficient of 150 kDa FITC-dextran calculated from the Stokes-Einstein's equation ($2.09 \times 10^{-7}$ cm$^2$/s), and λ is a characteristic ratio of FITC-dextran hydrodynamic diameter to average pore diameter of hydrogel matrix.

A replicate of 4 hydrogels per condition were analyzed for the measurement of diffusion coefficients and mesh size.

For chemoresistance study, to determine theoretical mesh size, PEG-PQ hydrogels with either 0 or 9.4 mM NVP were polymerized and allowed to swell in DI water overnight (n=4) using the procedure as described above.

Quantification of Cell Viability

Hydrogels with encapsulated cells were collected from 3D culture at days 0, 5, 10, and 15, and rinsed twice in PBS for 15 minutes to remove excess media. Rinsed hydrogels were stained with Live/Dead® cell viability stain (Invitrogen) in PBS for 30 minutes. Stained hydrogels were rinsed further with PBS, transferred onto coverslips and imaged using structured illumination on an inverted Zeiss AxioObserver Z1 fluorescent microscope fitted with Zeiss Apotome unit. Fluorescent z-stacks (z-height: 150 µm, step size: 3 µm) were acquired and analyzed using FIJI software. The number of live and dead cells were manually counted in each z-stack to obtain cell viability and the number of viable cells in a given volume of the z-stack was quantified to obtain the viable cell density. A minimum of 6 z-stacks from 3 independent hydrogels were quantified for each time point and each hydrogel condition.

For chemoresistance study, cell viability was measured at days 0 (6 hr post encapsulation) and 15.

Quantification of Early Apoptosis

Hydrogels with encapsulated cells were collected at days 0, 5, 10, and 15, and rinsed twice in 1×HEPES-buffered saline (HBS) supplemented with 2.5 mM calcium chloride. Rinsed hydrogels were incubated in a solution containing CF568 Annexin V (Biotium, 1 µg/mL), an early apoptotic marker, at 37° C. for 30 minutes. Cells were counterstained with Hoechst 33342 (10 µg/mL) for nuclear staining. Stained cells were rinsed with HBS twice and imaged using structural Illumination. Imaging and image analysis were conducted as described earlier. The percentage of cells stained positive for Annexin V was quantified. A minimum of 6 z-stacks from 3 independent hydrogels were quantified for each time point and each hydrogel condition.

For chemoresistance study, cells undergoing early apoptosis were measured at days 0 and 15.

Quantification of Proliferation

Cell proliferation was measured using the EdU uptake assay using the Click-It® EdU Imaging Kit (Invitrogen) and fluorescence imaging. Briefly, hydrogels with encapsulated cells were incubated with media containing 10 µM EdU for 24 hours, after which they were rinsed twice with PBS, and fixed with 4% paraformaldehyde. Fixed cells were permeabilized with PBS-T (PBS+0.2% (w/v) bovine serum albumin+0.1% (v/v) Triton-X) for 15 minutes and blocked with blocking buffer (PBS+3% fetal bovine serum) for 30 minutes. Cells were subsequently stained with Alexa Fluor 555 azide (proliferating nuclei) and co-stained with Hoechst 33342 (total nuclei) and imaged using structural illumination. Imaging and image analysis were conducted as described earlier. The percentage of nuclei stained positive for Alexa Fluor 555 was quantified. A minimum of 6 z-stacks from 3 independent hydrogels were quantified for each time point and each hydrogel condition.

For chemoresistance study, proliferation was measured at days 0 and 15.

Quantification of Metabolic Activity

Metabolic activity of cells encapsulated in hydrogels was assessed using the Alamar Blue assay (ThermoFisher). Briefly, cells encapsulated in hydrogels were cultured in phenol red-free media throughout the culture period. At specific time points, hydrogels were rinsed twice with PBS and incubated in a working solution of Alamar Blue (10 µL of 10× stock+100 µL phenol red-free media) at 37° C. for 4 hours. Resazurin in the working solution was converted to resorufin and the media was collected, transferred into fresh well plates and analyzed using a plate reader (Biotek Synergy, Excitation: 550 nm, Emission: 600 nm) to assess relative metabolic activity. All values were normalized to day 0 values for each hydrogel condition. A minimum of 6 independent hydrogels were quantified for each time point and each hydrogel condition.

For chemoresistance study, metabolic activity was measured at days 0 and 15.

Morphological Assessment

Hydrogels with encapsulated cells were cultured through 15 days, after which they were rinsed twice in PBS and fixed in 4% paraformaldehyde for 30 minutes at room temperature. Fixed cell-laden hydrogels were permeabilized with PBS-T (PBS+0.2% (w/v) bovine serum albumin+0.1% (v/v) Triton-X) for 20 minutes and blocked with blocking buffer (PBS+3% fetal bovine serum) for 30 minutes. They were subsequently incubated with Alexa Fluor 568 phalloidin (Invitrogen) (25 µL/mL) for 1 hour (for F-actin staining) and counterstained with Hoechst 33342 (10 µL/mL) (for nuclear staining) for 30 minutes. Stained cells were rinsed twice in PBS and imaged via confocal microscopy (Zeiss LSM 710) to obtain 3D z-stacks. 5 z-stacks (z-height: 150 µm, step size: 3 µm) were obtained for each hydrogel condition and analyzed using FIJI software. Individual cells/cell clusters were manually traced and the percentage of single cells vs. clustered cells, rounded cells vs. invasive cells, and non-invasive vs. invasive clusters were quantified for each hydrogel condition. Invasive cells/cell clusters were identified as those with a roundness of less than 0.80. In addition, for cell clusters, the cluster density (number of clusters/$mm^3$), projected area, Feret diameter, aspect ratio, circularity and roundness were also quantified.

Classification of Cell States and Phenotypic Dormancy Metrics

In order to classify crosslinked hydrogel compositions that induce and support specific cell states, assessed phenotypic metrics (viable cell density, viability, cell/cluster morphology) were statistically compared. First, the viable cell density for each hydrogel condition at each time point was evaluated and statistically compared to the baseline values for corresponding condition on day 0. Hydrogel conditions where day 15 values were significantly higher than corresponding day 0 values were grouped into 'invasive growth' category. Remaining hydrogel conditions were assessed for cell viability and those where day 15 values were less than 10% of day 10 values were grouped into 'single cell restricted survival dormancy' category. Remaining hydrogel conditions were assessed for cell/cluster morphology. When single cells constituted >80% of total cells and clustered cells constituted <20% of total cells, corresponding hydrogel conditions were grouped into 'single cell balanced survival dormancy' and remaining hydrogel conditions were grouped into 'tumor mass balanced survival dormancy.'

Reactivation of Dormant Cancer Cells

MDA-MB-231 cells were encapsulated in 5% (w/v) PEG-PQ hydrogels with 0 mM NVP and 0 mM PEG-RGDS as described previously and maintained in 3D culture. Live/Dead staining and EdU uptake assay was conducted every 15 days as described earlier. On day 40, 10 mM PEG-RGDS in PBS containing 10 mM LAP photoinitiator was prepared. Hydrogels were removed from media, rinsed twice in PBS for 15 minutes and incubated in the PEG-RGDS solution for 1 hour at 37° C. to allow diffusion of RGDS moiety in the hydrogel matrix. After 1 hour, hydrogels were removed, exposed to UV light for 1 minute for crosslinking of diffused RGDS to the PEG-PQ matrix, and finally returned to culture media for long-term 3D culture. Hydrogels were stained and imaged for cell viability and proliferation on days 45, 60 and 75 post-conjugation of RGDS. Imaging and image analysis were conducted as described earlier. A minimum of 6 z-stacks from 3 independent hydrogels were quantified for each time point and each hydrogel condition.

Statistical Analysis

All statistical analyses were conducted using Minitab 18 Statistical Software (Minitab Inc.). Normality of distribution and equality in variance among groups were evaluated. Assuming equal sample size of compared groups, one-way analysis of variance (ANOVA) with Tukey's family error rate of 5% was used to evaluate statistical significance between multiple groups. In case of unequal variance between groups, the Games-Howell post-hoc test was employed following the ANOVA analysis. Unless otherwise indicated, $p<0.05$ was considered statistically significant.

Results

Example 1: Systems Comprising Crosslinked Poly(Alkylene Glycol) (PAG)-Based Hydrogel Composition Sixteen different systems comprising crosslinked poly (ethylene glycol) (PEG)-based hydrogel compositions, cancer cells and cell culture media were prepared using the method described hereinabove and summarized in Table 1.

The PEG-based hydrogels of the present inventions were primarily composed of PEG-PQ macromer, a polymer-peptide macromer and LAP, a Type 1 ultraviolet (UV) photoinitiator. The PEG-PQ macromer was formed by covalent conjugation of a first poly(alkylene glycol), such as PEG-SVA with peptide such as proteolytically-degradable peptide having a sequence GGGPQGIWGQGK, as shown in FIG. 1A. Parallelly, PEG-SVA was also covalently conjugated with integrin-ligating cell-adhesive peptide sequence such as RGDS to form PEG-RGDS macromer, a cell-adhesive macromer, as shown in FIG. 1B. The PEG-PQ (5% w/v) and PEG-RGDS macromer (0-10 mM) were combined with non-degradable co-monomer NVP (0-18.7 mM) in various ratios and crosslinked using UV photoinitiator LAP and UV light exposure to form hydrogel droplets. Cancer cells were suspended in the liquid polymer precursor prior to crosslinking and upon encapsulation, were maintained in 3D cell-culture media for at least 15 days, as shown in FIG. 1C.

The PEG-PQ moiety allows encapsulated cells to degrade the surrounding matrix through cell-secreted matrix-metalloproteases (MMPs). The PEG-RGDS moiety allows encapsulated cells to adhere to the matrix using cell-surface integrins and tuning its concentration allows control over matrix adhesivity. The NVP moiety, on account of acrylate groups in its structure, provides additional crosslink sites on the PEG-PQ macromer backbone and regulates several physical and biochemical properties of the resulting hydrogel matrix.

Example 2: Effect of Co-Monomer NVP Incorporation in the Crosslinked PAG-Hydrogel The effect of the incorporation of co-monomer NVP in the fabricated crosslinked PEG-PQ hydrogel compositions was studied by characterizing: 1) final conjugated RGDS concentration (representative of actual hydrogel adhesivity), 2) compressive moduli with and without encapsulated cells, 3) swelling, 4) degradation, 5) diffusion behavior of small molecule dextran, and 6) theoretical mesh size. The results are summarized in Table 1.

efficiency of RGDS (1-10 mM) was around 20%, but in the presence of NVP (4.7-18.7 mM) conjugation efficiency increased to around 80%. Without wishing to be bound by any particular theory, it is believed that the Increased conjugation efficiency of RGDS in the presence of NVP can be attributed to the presence of additional acrylate sites provided by the NVP and the increased NVP/acrylate ratio in the final polymer precursor. The final RGDS concentration conjugated in each crosslinked hydrogel composition is enlisted in Table 1.

It should be noted in Table 1, that the addition of NVP also led to an increase in bulk compressive moduli of hydrogels in a proportional manner. Presence of NVP leads to increased crosslink density between polymer chains, thereby leading to increased overall stiffness. In this case, compressive moduli of acellular hydrogels varied from around 5-27 kPa for NVP concentrations of 0-18.7 mM. Encapsulation of cells within hydrogels usually led to reduced bulk stiffness of overall cellular constructs, except for hydrogels with 0 mM NVP on day 0. This was due to: 1) substitution of hydrogel volume with encapsulated cell volume and 2) inherent lower stiffness of cells (<1 kPa) compared to acellular hydrogel matrices. For hydrogels with 0 mM NVP, this observation was reversed, possibly due to detection limitations of the equipment in the soft stiffness range.

TABLE 1

| Crosslinked hydrogel composition | | Actual [RGDS] | Compressive Modulus (kPa) | Swelling ratio | Time to 50% degradation | Diffusion coefficient (3 kDa | Diffusion coefficient 150 kDa | Mesh size |
|---|---|---|---|---|---|---|---|---|
| NVP | RGDS | mM | (Acellular) | (%) | (min.) | dextran) | dextran) | (nm) |
| Invasive Growth State | | | | | | | | |
| 0 | 1 | 0.21 ± 0.02 | 5.8 ± 2.0 | 1725 ± 90 | 47 | 1.39E−07 ± 7.60E−09 | 1.01E−07 ± 6.55E−09 | 69 ± 5 |
| | 5 | 1.08 ± 0.10 | 5.8 ± 2.0 | 1725 ± 90 | 47 | 1.39E−07 ± 7.60E−09 | 1.01E−07 ± 6.55E−09 | 69 ± 5 |
| | 10 | 1.89 ± 0.14 | 5.8 ± 2.0 | 1725 ± 90 | 47 | 1.39E−07 ± 7.60E−09 | 1.01E−07 ± 6.55E−09 | 69 ± 5 |
| 4.7 | 1 | 0.82 ± 0.06 | 15.1 ± 2.0 | 1363 ± 89 | 73 | 1.29E−07 ± 1.87E−08 | 8.04E−07 ± 1.17E−08 | 57 ± 6 |
| | 5 | 4.10 ± 0.36 | 15.1 ± 2.0 | 1363 ± 89 | 73 | 1.29E−07 ± 1.87E−08 | 8.04E−07 ± 1.17E−08 | 57 ± 6 |
| | 10 | 7.89 ± 0.80 | 15.1 ± 2.0 | 1363 ± 89 | 73 | 1.29E−07 ± 1.87E−08 | 8.04E−07 ± 1.17E−08 | 57 ± 6 |
| 9.4 | 5 | 8.26 ± 0.80 | 18.1 ± 1.8 | 1263 ± 65 | 89 | 1.35E−07 ± 1.58E−08 | 8.02E−07 ± 5.21E−09 | 55 ± 4 |
| | 10 | 0.00 ± 0.00 | 18.1 ± 1.8 | 1263 ± 65 | 89 | 1.35E−07 ± 1.58E−08 | 8.02E−07 ± 5.21E−09 | 55 ± 4 |
| Single cell restricted survival dormancy | | | | | | | | |
| 0 | 0 | 0.00 ± 0.00 | 5.8 ± 2.0 | 1725 ± 90 | 47 | 1.39E−07 ± 7.60E−09 | 1.01E−07 ± 6.55E−09 | 69 ± 5 |
| 4.7 | 0 | 0.00 ± 0.00 | 15.1 ± 2.0 | 1363 ± 89 | 73 | 1.29E−07 ± 1.87E−08 | 8.04E−07 ± 5.21E−09 | 57 ± 6 |
| 9.4 | 0 | 0.00 ± 0.00 | 18.1 ± 1.8 | 1263 ± 65 | 89 | 1.35E−07 ± 1.58E−08 | 8.02E−07 ± 1.72E−08 | 55 ± 4 |
| 18.7 | 0 | 0.00 ± 0.00 | 27.2 ± 2.1 | 1188 ± 41 | 89 | 1.20E−07 ± 1.52E−08 | 6.76E−08 ± 1.72E−08 | 51 ± 9 |
| Single cell balanced survival dormancy | | | | | | | | |
| 9.4 | 1 | 0.79 ± 0.07 | 18.1 ± 1.8 15.1 ± 2.0 18.1 ± 1.8 27.2 ± 2.1 | 1263 ± 65 | 89 | 1.35E−07 ± 1.58E−08 | 8.02E−07 ± 5.21E−09 | 55 ± 4 |
| Tumor mass balanced survival dormancy | | | | | | | | |
| 18.7 | 1 | 0.80 ± 0.05 | 27.2 ± 2.1 | 1188 ± 41 | 89 | 1.20E−07 ± 1.52E−08 | 6.76E−08 ± 1.72E−08 | 51 ± 9 |
| | 5 | 4.21 ± 0.31 | 27.2 ± 2.1 | 1188 ± 41 | 89 | 1.20E−07 ± 1.52E−08 | 6.76E−08 ± 1.72E−08 | 51 ± 9 |
| | 10 | 8.58 ± 0.86 | 27.2 ± 2.1 | 1188 ± 41 | 89 | 1.20E−07 ± 1.52E−08 | 6.76E−08 ± 1.72E−08 | 51 ± 9 |

Values represent mean ± standard deviation; n = 4 hydrogels per condition

As shown in Table 1, the presence of NVP had a drastic effect in the conjugation efficiency of RGDS to the PEG-PQ backbone. In the absence of NVP (0 mM), the conjugation Table 2 shows bulk compressive moduli values of acellular hydrogels on day 0 and cellular hydrogels on day 0 and day 15. Interestingly, compressive moduli of cellular constructs on day 15 was significantly lower than corresponding values on day 0, owing to cell-mediated proteolytic matrix degradation over 15 days in culture.

TABLE 2

| | Compressive Modulus (kPa) | | | |
|---|---|---|---|---|
| [NVP] | 0.0 mM | 4.7 mM | 9.4 mM | 18.7 mM |
| Acellular Hydrogels Day 0 | 5.8 ± 2.0 | 15.1 ± 2.0 | 18.1 ± 1.8 | 27.2 ± 2.1 |
| Cellular Hydrogels Day 0 | 9.4 ± 0.8 | 9.7 ± 0.8 | 12.3 ± 0.6 | 14.0 ± 0.4 |
| Cellular Hydrogels Day 15 | 3.0 ± 0.6 | 3.6 ± 0.5 | 6.3 ± 5 | 6.9 ± 0.5 |

Bulk Compressive Modulus values are in kPa (Mean ± standard deviation); n = 3 hydrogels per condition As shown in Table 1, the addition of NVP also led to a gradual reduction in hydrogel swelling from around 1700% to 1200%, owing to increased matrix density and lower water absorption ability. Values for swelling ratio for each hydrogel composition is provided in Table 1. Incorporation of NVP also led to a gradual reduction in hydrogel degradation owing to: 1) non-degradability of NVP co-monomer and 2) reduced accessibility of the degradable PQ peptide sequence in matrices with higher crosslink density.

FIG. 6 shows that the hydrogel with 0 mM NVP underwent complete degradation in collagenase IV in around 160 minutes. However, degradation of the hydrogels appears to be reduced with an increase in the amount of NVP. As shown in FIG. 6, the hydrogels with 4.7-18.7 mM NVP underwent partial degradation (70-80%) over time (as observed till 2 days post treatment). The time taken for hydrogels to undergo 50% degradation is summarized in Table 1.

The effect of NVP on hydrogel pore structure and diffusion behaviour of small molecule was investigated with dextran fluorescently conjugated with fluorescein isothiocyanate (FITC-dextran), with dextran having two molecular weights (3 kDa and 150 kDa). As shown in Table 1, 3 kDa dextran did not show any significant effect on diffusions through hydrogels with varying NVP concentrations, possibly owing to smaller hydrodynamic radius of 3 kDa dextran compared to hydrogel mesh size. However, Table 1 shows appreciable reduction in diffusion of 150 kDa dextran through hydrogels with increasing NVP, owing to hindered transport across hydrogel pores.

The theoretical mesh size of hydrogels with varying NVP concentrations was calculated based on the observable differences in diffusion coefficients of the 150 kDa dextran and are shown in table 1. Based on calculations, addition of NVP led to reduced mesh size in hydrogels, thereby confirming the presence of higher crosslink density in hydrogel matrices due to NVP.

Example 3: Effect of the Hydrogel Properties on the State of the Cancer Cells

FIG. 7 shows the role of hydrogel properties on the fate of the encapsulated cancer cell, by assessing phenotypic metrics of encapsulated cancer cells at specific time interval post encapsulation. First, cell viability was quantified in hydrogels at days 0, 5, 10 and 15 by staining with calcein AM (live cells) and ethidium homodimer (late cell death) and fluorescence imaging. Viability values on day 0 post encapsulation were around 80% or higher for all crosslinked hydrogel compositions, indicating high viability and low phototoxicity due to UV exposure. From days 5-15, viability in hydrogels with 0 mM RGDS dropped significantly to 30-40%, possibly owing to lack of cell-adhesion sites and integrin-ligation in the matrix. However, viability remained relatively high (>70%) in all other crosslinked hydrogel compositions, indicating that RGDS is necessary for maintaining high cell viability. Hence, viability is highly dependent on RGDS concentration and less dependent on NVP concentration within the tested range. Cell viability values for each condition and time interval are summarized in Table 3.

TABLE 3

| [NVP] | [RGDS] | Cell Viability (%) | | | |
|---|---|---|---|---|---|
| mM | mM | Day 0 | Day 5 | Day 10 | Day 15 |
| 0.0 | 0 | 85.9 ± 2.9 | 69.5 ± 5.9 | 48.2 ± 1.8 | 41.3 ± 2.0 |
| | 1 | 84.7 ± 3.3 | 86.3 ± 1.4 | 86.2 ± 2.9 | 89.6 ± 2.2 |
| | 5 | 85.7 ± 2.4 | 88.2 ± 2.0 | 88.4 ± 2.4 | 88.2 ± 1.8 |
| | 10 | 88.3 ± 1.5 | 86.7 ± 2.0 | 91.7 ± 1.1 | 94.3 ± 1.4 |
| 4.7 | 0 | 82.0 ± 1.7 | 71.5 ± 3.3 | 55.5 ± 3.9 | 43.2 ± 2.0 |
| | 1 | 86.2 ± 2.6 | 80.9 ± 2.3 | 83.5 ± 2.3 | 87.5 ± 1.1 |
| | 5 | 84.5 ± 2.2 | 77.8 ± 3.3 | 77.5 ± 1.1 | 77.0 ± 3.4 |
| | 10 | 79.2 ± 1.7 | 82.4 ± 1.7 | 84.3 ± 2.0 | 83.1 ± 2.6 |
| 9.4 | 0 | 82.0 ± 0.9 | 65.5 ± 3.9 | 53.9 ± 5.2 | 39.7 ± 4.2 |
| | 1 | 85.1 ± 2.3 | 83.2 ± 0.8 | 80.3 ± 2.1 | 84.5 ± 2.4 |
| | 5 | 82.7 ± 2.7 | 79.7 ± 2.8 | 72.4 ± 2.4 | 72.9 ± 3.7 |
| | 10 | 81.2 ± 3.3 | 73.9 ± 2.6 | 76.0 ± 2.5 | 81.5 ± 2.7 |
| 18.7 | 0 | 80.6 ± 2.6 | 50.6 ± 3.6 | 42.1 ± 2.9 | 33.6 ± 4.5 |
| | 1 | 89.3 ± 2.1 | 81.5 ± 3.9 | 78.5 ± 1.3 | 83.2 ± 2.4 |
| | 5 | 84.2 ± 3.8 | 74.8 ± 4.8 | 76.4 ± 3.5 | 74.1 ± 2.7 |
| | 10 | 82.6 ± 3.1 | 75.3 ± 4.8 | 71.1 ± 4.5 | 73.9 ± 2.8 |

Cell Viability Values in (Mean ± standard deviation); n = 6 z-stacks from 3 hydrogels per condition Example 4: Effect of Hydrogel Properties on the Mechanism of Cancer Cell Death The effect of hydrogel properties on the mechanism of cancer cell death was studied by staining the cells in the crosslinked hydrogel compositions with annexin V (an early apoptosis marker) at days 0, 5, 10 and 15, and counterstaining with nuclear stain Hoechst 33342. Cancer cells in hydrogels with 0 mM RGDS displayed high degree of apoptotic cell death (~40-65%), consistent with previous observations with ethidium homodimer staining. However, hydrogels containing RGDS displayed significantly low staining for annexin V (~10-20%), indicating that presence of RGDS prevents apoptotic cell death. Hence, apoptotic cell death is primarily dependent on RGDS concentration and depends weakly on NVP concentration. Of note here is the fact that DTCs in the secondary microenvironments usually undergo cell death via apoptosis, which is closely simulated here in the in vitro model. The values for early apoptosis for each condition and time point are summarized in Table 4.

TABLE 4

| [NVP] | [RGDS] | Early Apoptosis (%) | | | |
|---|---|---|---|---|---|
| mM | mM | Day 0 | Day 5 | Day 10 | Day 15 |
| 0.0 | 0 | 1.6 ± 0.6 | 23.4 ± 2.9 | 29.2 ± 4.2 | 43.6 ± 4.6 |
| | 1 | 3.6 ± 0.7 | 26.5 ± 1.1 | 15.0 ± 1.3 | 10.5 ± 2.6 |
| | 5 | 2.2 ± 1.9 | 18.7 ± 1.6 | 18.7 ± 3.4 | 18.1 ± 2.5 |
| | 10 | 4.7 ± 1.5 | 13.2 ± 4.2 | 14.1 ± 3.6 | 7.9 ± 1.7 |

TABLE 4-continued

| [NVP] mM | [RGDS] mM | Early Apoptosis (%) | | | |
|---|---|---|---|---|---|
| | | Day 0 | Day 5 | Day 10 | Day 15 |
| 4.7 | 0 | 0.6 ± 0.1 | 32.6 ± 5.6 | 44.6 ± 4.3 | 58.7 ± 4.6 |
| | 1 | 2.2 ± 1.1 | 24.4 ± 2.7 | 18.7 ± 2.9 | 15.2 ± 2.5 |
| | 5 | 3.1 ± 0.8 | 11.2 ± 2.5 | 15.8 ± 4.2 | 20.5 ± 1.7 |
| | 10 | 4.3 ± 0.7 | 9.4 ± 0.6 | 12.2 ± 3.5 | 10.4 ± 2.8 |
| 9.4 | 0 | 0.8 ± 0.2 | 38.8 ± 3.8 | 42.5 ± 4.5 | 55.8 ± 5.0 |
| | 1 | 1.2 ± 0.3 | 24.2 ± 2.3 | 23.8 ± 2.2 | 21.6 ± 3.3 |
| | 5 | 3.9 ± 0.4 | 17.5 ± 2.4 | 15.5 ± 2.1 | 18.6 ± 4.8 |
| | 10 | 3.1 ± 0.4 | 8.4 ± 0.9 | 9.5 ± 1.8 | 13.1 ± 0.8 |
| 18.7 | 0 | 0.6 ± 0.1 | 42.0 ± 5.1 | 53.1 ± 4.3 | 64.7 ± 5.1 |
| | 1 | 0.9 ± 0.4 | 22.8 ± 4.9 | 21.9 ± 2.1 | 18.2 ± 2.6 |
| | 5 | 5.4 ± 2.4 | 12.8 ± 3.7 | 15.9 ± 2.2 | 16.2 ± 1.9 |
| | 10 | 4.4 ± 1.2 | 7.4 ± 0.8 | 10.0 ± 0.8 | 14.2 ± 2.5 |

Early Apoptosis Values are in % (Mean ± standard deviation); n = 6 z-stacks from 3 hydrogels per condition

Example 5: Effect of Hydrogel Compositions & their Properties on the Cancer Cell Proliferation The effect of hydrogel properties on cell proliferation was assessed on days 0, 5, 10 and 15, using EdU incorporation assay and counterstaining with Hoechst 33342. EdU reagent was incorporated in the DNA of dividing cells and cells undergoing $G_0/G_1$ transition in the cell cycle stain positively for EdU. An increase in cell proliferation was observed with increasing RGDS concentrations in the hydrogels with 0 mM NVP, due to increased cell-matrix adhesion and possibly high degree of matrix permissiveness. However, as the NVP concentration was increased, cell proliferation was restricted to lower values (~20% or less), Irrespective of RGDS concentration. Without wishing to be bound by any particular theory, it is believed that the decrease in cell proliferation with an increase in the RGDS concentration, is due to additional crosslink density and denser matrix conditions that physically restrict cancer cells from undergoing cell division process and confine them in a state of cell cycle arrest. Hence, cell proliferation was observed to be dually modulated by both RGDS and NVP concentrations in a biphasic manner. The values for cell proliferation for each condition and time point are listed in Table 5.

TABLE 5

| [NVP] mM | [RGDS] mM | Day 0 | Day 5 | Day 10 | Day 15 |
|---|---|---|---|---|---|
| 0.0 | 0 | 12.2 ± 1.6 | 12.4 ± 1.3 | 13.2 ± 1.2 | 10.3 ± 0.8 |
| | 1 | 11.2 ± 2.4 | 21.8 ± 3.2 | 26.9 ± 3.7 | 33.3 ± 1.0 |
| | 5 | 11.9 ± 1.2 | 24.8 ± 3.3 | 35.1 ± 2.8 | 43.6 ± 1.9 |
| | 10 | 11.2 ± 2.1 | 29.5 ± 2.7 | 41.3 ± 2.7 | 47.2 ± 4.1 |
| 4.7 | 0 | 8.9 ± 1.6 | 9.9 ± 2.7 | 10.9 ± 0.6 | 7.2 ± 1.6 |
| | 1 | 11.5 ± 2.3 | 19.4 ± 3.2 | 21.2 ± 2.2 | 19.0 ± 2.5 |
| | 5 | 11.7 ± 2.1 | 21.2 ± 2.2 | 24.9 ± 5.5 | 19.7 ± 1.6 |
| | 10 | 11.5 ± 2.3 | 16.4 ± 3.3 | 11.8 ± 1.3 | 9.2 ± 0.5 |
| 9.4 | 0 | 11.3 ± 1.5 | 10.7 ± 2.3 | 8.5 ± 1.8 | 4.7 ± 1.6 |
| | 1 | 13.2 ± 2.1 | 14.2 ± 2.8 | 15.7 ± 2.1 | 11.9 ± 4.1 |
| | 5 | 8.6 ± 2.2 | 12.2 ± 0.8 | 9.8 ± 1.1 | 6.5 ± 1.5 |
| | 10 | 8.8 ± 1.8 | 10.2 ± 2.5 | 9.0 ± 2.3 | 5.5 ± 0.5 |
| 18.7 | 0 | 8.5 ± 0.9 | 10.6 ± 1.3 | 8.7 ± 1.5 | 4.6 ± 2.5 |
| | 1 | 12.2 ± 2.4 | 19.0 ± 3.9 | 18.0 ± 2.2 | 14.8 ± 2.6 |
| | 5 | 10.2 ± 2.4 | 14.3 ± 1.5 | 11.9 ± 1.2 | 10.6 ± 1.2 |
| | 10 | 10.4 ± 1.6 | 11.6 ± 0.9 | 9.4 ± 1.6 | 5.9 ± 2.2 |

Cell Proliferation Values are in % (Mean ± standard deviation); n = 6 z-stacks from 3 hydrogels per condition

Example 6: Effect of Hydrogel Compositions & their Properties on the Viable Cell Density Similar to cell proliferation, viable cell density (number of viable cells per unit volume of hydrogel) were quantified from fluorescent images of cells stained with calcein AM as described earlier. In hydrogels with 0 mM NVP, viable cell density increased with increasing RGDS owing to increased proliferation. In hydrogels with 0 mM RGDS, viable cell density decreased significantly owing to high cell death. However, with increasing NVP, viable cell density remained at constant levels irrespective of RGDS concentration, possibly due to restricted proliferation in matrices with higher crosslink density and physical confinement. Hence, one can conclude that the viable cell density is dually dependent on both RGDS and NVP concentrations. The values for viable cell density for each condition and time intervals are listed in Table 6.

TABLE 6:

| | | Viable Cell Density (cells/mm³) | | | |
|---|---|---|---|---|---|
| [NVP] mM | [RGDS] mM | Day 0 | Day 5 | Day 10 | Day 15 |
| 0.0 | 0 | 8511 ± 774 | 7027 ± 629 | 4943 ± 321 | 4368 ± 645 |
| | 1 | 9041 ± 930 | 9548 ± 679 | 11432 ± 1281 | 13725 ± 2019 |
| | 5 | 8202 ± 801 | 9070 ± 954 | 12889 ± 1347 | 21123 ± 1954 |
| | 10 | 8477 ± 717 | 13053 ± 635 | 18214 ± 885 | 24625 ± 953 |
| 4.7 | 0 | 8618 ± 654 | 7651 ± 924 | 6034 ± 534 | 4895 ± 322 |
| | 1 | 8652 ± 1249 | 9257 ± 925 | 10869 ± 1541 | 12118 ± 1541 |
| | 5 | 9102 ± 404 | 7690 ± 616 | 10407 ± 883 | 15205 ± 1952 |
| | 10 | 7928 ± 7326 | 9617 ± 1032 | 12710 ± 796 | 13877 ± 1191 |
| 9.4 | 0 | 8256 ± 1089 | 6836 ± 917 | 5762 ± 536 | 4092 ± 491 |
| | 1 | 9104 ± 1064 | 9223 ± 853 | 9711 ± 890 | 10375 ± 910 |
| | 5 | 8115 ± 901 | 8090 ± 605 | 8870 ± 1459 | 11735 ± 1644 |
| | 10 | 8750 ± 559 | 8495 ± 891 | 10985 ± 690 | 11243 ± 644 |
| 18.7 | 0 | 8270 ± 490 | 5239 ± 658 | 4258 ± 318 | 3482 ± 400 |
| | 1 | 9256 ± 830 | 8288 ± 1407 | 8868 ± 730 | 10234 ± 503 |
| | 5 | 8541 ± 709 | 8578 ± 692 | 9438 ± 582 | 10531 ± 760 |
| | 10 | 8914 ± 471 | 8240 ± 956 | 9884 ± 855 | 10076 ± 1122 |

Viable Cell Density Values are in cells/mm³ (Mean ± standard deviation); n = 6 z-stacks from 3 hydrogels per condton

Example 7: Effect of Hydrogel Compositions & their Properties on the Metabolic Activity of Cells Similar to viable cell density, metabolic activity of cells within different crosslinked hydrogel compositions was also assessed using the Alamar Blue assay. As shown in Table 7, the metabolic activity increasing RGDS concentration in hydrogels with 0 mM NVP, owing to Increased cell proliferation and viable cell numbers. However, in hydrogels with 0 mM RGDS, metabolic activity decreased from day 0 values owing to cell death. Furthermore, with increasing NVP, metabolic activity remained constant and close to day 0 values over time due to restricted cell proliferation. Hence, metabolic activity is dually dependent on both RGDS and NVP concentrations. The values for normalized metabolic activity for each condition and time point are summarized in Table 7 (normalized to day 0 values).

TABLE 7

| [NVP] mM | [RGDS] mM | Normalized Metabolic Activity (RU) | | | |
|---|---|---|---|---|---|
| | | Day 0 | Day 5 | Day 10 | Day 15 |
| 0.0 | 0 | 1.00 ± 0.11 | 0.93 ± 0.26 | 0.77 ± 0.27 | 0.89 ± 0.23 |
| | 1 | 1.00 ± 0.11 | 1.56 ± 0.34 | 1.79 ± 0.20 | 3.36 ± 0.45 |
| | 5 | 1.00 ± 0.14 | 2.36 ± 0.27 | 4.57 ± 0.63 | 7.29 ± 1.54 |
| | 10 | 1.00 ± 0.12 | 3.06 ± 0.19 | 7.87 ± 2.38 | 13.14 ± 1.97 |
| 4.7 | 0 | 1.00 ± 0.07 | 0.72 ± 0.14 | 0.69 ± 0.18 | 0.63 ± 0.08 |
| | 1 | 1.00 ± 0.11 | 1.35 ± 0.27 | 1.13 ± 0.42 | 1.67 ± 0.27 |
| | 5 | 1.00 ± 0.23 | 1.37 ± 0.17 | 2.28 ± 0.40 | 2.83 ± 0.52 |
| | 10 | 1.00 ± 0.17 | 1.46 ± 0.16 | 2.62 ± 0.51 | 3.58 ± 1.28 |
| 9.4 | 0 | 1.00 ± 0.11 | 0.74 ± 0.20 | 0.68 ± 0.14 | 0.61 ± 0.12 |
| | 1 | 1.00 ± 0.10 | 1.07 ± 0.30 | 2.06 ± 0.30 | 1.51 ± 0.43 |
| | 5 | 1.00 ± 0.21 | 1.36 ± 0.24 | 2.02 ± 0.26 | 2.39 ± 0.25 |
| | 10 | 1.00 ± 0.19 | 1.29 ± 0.36 | 1.78 ± 0.40 | 2.95 ± 0.16 |
| 18.7 | 0 | 1.00 ± 0.12 | 0.73 ± 0.17 | 0.51 ± 0.10 | 0.57 ± 0.01 |
| | 1 | 1.00 ± 0.12 | 1.18 ± 0.27 | 0.88 ± 0.18 | 1.76 ± 0.08 |
| | 5 | 1.00 ± 0.21 | 1.36 ± 0.24 | 2.02 ± 0.26 | 2.39 ± 0.25 |
| | 10 | 1.00 ± 0.06 | 1.86 ± 0.30 | 2.03 ± 0.37 | 2.64 ± 0.29 |

Normalized Metabolic Activity Values are in relative units (RU) (Mean ± standard deviation); n = 6 z-stacks from 3 hydrogels per condition

Example 8: Effect of Hydrogel Compositions & their Properties on the 3D Morphology of Cells/Cell Clusters Next, 3D morphology of cells/cell clusters in hydrogels with varying NVP and RGDS concentrations were quantified by staining for F-actin and nuclei and image analysis of confocal z-stacks. The cell/cluster metrics quantified are % single/clustered cells, % rounded/invasive cells, % non-invasive/invasive clusters and cluster density. These values for these metrics are summarized in Table 8.

TABLE 8

| [NVP] mM | [RGDS] mM | % single/clustered cells Day 15 | % rounded/invasive cells Day 15 | % non-invasive/invasive clustersers Day 15 | Clusters/mm³ Day 15 |
|---|---|---|---|---|---|
| 0.0 | 0 | 86.1/13.9 ± 6.3 | 99.0/1.0 ± 0.4 | 100.0/0.0 ± 0.0 | 349 ± 168 |
| | 1 | 27.8/72.2 ± 10.2 | 70.1/29.9 ± 8.2 | 20.9/79.1 ± 11.6 | 1713 ± 299 |
| | 5 | 8.8/91.2 ± 3.8 | 10.0/90.0 ± 1.0 | 6.3/93.8 ± 10.9 | 1275 ± 139 |
| | 10 | 2.4/97.6 ± 0.7 | 9.2/90.8 ± 2.1 | 2.8/97.2 ± 5.6 | 1414 ± 60 |
| 4.7 | 0 | 92.7/7.3 ± 3.2 | 99.9/0.1 ± 0.2 | 100.0/0.0 ± 0.0 | 159 ± 120 |
| | 1 | 69.7/30.3 ± 4.9 | 91.4/8.6 ± 4.2 | 76.7/23.3 ± 13.3 | 598 ± 120 |
| | 5 | 45.5/54.5 ± 6.0 | 52.4/47.6 ± 4.5 | 36.4/63.6 ± 3.6 | 1096 ± 60 |
| | 10 | 22.1/77.9 ± 6.3 | 66.9/33.1 ± 4.5 | 58.0/42.0 ± 4.0 | 1992 ± 299 |
| 9.4 | 0 | 95.8/4.2 ± 1.4 | 99.4/1.6 ± 0.8 | 100.0/0.0 ± 0.0 | 60 ± 20 |
| | 1 | 81.0/19.0 ± 8.0 | 95.5/4.6 ± 2.9 | 86.2/13.8 ± 6.9 | 578 ± 279 |
| | 5 | 60.1/39.9 ± 8.8 | 95.8/4.2 ± 1.4 | 80.8/19.2 ± 11.5 | 518 ± 199 |
| | 10 | 61.8/38.2 ± 5.5 | 89.4/10.6 ± 4.1 | 80.6/19.4 ± 3.2 | 1235 ± 199 |
| 18.7 | 0 | 83.0/17.0 ± 2.2 | 98.7/1.3 ± 0.4 | 100.0/0.0 ± 0.0 | 458 ± 80 |
| | 1 | 62.5/37.5 ± 7.6 | 93.1/6.9 ± 2.7 | 91.4/8.6 ± 2.9 | 1394 ± 120 |
| | 5 | 47.4/52.6 ± 5.4 | 87.1/12.9 ± 2.4 | 81.2/18.8 ± 1.4 | 1375 ± 179 |
| | 10 | 67.1/32.9 ± 8.1 | 88.9/11.1 ± 3.4 | 82.4/17.6 ± 12.2 | 1474 ± 239 |

Values represent % or number/mm³ (Mean ± standard deviation); n = 5 z-stacks from 3 hydrogels per condition Table 8 shows that in general, hydrogels with 0 mM NVP and increasing RGDS concentration had increasing percentages of single, invasive cells and invasive clusters. Cluster density was also high (>1000 clusters/mm³) in these formulations. This was due to increasing cell-matrix interactions leading to higher invasion, spreading and formation of cellular protrusions in matrices with high degradability and high porosity. In hydrogels with 0 mM RGDS, cells appeared as single, rounded cells with non-invasive dusters, primarily due to absence of matrix adhesivity. In hydrogels with 4.7 mM NVP with increasing RGDS, cells appeared as invasive cells and invasive clusters, indicating the role of RGDS in facilitating cell invasion. In hydrogels with 9.4 mM NVP and increasing RGDS, cells were restricted to single, rounded cells with non-invasive clusters, primarily owing to matrix confinement and high crosslink density. Interestingly, in hydrogels with 18.7 mM NVP, cells appeared in non-invasive dusters with high cluster density (>1000 clusters/mm³), irrespective of RGDS, indicating that matrix properties besides adhesivity (including stiffness) may also regulate 3D morphology of cancer cells. Overall, 3D cell morphology was dually modulated by both RGDS and NVP concentrations through a combination of matrix adhesivity, degradability, stiffness and matrix confinement.

Figure 2:
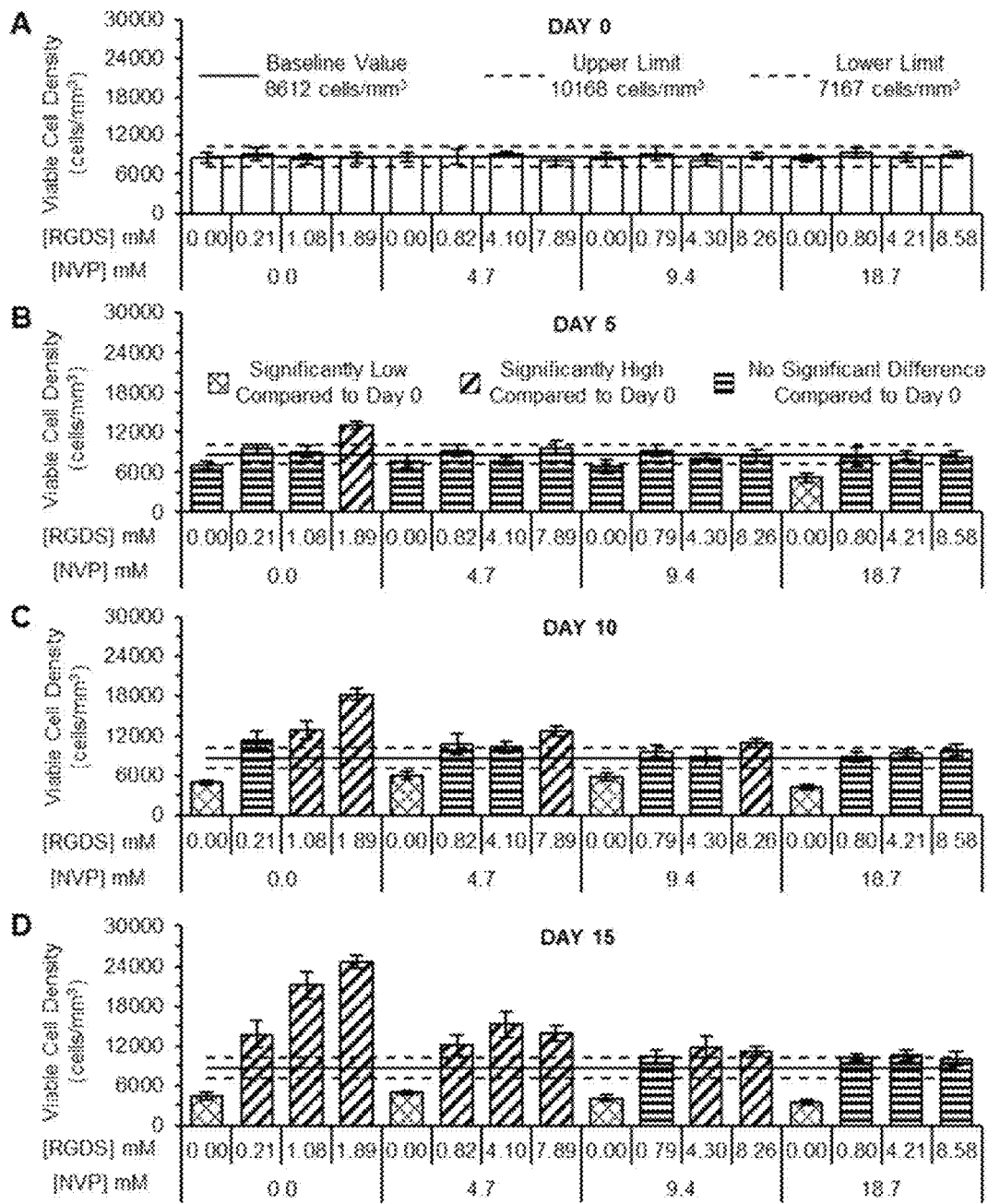
FIG. 2 shows the time evolution of viable cell density in crosslinked hydrogel compositions on days 0, 5, 10 and 15, as measured through fluorescent images of cells stained with calcein AM (live cells) and ethidium homodimer (dead cells). In particular, FIGS. 2A-2D display viable cell densities within crosslinked hydrogel compositions with varying NVP and RGDS concentrations. The baseline value (solid line) represents the mean of all groups on day 0. The upper and lower limit (dashed lines) represent the deviation/noise in the day 0 measurements. Statistically significant differences/no differences between values of each time point and corresponding day 0 values are indicated using striped patterns. Values represent mean± standard deviation. Difference is considered statistically significant when p-value<0.01, one-way ANOVA test; n=6 z-stacks from 3 hydrogels per condition.

Example 9: A Method of Phenotypically Classifying Hydrogel Compositions for Inducing Specific Cancer Cell State FIG. 3 shows a flow chart for a method to phenotypically classify crosslinked hydrogel compositions inducing cancer cell states corresponding to one of the four following groups: 1) invasive growth, 2) single cell restricted survival dormancy, 3) single cell balanced survival dormancy, and 4) tumor mass balanced survival dormancy (Table 1). As shown in FIG. 3, first, viable cell density in each hydrogel composition on day 15 was statistically compared to corresponding day 0 values, as shown in FIG. 2. Hydrogels with significantly higher viable cell densities were grouped into the 'invasive growth' category. These included hydrogels with 0-4.7 mM NVP and 1-10 mM RGDS and hydrogels with 9.4 mM NVP and 5-10 mM RGDS. The remaining hydrogels were compared for cell viability. When viability values on day 15 were less than 10% of day 0 values, hydrogels were classified as 'single cell restricted survival dormancy' state. These were hydrogels with 0 mM RGDS that underwent high degree of cell death, but remaining viable cells remained dormant and quiescent. Next, the remaining hydrogels were assessed for cell/cluster morphology. When single cells constituted >80% of total cells and clustered cells constituted <20% of total cells, corresponding hydrogel conditions were grouped into 'single cell balanced survival dormancy' and remaining hydrogel conditions were grouped into 'tumor mass balanced survival dormancy. Only one crosslinked hydrogel composition (one with 9.4 mM NVP and 1 mM RGDS) was classified into single cell balanced survival dormancy category. Hydrogels with 18.7 mM NVP and 1-10 mM RGDS were classified into tumor mass balanced survival dormancy (FIG. 3). Overall, these formulations provide perspective on designing of matrices for directing cancer cells toward specific fates.

Example 10: A Method of Phenotypically Switch Cancer Cells from One State to Another Next, the ability to phenotypically switch cancer cells from a dormant to an invasive growth state was demonstrated. Cells encapsulated in 0 mM NVP and 0 mM RGDS were maintained in 3D culture for 40 days during which they remained in single cell restricted survival dormancy state. On day 40, 10 mM PEG-RGDS was covalently coupled to the cell-encapsulating hydrogels via further UV exposure in the presence of LAP and maintained further for a total of 75 days. Evaluation of cell viability and proliferation was conducted every 15 days post encapsulation. Cell viability dropped significantly from day 0 to day 30 and increased again from day 45 onwards after addition of RGDS, thereby confirming that increase of matrix adhesivity can maintain and even increase cell viability in dormant cells. Proliferation remained low till day 30 and increased again from day 45 onwards, thereby indicating that RGDS conjugation leads to cell invasion and increased growth, as shown in FIG. 5. The ability to tune matrix properties in a temporal manner allows the study of dynamic and long-term cell responses within hydrogel matrices and simulates to some extent the metastatic relapse condition found in cancer patients.

Tuning of matrix properties can also be attempted using alternate strategies. In prior studies, we modulated UV exposure time (15 seconds-1 minute) and LAP concentration (1 mM-10 mM) in the polymer precursor in an attempt to obtain hydrogels with varying degrees of crosslink density and stiffness. However, we were unable to fabricate hydrogels with varying properties using this strategy due to high molar absorptivity of LAP and short sol-gel transition time.

Fabricated hydrogels can also be digested partially using enzymatic treatment (collagenase, trypsin, hyaluronidase etc.) to reduce crosslink density, and make the hydrogel more porous and permissive to encapsulated cancer cells. This strategy is also likely to produce similar results as described above and simulate the dormancy-proliferation switch.

Taken together, these results indicate that hydrogel properties can be modulated to induce cancer cells toward specific fates that range across overt invasive growth (simulating metastatic tumors), high cell death (simulating apoptotic DTCs in secondary microenvironments) and dormant states (simulating single dormant DTCs or dormant micrometastases).

Example 11: A Method of Screening for Drugs and Discovery of Biomarkers Against Tumor Dormancy and Metastatic Relapse FIG. 4 shows a flow chart of a method of screening for drugs and discovery of biomarkers against tumor dormancy and metastatic relapse. As shown in FIG. 4, this can be achieved using one of three routes: Route 1: Encapsulating cells in crosslinked hydrogel compositions supporting invasive growth, culturing the cells in 3D for 15 days, assessing cell metrics as described hereinabove, administering compound(s) of interest on the cancer cells and assessing therapeutic efficacy using end points assays (viability and viable cell density). Route 2: Encapsulating cells in crosslinked hydrogel compositions inducing single cell or tumor mass dormancy, culturing the cells in 3D for 15 days, verifying dormancy status as described above, administering compound(s) of interest on the cancer cells and assessing therapeutic efficacy using end points assay; Route 3: Encapsulating cells in crosslinked hydrogel compositions inducing single cell dormancy, reactivating cells toward invasive growth, administering compound(s) of interest on the reactivated cells and assessing therapeutic efficacy using end points assays. These strategies can provide useful information about therapeutic efficacies against cancer cells in different states (invasive growth or dormant state) and those transitioning between different states (dormancy to proliferative switch).

TABLE 9

| SEQ ID Numbers | Corresponding Peptide Sequences |
|---|---|
| SEQ ID NO: 1 | GGGPQGIWGQGK |
| SEQ ID NO: 2 | GGGIQQWGPGGK |
| SEQ ID NO: 3 | GGGGGIPQQWGK |
| SEQ ID NO: 4 | RGDS |
| SEQ ID NO: 5 | RDGS |
| SEQ ID NO: 6 | RGES |
| SEQ ID NO: 7 | REGS |
| SEQ ID NO: 8 | IKVAV |
| SEQ ID NO: 9 | VVIAK |
| SEQ ID NO: 10 | YIGSR |
| SEQ ID NO: 11 | YSRIG |
| SEQ ID NO: 12 | DGEA |
| SEQ ID NO: 13 | DAEG |

Example 12: A Method of Characterizing Chemoresistant Behavior of MDA-MB-231 Metastatic Breast Cancel Cells in Dormant Cells Compared to Cells in a Growth State Introduction:

Three hydrogel formulations that Induce growth, cellular dormancy, or balanced dormancy were used to characterize chemoresistant behavior of MDA-MB-231 cells in dormant cells compared to cells in a growth state. In particular, MDA-MB-231 cells were encapsulated and maintained in three-dimensional (3D) culture in each of the three hydrogel formulations:
  (i) growth (10 mM PEG-RGDS, 0 mM NVP),
  (ii) balanced dormancy (1 mM PEG-RGDS, 9.4 mM NVP), and
  (iii) cellular dormancy (0 mM PEG-RGDS, 0 mM NVP).

Tuning PEG-RGDS concentration altered adhesive ligand density of the hydrogel matrix required for integrin-mediated cell adhesion and survival and NVP incorporation increased the number on non-degradable crosslinks of the hydrogel matrix, inhibiting cell-mediated matrix degradation leading to physical confinement of encapsulated cells in their local niche.

Fifteen day post encapsulation, MDA-MB-231 cells were exposed to doxorubicin (DOX), paclitaxel (PAC), or 5-fluorouracil (5-FU) for 48 hr, followed by quantification of cell viability to assess the efficacy of each drug and to quantify differences in cellular responses among the three phenotypic states. For all three drugs tested, MDA-MB-231 cells undergoing either cellular- or balanced dormancy demonstrated significantly increased chemoresistance compared to MDA-MB-231 cells in the growth state.

For DOX, dormant cells had a 1.4 to 1.8-fold Increase in half maximal effective concentration ($EC_{50}$) and 1.3 to 1.8-fold Increase in $IC_{50}$ values compared to MDA-MB-231 cells in the growth state. Dormant MDA-MB-231 cells exposed to PAC displayed statistically significant higher cell viability compared to those in the growth state, with >72% of dormant cells viable compared to 39±4% when exposed to 1 mM PAC. Similarly, dormant cells exposed to 5-FU displayed significant increases in cell viability, with >93% cell viability in MDA-MB-231 cells residing in either dormant state, compared to 75±5% for cells in the grow state at 10 mM 5-FU.

To understand how chemoresistance to DOX was exhibited by dormant cells, the intracellular concentration of DOX was quantified via intensity measurements of DOX autofluorescence. No significant differences in the intracellular intensity (concentration) of DOX were observed but the intracellular distribution, as quantified by the nuclear to cytoplasmic (N/C) drug ratio, Indicated that dormant cells had a 1.5-fold decrease in relative DOX accumulation in the nuclei compared to MDA-MB-231 cells in the growth state; suggesting that dormancy-associated chemoresistance may be due to decreased drug nuclear localization, at least for DOX. These results demonstrate how tuning matrix properties alter MDA-MB-231 cell phenotype and subsequent chemoresistance, lends additional validation that this hydrogel platform can be used to induce breast cancer dormancy, and supports its use for future development and testing of new anti-dormancy therapeutic approaches.

Measuring Drug Responses—2D Controls

MDA-MB-231 cells were trypsinized, counted, and seeded in a fibronectin coated (10 μg/mL), 96 well plate at a density of 5,000 cells/well in serum-containing medium. To measure the drug response of cells independent of encapsulation, pre-encapsulation conditions were replicated by allowing the cells to adhere overnight followed by culture in serum-free medium for 48 hr. DOX, PAC, and 5-FU were reconstituted in DMSO to a stock concentration of 172.4, 58.5, and 384.6 mM, respectively. Stock solutions were diluted in medium to a range of concentrations: DOX (0.001, 0.01, 0.1, 1, 10, 100, or 1000 μM), PAC (0.001, 0.01, 0.1, 1, 10, or 100 μM), and 5-FU (0.001, 0.01, 0.1, 1, 10, 100, or 1000 μM) and added to the MDA-MB-231 cells for 48 hr (n=6 wells per concentration). 46 At the highest drug concentration tested, the DMSO concentration remained 50.1% (v/v); thus, 0.1% (v/v) DMSO was used as a vehicle control in 2D studies. Cells were rinsed in PBS twice to remove excess medium, followed by labeling with a Live/Dead® cell viability kit (Invitrogen). Only live cells were labeled, as dead cells detached from the wells and were washed away. Labeled cells were imaged using the proper filter cubes and analyzed using FIJI software (NIH).

Measuring Drug Responses—Cells Cultured in Hydrogels

DOX, PAC, and 5-FU stocks were diluted in medium to desired concentrations: DOX (0.001, 0.01, 0.05, 0.1, 0.55, 1, or 2 mM), PAC (0.05, 0.1, 0.55, or 1 mM), and 5-FU (1.0, 4.0, 7.0, or 10 mM).

At the highest concentrations tested, the DMSO concentration ranged between 1-2% (v/v) for all drugs used. A vehicle study was conducted and showed no significant differences in cell viability between I or 2% (v/v) DMSO and serum-containing medium (FIG. 20). Thus, all vehicle controls used in this study contained medium with 1% (v/v) DMSO. We also tested higher concentrations (18%, 26% (v/v)) of DMSO required to use higher doses of PAC and 5-FU, however these concentrations were cytotoxic to MDA-MB-231 cells (FIG. 20). 15 days post encapsulation, cell-laden hydrogels were rinsed with PBS and transferred to a new well plate for drug exposure for 48 hr. The hydrogels were rinsed twice with PBS to remove excess medium, followed by labeling with a Live/Dead® cell viability kit (Invitrogen) in PBS for 30 min, according to the manufacturer's instructions. The hydrogels were rinsed with PBS for 10 min to remove excess stain. Labeled hydrogels were placed on coverslips and imaged using structured Illumination on a Zeiss AxioObserver Z1 inverted fluorescent microscope as previously described. 32-34 Fluorescent z-stacks (z-height: 150 μm) were acquired approximately at the center of the hydrogels, between the bottom and top surfaces of each sample, and analyzed using FIJI software (NIH). Due to the red autofluorescence of DOX, only the live cells were imaged for viability studies. To quantify cell viability, the number of live cells was normalized to the number of live cells measured in the vehicle control. A minimum of 6 hydrogels were analyzed for each condition.

Doxorubicin Accumulation Studies

Cells were encapsulated in hydrogel formulations that induced growth, balanced dormancy, or cellular dormancy for 15 days as described above. The medium was replaced with DOX-containing medium at a concentration of 0.05 mM. Four hydrogels for each formulation were imaged at varying time points (1, 2, 3, 5, 12, 20, 24, 48 hr). The mean cellular fluorescence intensity was measured and plotted against time to quantify intracellular DOX accumulation. To calculate the nuclear to cytoplasmic ratio, the fluorescence intensity measurements of the cytoplasmic and nuclear regions were acquired for each cell, with at least 70 cells measured per image. Due to its mechanism of action, DOX is known to primarily localize to the nucleus of DOX-sensitive cell lines. Studies quantifying DOX localization in multiple cell lines show alignment between high fluorescence intensity and the nucleus. Additionally, nuclear location was approximated based on areas of high fluorescence intensity with distinct morphological features (size, location).

Statistical Analysis

For statistical comparison between viability values, distribution normality was assessed via quantification of skewness and kurtosis, where values within ±2 indicated a normal distribution. Equal variance among groups was additionally evaluated. A one-way analysis of variance (ANOVA) with a post-hoc Tukey-Kramer test was implemented to determine statistical significance between multiple groups. Unless otherwise Indicated, p<0.05 was considered statistically significant. Origin Lab software was used to fit DOX viability data. A nonlinear, growth/sigmoidal curve fit using a dose response function with a Levenberg Marquardt iteration algorithm was performed and allowed to converge for all conditions with a chi-square tolerance of 1E-9.

Response of MDA-MB-231s to Doxorubicin, Paclitaxel, and 5-Fluorouracil in 2D Culture The response of MDA-MB-231 cells cultured on standard tissue culture plastic (2D) to DOX, PAC, and 5-FU was quantified as control. MDA-MB-231 cells were cultured on 96 well plates and serum-starved for 48 hr, following the same protocol used for encapsulation for ease of comparison. The MDA-MB-231 cells were exposed to drug-containing medium at the following concentrations (DOX: 0.001, 0.01, 0.1, 1, 10, 100, or 1000 µM; PAC: 0.001, 0.01, 0.1, 1, 10, or 100 µM; and 5-FU: 0.001, 0.01, 0.1, 1, 10, 100, or 1000 µM) for 48 hr. The live MDA-MB-231 cells were fluorescently labeled, imaged, and quantified (FIG. 1).

As expected, MDA-MB-231 cells demonstrated significant decreases in cell viability with increased drug concentration for all three drugs tested. DOX was the most effective, followed by PAC, and 5-FU (FIG. 8). The results demonstrate that viability decreased to 37 f 9% at 0.01 µM before gradually dropping to 1±0% at 100 µM for DOX (FIG. 8A). Fitting the dose-response curve for DOX resulted in an $EC_{50}$ of 0.006 µM and $IC_{50}$ of 0.007 µM (FIG. 8B). PAC was less effective than DOX. At 0.01 µM, viability remained high at 94±13%, but decreased to 6±2% at the highest concentration tested (100 µM) (FIG. 8A). Calculated $EC_{50}$ (0.716 µM) and $IC_{50}$ (0.651 µM) values were higher for PAC compared to DOX (FIG. 8B). 5-FU was the least effective with an $EC_{50}$ of 1.81 µM and with 65±3% of the cell population viable at the highest dosage of 1 mM (FIG. 8). An $IC_{50}$ could not be calculated for 5-FU, as viability did not drop below 65% (FIG. 8B).

Hydrogel Characterization & 231 Phenotypic Definitions

Three hydrogel formulations that allowed for induction of three different MDA-MB-231 cell phenotypes were used: (1) a growth formulation containing high ligand density (10 mM PEG-RGDS) and high degradability (0.01 min-1), (2) a balanced dormancy formulation containing lower adhesivity (1 mM PEG-RGDS) and lower degradability (0.005 min-1) achieved by the addition of the non-degradable NVP (9.4 mM), and (3) a cellular dormancy formulation with no adhesivity (0 mM PEG-RGDS) and high degradability (0.01 min-1) (FIG. 9A,C). NVP incorporation increases the crosslinking density through addition of non-degradable monomers resulting in an increased compressive modulus and lower degradability (FIG. 9). Limiting PEG-RGDS concentration Inhibits integrin-mediated adhesion, while NVP incorporation decreases matrix degradability leading to increased confinement. Tuning these properties mediates cell-matrix interactions necessary for controlling cellular phenotype.

The response of MDA-MB-231 cells to the three hydrogel formulations was measured to verify hydrogel-induced changes in phenotype. The growth state was defined when statistically significant increases in the ratio of actively proliferating cells, metabolic activity, and density of new live cells compared to new dead cells at day 15 relative to day 0 were observed (FIG. 9D). The majority of cells residing in this state existed as invasive cell dusters (FIG. 9B). Balanced dormancy was defined when a balance in the density of new live and dead cells post day 0 was achieved (indicated by a ~1:1 live:dead cell ratio) indicating that the increase in density of live cells was nearly perfectly balanced by the increase in density of dead cells over 15 days preventing growth of larger micrometastases as observed in the growth formulation. Cells in this state presented a rounded morphology (FIG. 9B). Cellular dormancy was defined by low proliferation, no statistically significant increase in metabolic activity at day 15 relative to day 0, and no new live cells at day. Cells in this state existed as solitary, rounded cells (FIG. 9B). Hydrogels formulations that induced each of these phenotypic states were used for all drug response studies presented (FIG. 9A).

Response of MDA-MB-231s to Doxorubicin

Measured cellular metrics used to define phenotypic states demonstrate the ability to induce breast cancer dormancy using engineered hydrogels. It is well established that dormant cells often display increased chemoresistance. To quantify the degree of chemoresistance imparted on MDA-MB-231 cells in dormant states compared to the growth state, the response of MDA-MB-231 cells cultured in the three hydrogel formulations to DOX was quantified. Post encapsulation, the cells were cultured for 15 days in the desired hydrogel formulation to provide enough time for the cells to respond to the hydrogel properties; culturing for longer time periods did not significantly alter phenotype. Cells were exposed to DOX (0.001-2 mM) for 48 hr and cell viability quantified (FIG. 10A, B). To assess the drug-response of MDA-MB-231 cells in the three phenotypic states, the cells were labeled with Calcein AM to fluorescently label live cells, imaged (FIG. 10A), and the number of live cells normalized to the vehicle control (media containing 1% DMSO) to quantify cell viability (FIG. 10B).

MDA-MB-231 cells cultured in the hydrogel formulation that induced cellular dormancy displayed statistically significant higher viability than MDA-MB-231 cells cultured in the growth formulation for DOX concentrations ranging from 0.001 to 1 mM (FIG. 38). For instance, at 0.01 and 0.05 mM, viability remained 91±12% and 62±5% for cells undergoing cellular dormancy and 82±1% and 44±3% for cells in the growth state respectively (FIG. 10B). Increased differences in viability were observed at higher concentrations (0.55, 1.00 mM) where viability was 4-6 times higher for cells undergoing cellular dormancy compared to those in the growth state (FIG. 10B). For example, at 0.55 mM, dormant MDA-MB-231 cells remained 24±3% viable compared to 5±1% in the growth state (FIG. 10B). MDA-MB-231 cells undergoing balanced dormancy also displayed higher viability compared to MDA-MB-231 cells in the growth state over a range of concentrations, with significant differences observed at 0.05 mM (balanced dormancy:growth, 57±2%: 44±3%) and 0.55 mM (balanced dormancy:growth, 16±1%: 5±1%) (FIG. 38).

Dose response curves were fit to the viability data for the growth and two dormant states to quantify $EC_{50}$ and $IC_{50}$ values (FIG. 10C). $EC_{50}$ and $IC_{50}$ values from MDA-MB-231 cells in 2D culture were much lower compared to cells cultured in hydrogels as expected (FIG. 8B, 10C). In 2D culture, DOX had $EC_{50}$ and $IC_{50}$ values of 0.006 and 0.007 µM, respectively, while the $EC_{50}$ values for cells in the three hydrogel formulations ranged between 47.4-83.3 µM with $IC_{50}$ values from 43.6-79.9 µM (FIG. 8B, 10C). Specifically, MDA-MB-231 cells in the growth state had an $EC_{50}$ of 43.6 µM, while those undergoing balanced dormancy or cellular dormancy had higher $EC_{50}$ values of 67.6 and 83.3 µM respectively (FIG. 10C). Similarly, $IC_{50}$ values followed the same trend (growth: 43.6, balanced dormancy: 58.3, cellular dormancy: 79.9 µM) (FIG. 10C). Together, this data Indicates that MDA-MB-231 cells in either dormant state exhibited significantly higher chemoresistance to DOX compared to cells in the growth state. In particular, MDA-MB-231 cells undergoing cellular dormancy maintained overall higher viability than those undergoing balanced dormancy, as indicated by the higher $EC_{50}$ and $IC_{50}$ values (FIG. 10C).

Response of MDA-MB-231s to Paclitaxel

To assess the chemoresistance of dormant MDA-MB-231 cells to other common breast cancer drugs, encapsulated cells were cultured for 15 days and exposed to varying concentrations of PAC for 48 hr. As described above, the live cells were fluorescently labeled with Calcein AM, imaged, counted, and normalized to the vehicle control for each hydrogel formulation (FIG. 11A,B). 2D studies demonstrated that compared to DOX, PAC was less effective (FIG. 8A,B) and therefore required a higher concentration to achieve comparable cellular response as DOX. MDA-MB-231 cells undergoing cellular dormancy had statistically significant higher viability for most PAC concentrations compared to MDA-MB-231 cells in the growth state. For instance, at 0.10 and 0.55 mM, MDA-MB-231 cells undergoing cellular dormancy remained 91±6% and 84±5% viable compared to 55±4% and 51±4% for cells in the growth state respectively (FIG. 11B). Furthermore, at the highest PAC concentration tested (1 mM), 75±3% of cells undergoing cellular dormancy remained viable while only 39±4% of cells in the growth state were viable (FIG. 11B).

Similar to the trend observed with DOX, MDA-MB-231 cells undergoing balanced dormancy exhibited significant chemoresistance to PAC. For example, at 0.55 mM and 1.00 mM, viability was 86±5% and 72±3% for cells undergoing balanced dormancy, and 51±4% and 39±4% for cells in the growth state respectively. There were no statistically significant differences in viability between dormant states for any concentration of PAC tested (FIG. 11B).

Response of MDA-MB-231s to 5-Fluorouracil

The effect of a third, commonly used breast cancer drug, 5-FU on MDA-MB-231 cells was evaluated in the three phenotypic states. The same protocol was followed to encapsulate, label, image, and quantify live cells in the growth, single cell dormancy, and balanced dormancy states. Compared to both DOX and PAC, the 2D studies indicated that 5-FU was the least effective and therefore required a higher concentration (FIG. 8 A,B), which were limited by DMSO toxicity as discussed. Nonetheless, a significant increase in chemoresistance was observed for MDA-MB-231 cells undergoing cellular or balanced dormancy compared to those in the growth state (FIG. 12 A,B).

At 1 mM, MDA-MB-231 cells remained highly viable in all three hydrogel formulations. However, at 4 mM, MDA-MB-231 cells in the growth state decreased to 86-7% viability while those undergoing cellular dormancy remained 100±6% viable with MDA-MB-231 cells undergoing balanced dormancy displaying 92±4% viability (FIG. 128). A similar trend was observed at 7 mM, with MDA-MB-231 cells in the growth state further decreasing to 80±2% viability while cells in both dormant states remained >90% viable (FIG. 128). At the highest concentration tested (10 mM) MDA-MB-231 cells undergoing cellular dormancy were 99±4% viable compared to only 75±5% for those in the growth state (FIG. 128). No statistically significant differences were measured between MDA-MB-231 cells in either dormant state (FIG. 128). These results indicate that dormant MDA-MB-231 cells remain >90% viable at all concentrations of 5-FU tested and display greater chemoresistance to 5-FU than MDA-MB-231 cells in the growth state (FIG. 128).

Doxorubicin Accumulation and Localization

To determine the cause of increased chemoresistance to DOX displayed by dormant MDA-MB-231 cells compared to those in the growth state, we took advantage of DOX autofluorescence to quantify intracellular drug accumulation (FIGS. 12A, 8). Cell-laden hydrogels were exposed to DOX (0.05 mM) and imaged at 1, 2, 3, 5, 12, 20, 24, and 48 hr post exposure (FIG. 13A). Image analysis was used to measure the mean intracellular fluorescence intensity of DOX in MDA-MB-231 cells cultured in the three hydrogel formulations over time (FIG. 13B). Note, while cells in the growth formulation appear invasive after 15 days in culture, they revert to a rounded morphology after 48 hr DOX exposure. The results demonstrate that DOX steadily increased in MDA-MB-231 cells with no statistically significant differences between MDA-MB-231 cells in the three phenotypic states (FIG. 13B). This data suggests that drug uptake and efflux was similar in MDA-MB-231 cells in all three phenotypic states and therefore did not play a role in the observed chemoresistance in cells undergoing dormancy.

To quantify potential differences in the intracellular distribution of DOX, the nuclear to cytoplasmic (N/C) ratio was calculated by measuring the mean fluorescence intensity of DOX in the cytoplasm and nucleus of each cell (FIG. 13C). Since DOX binds to DNA In the nucleus, it is known to preferentially localize to the nucleus of DOX-sensitive cell lines, with several studies indicating alignment between nuclear staining and areas of high DOX fluorescence intensity. Thus, here we approximated that areas of high fluorescence intensity with distinct nuclear morphologies corresponded to nuclear localization of DOX. The N/C ratio was 3.5±2.3 for the growth state, 2.3±0.8 for cells undergoing balanced dormancy, and 2.4±1.0 for cells undergoing cellular dormancy (FIG. 13C). The data demonstrates that dormant MDA-MB-231 cells had a 1.5-fold decrease in DOX nuclear localization compared to those in the growth state (FIG. 13C). Since DOX induces DNA damage and cell death via methods including intercalation into DNA, this data suggests there is more DNA-bound doxorubicin in MDA-MB-231 cells in the growth state compared to those undergoing dormancy. Therefore, while DOX equally accumulates in dormant cells, less drug localizes to the nucleus, leading to an increased chemoresistance in dormant MDA-MB-231 cells.

Discussion

Control studies were performed in 2D to assess MDA-MB-231 cells' drug response to DOX, PAC, and 5-FU (FIG. 8). Following the same protocol used for encapsulation, MDA-MB-231 cells were cultured, serum starved for 48 hr, and exposed to common breast cancer drugs, DOX, PAC, or 5-FU for 48 hr. Viability data demonstrates $IC_{50}$ values of 0.007 and 0.651 µM for DOX and PAC respectively (FIG. 8, Table 10) and $EC_{50}$ values of 0.006, 0.761, and 1.810 µM for DOX, PAC, and 5-FU respectively (FIG. 8, Table 10) which are comparable to previously reported values from 2D studies. For 3D studies, MDA-MB-231 cells were cultured for 15 days in the three hydrogel formulations and cells undergoing growth, balanced dormancy, or cellular dormancy were exposed to DOX, PAC, or 5-FU, for 48 hr. Viability assays were conducted to quantify the response to each drug (FIGS. 10A, 11A, 12A). As expected, MDA-MB-231 cells in 3D were less sensitive to drugs compared to 2D culture. Differences between 2D and 3D systems in the context of drug screening have previously been reviewed and it is accepted that 3D drug platforms better represent drug responses observed in vivo. Cells may respond differently to drugs in 3D due to oxygen gradients similar to those in in vivo tumors, spatial organization of cell surface receptors, matrix diffusion, and physical constraints that influence gene expression. Differences in present system may be do physical constraints imparted by the matrix and spatial organization of encapsulated cells. However, without wishing to be bound by any particular theory, it is believed that one would not expect there to be oxygen gradients or transport limitations since hydrogels are only 500 μm in thickness, which is below the distance range necessary to form these gradients. Additionally, there are no limitations in drug transport as drugs, used in the present exemplary embodiment, are small molecules with molecular weights ranging from 130 to 854 g/mol. For instance, doxorubicin was estimated to be <2 nm in diameter using a molecular model. Additionally, molecules of similar molecular weights do not exceed 2 nm in size. The average mesh size of the hydrogels used to induce growth and cellular dormancy states in these studies was 69±5 nm and 55±4 nm for the balanced dormancy hydrogel formulation. Since the drugs used here were an order of magnitude smaller than the hydrogel mesh size, high levels of diffusion throughout the hydrogel are anticipated.

TABLE 10

Drug sensitivty of MDA-MB-231 cells cultured from 2D studies

| Quantified Parameter (μM) | Doxorubicin | Paclitaxel | 5-Fluorouracil |
| --- | --- | --- | --- |
| $IC_{50}$ | 0.007 | 0.651 | — |
| $EC_{50}$ | 0.006 | 0.716 | 1.810 |

(n = 6 images from 6 individual wells)

Changes in drug response were also observed between MDA-MB-231 cells undergoing cellular dormancy, balanced dormancy, or growth. For exposure to DOX, cells in either dormant state displayed significantly higher viability than cells in the active growth state for a majority of the concentrations tested (FIG. 8B). Fits to the dose-response curves demonstrated that cells undergoing balanced or cellular dormancy had a 1.3- and 1.8-fold increase respectively in $IC_{50}$ values compared to actively proliferating cells in the growth state (FIG. 10C). This indicates that a higher dosage of DOX is required to induce 50% death in dormant cells compared to actively proliferating cells. While our $IC_{50}$ and $EC_{50}$ values fall within the range of other 3D DOX studies, it is worth noting that current $IC_{50}$ and $EC_{50}$ values reported in 3D drug studies vary significantly in magnitude, due to differences in key factors including matrix properties, experiment duration, and cell growth rates. Similar results were seen in PAC and 5-FU (FIG. 4,5). In both cases, dormant cells in either state had significantly higher viability than those in the growth state. PAC and 5-FU were less effective in reducing cell viability and therefore required higher concentrations (FIG. 1, 4, 5). Even though all drugs tested were dissolved in minimal DMSO according to solubility, higher drug doses were not tested as higher doses would lead to cytotoxic effects from DMSO alone and confound Interpretation of the results. Therefore, a dose-response curve for these drugs could not be generated, however, the viability data demonstrates that cells in either dormant state showed significant chemoresistance to PAC and 5-FU, similar to DOX (FIG. 11,12). These results agree with prior art data that Indicates dormant cells show increased chemoresistance in vivo and in vitro. This data also serves to further validate the ability to induce dormant states using engineered hydrogels composed of simple components as demonstrated here.

All drugs used in an exemplary embodiment of the present invention target proliferating cells using various mechanisms. DOX interferes with the cell cycle by preventing DNA replication via intercalation and inhibition of topoisomerase II. Additionally, DOX can be oxidized to a semiquinone radical, that can generate reactive oxygen species causing DNA damage. PAC disrupts proliferating cells by preventing microtubule disassembly during mitosis. 5-FU inhibits RNA transcription and interferes with DNA synthesis. Cells unable to proliferate due to DNA damage will activate apoptotic mechanisms during cell cycle check points. Furthermore, cancer cells often have inhibited or deficient repair mechanisms that prevent them from repairing damaged DNA. According to the fractional kill theory, a drug will only eliminate those cells that pass through the relevant cell cycle phase during drug exposure. Positive correlations between clinical response of DNA-targeted chemotherapy and rate of proliferation support this theory. Thus, DOX, and other cancer drugs, preferentially target proliferating cells and may even kill rapidly dividing cells that are not cancerous such as blood cells in the bone marrow. Therefore, dormant cells in a quiescent state (G0-G1 arrest) that are slow cycling, such as those in this study, would not be susceptible to drug-induced death for drugs that target cell division. Dormancy-associated resistance is supported by multiple patient studies that indicate dormant DTCs are resistant to common forms of chemotherapy.

Studies that quantify DOX accumulation and localization have been used to understand chemoresistance mechanisms. To test if drugs accumulated differently in dormant MDA-MB-231 cells compared to those in the growth state, DOX autofluorescence was implemented to quantify drug accumulation by temporally measuring the intracellular fluorescence intensity (concentration) of DOX over 48 hr. The results indicated no significant differences in intracellular concentration, and therefore, doxorubicin accumulation between actively proliferating and dormant cells (FIG. 13A, B). These results indicate that drug accumulation (difference in uptake and efflux) was similar for MDA-MB-231 cells in all three phenotypic states. If dormant MDA-MB-231 cells used efflux pumps that actively expel DOX out of the cell, similar to known chemoresistant cells, we would expect accumulation to be less in MDA-MB-231 cells undergoing dormancy. However, this data indicates drug accumulation does not play a role in dormant MDA-MB-231 cell chemoresistance, at least for DOX.

While drug accumulation can indicate if DOX made it into a cell, translocation into the nucleus better indicates its chemotherapeutic effect since DOX works by intercalating into DNA.55, 56 To measure this, the N/C ratio was calculated by measuring the DOX fluorescence Intensity in the nucleus and cytoplasm of each cell (FIG. 13C). Data showed that dormant MDA-MB-231 cells had a 1.5-fold decrease in DOX nuclear localization compared to those in the growth state (N/C ratio:growth:3.5±2.3; balanced dormancy: 2.3±0.8; cellular dormancy:2.4±1.0) (FIG. 13C). Since DOX can passively diffuse across the cell, this data suggests DOX equally accumulates in MDA-MB-231 cells undergoing dormancy or growth; however drug distribution within the cell leads to a difference in chemotherapeutic response.

Since proliferation is low in dormant cells, likely leading to lower DNA content, it is possible that dormant cells are simply less susceptible to DOX cytotoxicity since there are fewer binding sites available. Furthermore, since dormant cells are not progressing through the cell cycle, DOX that does accumulate in dormant cells is likely to have lesser cytotoxic affects. This may also contribute to why dormant cells in our platform show increased chemoresistance to DOX. Further experiments are required to confirm this theory. Some studies have suggested that dormant cells may additionally employ other survival pathways to resist treatment. For instance, endoplasmic reticulum (ER) stress can activate pERK signaling and downstream activation of transcription factors that relieve drug-induced stress. Additionally, the unfolded protein response (UPR) can downregulate topolsomerase II expression, leading to DOX resistance. Future experiments need to be conducted to determine if these responses are playing a role in maintaining dormant cell survival during treatment.

Example 13: Effect of Hydrogel Compositions & their Properties on the Cancer Cell Proliferation, Viable Cell Density, Metabolic Activity of Cells, and the 3D Morphology of Cells/Cell Clusters for Cancer Cell Lines of Bone, Lung and Brain Similar procedure and metrics as used for breast cancer MDA-MB-231 cells were used to study the effect of hydrogel composition and properties on the cancer cell proliferation, viability, metabolic activity and morphology of cell lines for bone, lung and brain cancer and the data Is shown in FIGS. 14-20 and Table 11. In particular, gel 1 represents invasive growth in bone, lung, and brain lines; gel 2 represents tumor mass dormancy in bone and brain-tropic cells, and balanced survival single cell dormancy in lung-tropic cells; and gel 3 represents balanced survival single cell dormancy in bone, lung, and brain-tropic lines.

FIG. 9 displays characterization of hydrogel used for studying bone, lung, and brain cancer cells. FIG. 9 clearly shows that varying amounts of RGDS and NVP alters matrix mechanical properties. In particular, adding NVP as done in the balanced dormant state, increases modulus while decreasing degradation rate, RGDS incorporation, mesh size, and swelling ratio.

FIG. 14 displays cell viability. In particular, the teachings from FIGS. 14A-14C can be summarized as:
  (i) Parental line: gel 1 has high viability, increase in viable cells; gel 2: high viability, increase in viable cells; gel 3: low viability, decrease in viable cells
  (ii) Bone, lung, brain: gel 1 has high viability, no change in viable cells; gel 2 high viability, no change in viable cells; gel 3 high viability, no change in viable cells FIG. 15 displays analysis of the cell & cell cluster morphology.

FIG. 16 displays cell proliferation and metabolism. In particular, the teachings from FIGS. 16A-16D can be summarized as:
  (i) Parental line: gel 1 has highest proliferation, increased EdU+ cells; gel 2: no change in EdU+ cells; gel 3: low proliferation, decreased EdU+ cells
  (ii) Bone, brain: gel 1 has highest proliferation, increased EdU+ cells; gel 2: increase in EdU+ cells; gel 3: no change EdU+ cells
  (iii) Lung: gel 1 has highest proliferation, increased EdU+ cells; gel 2: no change in EdU+cells; gel 3: no change EdU+ cells FIG. 17 displays early apoptosis. In particular, FIGS. 18A-18C shows that all cell lines increased apoptotic cell lines, though overall % remained low (<22%) in gels 1, 2, and 3—except for the parental line in gel 3—which corresponds with low viability levels seen previously.

FIG. 18 displays quantification of cell survival and death. In particular, the teachings from FIGS. 18A-18B can be summarized as:
  (i) Parental line: gel 1: increases in new live cells & EdU+ cells; gel 2: no change in in new live or EdU+ cells; gel 3:0 new live cells & decrease in EdU+ cells
  (ii) Bone: gel 1: increases in new live cells & EdU+ cells; gel 2: no change in new live, increase in EdU+ cells; gel 3: no change in new live cells or decrease in EdU+ cells
  (iii) Brain, Lung: gel 1: increases in new live cells & EdU+ cells; gel 2: no change in in new live or EdU+ cells; gel 3: no change in new live cells or decrease in EdU+ cells

TABLE 11

Quantitative metrics characterizing the behavior of parental MDA-M8-231, bone-tropic, lung tropic and brain tropic cell lines for classification into various cell states.

|  |  | Parental | Bone | Lung | Brain |
|---|---|---|---|---|---|
| Gel 1 | Viable Cell Ratio | *1.7 ± 0.1* | *1.5 ± 0. 3* | *1.6 ± 0.3* | *1.9 ± 0.4* |
|  | New live: dead | *18.7 ± 5.8* | *18.8 ± 9.9* | *13.8 ± 4.3* | *18.9 ± 8.1* |
|  | Edu+ Ratio | *6.1 ± 0.6* | *5.3 ± 1.4* | *3.4 ± 0.8* | *4.3 ± 1.7* |
|  | Edu+: AnnV+ | *7.1 ± 0.8* | *4.6 ± 1.0* | *3.8 ± 1.1* | *3.6 ± 1.7* |
|  | Metabolism | *12.5 ± 0.5* | *8.8 ± 1.9* | *5.9 ± 1.0* | *6.1 ± 1.0* |
|  | % Rounded Cells | 9.2 ± 2.1 | 1.7 ± 0.5 | 1.4 ± 0.6 | 2.8 ± 0.8 |
|  | % Clusters | 97.6 ± 0.7 | 97.8 ± 0.8 | 95.5 ± 2.7 | 96.8 ± 0.7 |
| Gel 2 | Viable Cell Ratio | 1.0 ± 0.05 | 1.2 ± 0.1 | 1.0 ± 0.1 | 1.2 ± 0.3 |
|  | New live: dead | 1.2 ± 0.3 | 1.5 ± 1.3 | 1.6 ± 1.2 | 1.8 ± 1.5 |
|  | Edu+ Ratio | 0.8 ± 0.4 | *1.9 ± 0.4* | 1.3 ± 0.6 | *2.1 ± 1.7* |
|  | Edu+: AnnV+ | 0.5 ± 0.3* | *1.4 ± 0.3* | 1.2 ± 0.6 | 1.2 ± 1.1 |
|  | Metabolism | 1.2 ± 0.4 | 1.7 ± 0.5 | 1.7 ± 0.5 | 1.3 ± 0.3 |
|  | % Rounded Cells | 95.5 ± 2.9 | 99.9 ± 0.1 | 99.5 ± 0.3 | 95.9 ± 3.0 |
|  | % Clusters | 19.0 ± 8.0 | 91.9 ± 4.6 | 23.5 ± 3.9 | 92.5 ± 2.8 |
| Gel 3 | Viable Cell Ratio | 0.4 ± 0.03* | 1.0 ± 0.1 | 1.0 ± 0.03 | 1.0 ± 0.1 |
|  | New live: dead | 0* | 1.8 ± 1.7 | 1.3 ± 1.2 | 1.5 ± 0.5 |
|  | Edu+ Ratio | 0.6 ± 0.1* | 0.9 ± 0.1 | 0.8 ± 0.4 | 1.4 ± 0.4 |
|  | Edu+: AnnV+ | 0.21 ± 0.02* | 1.5 ± 0.4 | 0.9 ± 0.5 | 0.8 ± 0.2 |
|  | metabolism | 1.0 ± 0.3 | 1.3 ± 0.4 | 1.2 ± 0.5 | 0.8 ± 0.3 |
|  | % Rounded Cells | 99.0 ± 0.4 | 99.8 ± 0.3 | 99.8 ± 0.2 | 99.8 ± 0.3 |
|  | % Clusters | 13.9 ± 6.3 | 6.8 ± 1.0 | 5.1 ± 2.3 | 9.8 ± 0.1 |

Note:
Italicized text represents Growth and Bold text represents Dormancy

Viable cell ratio: Ratio of cell viability values on day 15 compared to day 0

New live:dead: Ratio of number of new live cells formed from day 0 to day 15 compared to number of cells died from day 0 to day 15

EdU+ratio: Ratio of cells staining positive for EdU on day 15 compared to day 0

Edu+:AnnV+: Ratio of EdU+ cells to Annexin V+ cells on day 15

Metabolism: Normalized metabolic activity values based on day 0 values

% Rounded Cells: Percentage of cells quantified as having a rounded shape (circularity greater than 0.8)

% Clusters: Percentage of cells appearing as clusters of 3 or more cells in contact with each other

What is claimed:

1. A method of regulating a state of cancer cells, the method comprising:
   i) providing a system comprising:
      a) a crosslinked poly(ethylene glycol) (PEG)-based hydrogel composition comprising an acrylate-polymer-peptide macromer and a Type 1 ultraviolet (UV) photoinitiator, wherein the acrylate-polymer-peptide macromer comprises a first peptide and a first acrylate-PEG polymer covalently conjugated with the first peptide, wherein the first peptide consists of the sequence of X1-X2-X3-X4-X5-X6-X7-X8-X9-X10-X11, and wherein each of the X1 to X11 is G, P, Q, W, I or K,
      b) a cell culture medium in contact with the crosslinked PEG-based hydrogel composition, and
      c) cancer cells in contact with the cell culture medium and encapsulated in the crosslinked PEG-based hydrogel composition, wherein the cancer cells are in cell restricted survival dormancy; and
   ii) photopolymerizing a cell-adhesive macromer at 2-20 mM with the crosslinked PEG-based hydrogel composition, and thereby the cancer cells are induced to switch from the cell restricted survival dormancy to invasive growth,
   wherein the cell-adhesive macromer comprises a cell-adhesive peptide and a second acrylate-poly(ethylene glycol) (PEG) covalently conjugated with the cell-adhesive peptide, wherein the cell-adhesive peptide comprises a second peptide selected from the group consisting of RGDS (SEQ ID NO: 4), RDGS (SEQ ID NO: 5), RGES (SEQ ID NO: 6), REGS (SEQ ID NO: 7), IKVAV (SEQ ID NO: 8), VVIAK (SEQ ID NO: 9), YIGSR (SEQ ID NO: 10), YSRIG (SEQ ID NO: 11), DGEA (SEQ ID NO: 12), DAEG (SEQ ID NO: 13), and combinations thereof.

2. The method according to claim 1, wherein the first peptide is selected from the group consisting of GGGPQGIWGQGK (SEQ ID NO: 1), GGGIQQWGPGGK (SEQ ID NO: 2), GGGGGIPQQWGK (SEQ ID NO: 3) and combinations thereof.

3. The method according to claim 1, wherein the cancer cells are from an established cell line representing breast cancer, ovarian cancer, prostate cancer, colorectal cancer, bone cancer, lung cancer, or brain cancer.

4. The method according to claim 1, wherein the cancer cells are derived from a tumor patient and are patient-derived tumor cells.

5. The method according to claim 1, wherein each of the first and the second acrylate PEG is selected from the group consisting of acrylate-PEG-succinimidyl valerate (PEG-SVA), acrylate-PEG-N-hydroxylsuccinimide (PEG-NHS), acrylate-PEG-succinimidyl carboxymethyl ester (PEG-SCM), acrylate-PEG-succinimidyl amido succinate (PEG-SAS), acrylate-PEG-succinimidyl carbonate (PEG-SC), acrylate-PEG-succinimidyl glutarate (PEG-SG), acrylate-PEG-succinimidyl succinate (PEG-SS) and acrylate-PEG-maleimide (PEG-MAL).

6. A method of regulating a state of cancer cells, the method comprising:
   i) providing a system comprising:
      a) a crosslinked poly(ethylene glycol) (PEG)-based hydrogel composition comprising an acrylate-polymer-peptide macromer and a Type 1 ultraviolet (UV) photoinitiator, wherein the acrylate-polymer-peptide macromer comprises a first peptide and a first acrylate-PEG polymer covalently conjugated with the first peptide, wherein the first peptide consists of the sequence of X1-X2-X3-X4-X5-X6-X7-X8-X9-X10-X11, and wherein each of the X1 to X11 is G, P, Q, W, I or K,
      b) a cell culture medium in contact with the crosslinked PEG-based hydrogel composition, and
      c) cancer cells in contact with the cell culture medium and encapsulated in the crosslinked PEG-based hydrogel composition, wherein the cancer cells are in cell restricted survival dormancy; and
   ii) photopolymerizing a cell-adhesive macromer at 1-10 mM and a co-monomer at 9-10 mM with the crosslinked PEG-based hydrogel composition, and thereby the cancer cells are induced to switch from the cell restricted survival dormancy to: (i) a single cell balanced survival dormancy when the cancer cells are from cell line MDA-MB-231 or LM2-4175, or (ii) tumor mass balanced survival dormancy when the cancer cells are from cell line BOM-1833 or BrM2a-831, wherein the cell-adhesive macromer comprises a second acrylate-poly(ethylene glycol) covalently conjugated with a cell-adhesive peptide comprising a second peptide selected from the group consisting of RGDS (SEQ ID NO: 4), RDGS (SEQ ID NO: 5), RGES (SEQ ID NO: 6), REGS (SEQ ID NO: 7), IKVAV (SEQ ID NO: 8), VVIAK (SEQ ID NO: 9), YIGSR (SEQ ID NO: 10), YSRIG (SEQ ID NO: 11), DGEA (SEQ ID NO: 12), DAEG (SEQ ID NO: 13), and combinations thereof, and wherein the co-monomer comprises n-vinyl pyrrolidone.

7. The method according to claim 6, further comprising quantification of viability, proliferation, and/or viable cell density of the cancer cells.

8. The method according to claim 7, further comprising:
(i) measuring the viable cell density of the cancer cells on day 0 and day 15 or later;
and/or
(ii) evaluating a 3D cell/cluster morphology of the cancer cells.

9. The method according to claim 6, wherein the step (ii) further comprises adding a hydrogel digesting agent to the system.

10. The method according to claim 9 wherein the hydrogel digesting agent comprises collagenase I, collagenase IV, trypsin, proteinase-K, hyaluronidase, or combinations thereof.

11. The method according to claim 1, further comprising a step of screening an agent for effectiveness of the agent against the cancer cells after the step (ii).

12. The method according to claim 11, wherein the step of screening an agent comprises:
contacting the cancer cells with an effective amount of the agent selected from the group consisting of a drug, an antibody, and a biologic.

13. The method according to claim 12, further comprising fluorescence staining the cancer cells with calcein AM and ethidium homodimer and fluorescence imaging to quantify % live and % dead cancer cells.

14. The method according to claim 11, wherein the agent comprises one or more chemotherapeutic drugs.

15. The method according to claim 14, wherein the one or more chemotherapeutic drugs are selected from the group consisting of vinorelbine, cisplatin, ipilimumab, afatinib, dasatinib, cediranib, bevacizumab, PX-866, selumetinib, dalantercept, trebananib, doxorubicin, paclitaxel, and 5-fluorouracil.

16. The method according to claim 1, wherein the cancer cells are from cell line MDA-MB-231, BoM-1833, LM2-4175, or BrM2a-831.

17. The method according to claim 1, wherein the second peptide is RGDS (SEQ ID NO: 4).

18. The method according to claim 6, wherein the second peptide is the RDGS (SEQ ID NO: 5) and the co-monomer is n-vinyl pyrrolidone.

19. The method according to claim 6, wherein each of the first and the second acrylate-PEG is selected from the group consisting of acrylate-PEG-succinimidyl valerate (PEG-SVA), acrylate-PEG-N-hydroxylsuccinimide (PEG-NHS), acrylate-PEG-succinimidyl carboxymethyl ester (PEG-SCM), acrylate-PEG-succinimidyl amido succinate (PEG-SAS), acrylate-PEG-succinimidyl carbonate (PEG-SC), acrylate-PEG-succinimidyl glutarate (PEG-SG), acrylate-PEG-succinimidyl succinate (PEG-SS) and acrylate-PEG-maleimide (PEG-MAL).

20. The method according to claim 6, wherein the first peptide is selected from the group consisting of GGGPQGIWGQGK (SEQ ID NO: 1), GGGIQQWGPGGK (SEQ ID NO: 2), GGGGGIPQQWGK (SEQ ID NO: 3) and combinations thereof.

21. The method according to claim 6, further comprising a step of screening an agent for effectiveness of the agent against the cancer cells after the step (ii).

22. The method according to claim 21, wherein the step of screening an agent comprises:
contacting the cancer cells with an effective amount of the agent selected from the group consisting of a drug, an antibody, and a biologic.

23. The method according to claim 22, further comprising fluorescence staining the cancer cells with calcein AM and ethidium homodimer and fluorescence imaging to quantify % live and % dead cancer cells.

24. The method according to claim 21, wherein the agent comprises one or more chemotherapeutic drugs.

25. The method according to claim 24, wherein the one or more chemotherapeutic drugs are selected from the group consisting of vinorelbine, cisplatin, ipilimumab, afatinib, dasatinib, cediranib, bevacizumab, PX-866, selumetinib, dalantercept, trebananib, doxorubicin, paclitaxel, and 5-fluorouracil.

* * * * *

```
                        SEQUENCE LISTING

<160> NUMBER OF SEQ ID NOS: 13

<210> SEQ ID NO 1
<211> LENGTH: 12
<212> TYPE: PRT
<213> ORGANISM: Artificial Sequence
<220> FEATURE:
<223> OTHER INFORMATION: Artificial peptide sequence

<400> SEQUENCE: 1

Gly Gly Gly Pro Gln Gly Ile Trp Gly Gln Gly Lys
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Artificial peptide sequence

<400> SEQUENCE: 2

Gly Gly Gly Ile Gln Gln Trp Gly Pro Gly Gly Lys
1               5                   10

<210> SEQ ID NO 3
<211> LENGTH: 12
<212> TYPE: PRT
<213> ORGANISM: Artificial sequence
<220> FEATURE:
<223> OTHER INFORMATION: Artificial peptide sequence

<400> SEQUENCE: 3

Gly Gly Gly Gly Gly Ile Pro Gln Gln Trp Gly Lys
1               5                   10

<210> SEQ ID NO 4
<211> LENGTH: 4
<212> TYPE: PRT
<213> ORGANISM: Artificial Sequence
<220> FEATURE:
<223> OTHER INFORMATION: Cell-adhesive peptide sequence

<400> SEQUENCE: 4

Arg Gly Asp Ser
1

<210> SEQ ID NO 5
<211> LENGTH: 4
<212> TYPE: PRT
<213> ORGANISM: Artificial Sequence
<220> FEATURE:
<223> OTHER INFORMATION: Cell-adhesive peptide sequence

<400> SEQUENCE: 5

Arg Asp Gly Ser
1
```

```
<210> SEQ ID NO 6
<211> LENGTH: 4
<212> TYPE: PRT
<213> ORGANISM: Artificial Sequence
<220> FEATURE:
<223> OTHER INFORMATION: Cell-adhesive peptide sequence

<400> SEQUENCE: 6

Arg Gly Glu Ser
1

<210> SEQ ID NO 7
<211> LENGTH: 4
<212> TYPE: PRT
<213> ORGANISM: Artificial Sequence
<220> FEATURE:
<223> OTHER INFORMATION: Cell-adhesive peptide sequence

<400> SEQUENCE: 7

Arg Glu Gly Ser
1

<210> SEQ ID NO 8
<211> LENGTH: 5
<212> TYPE: PRT
<213> ORGANISM: Artificial Sequence
<220> FEATURE:
<223> OTHER INFORMATION: Cell-adhesive peptide sequence

<400> SEQUENCE: 8

Ile Lys Val Ala Val
1               5

<210> SEQ ID NO 9
<211> LENGTH: 5
<212> TYPE: PRT
<213> ORGANISM: Artificial sequence
<220> FEATURE:
<223> OTHER INFORMATION: Cell-adhesive peptide sequence

<400> SEQUENCE: 9

Val Val Ile Ala Lys
1               5

<210> SEQ ID NO 10
<211> LENGTH: 5
<212> TYPE: PRT
<213> ORGANISM: Artificial sequence
<220> FEATURE:
<223> OTHER INFORMATION: Cell-adhesive peptide sequence

<400> SEQUENCE: 10

Tyr Ile Gly Ser Arg
1               5

<210> SEQ ID NO 11
<211> LENGTH: 5
<212> TYPE: PRT
<213> ORGANISM: Artificial sequence
<220> FEATURE:
<223> OTHER INFORMATION: Cell-adhesive peptide sequence

<400> SEQUENCE: 11

Tyr Ser Arg Ile Gly
1               5

<210> SEQ ID NO 12
```

```
-continued

<211> LENGTH: 4
<212> TYPE: PRT
<213> ORGANISM: Artificial sequence
<220> FEATURE:
<223> OTHER INFORMATION: Cell-adhesive peptide sequence

<400> SEQUENCE: 12

Asp Gly Glu Ala
1

<210> SEQ ID NO 13
<211> LENGTH: 4
<212> TYPE: PRT
<213> ORGANISM: Artificial sequence
<220> FEATURE:
<223> OTHER INFORMATION: Cell-adhesive peptide sequence

<400> SEQUENCE: 13

Asp Ala Glu Gly
1
```